US 9,068,986 B2
(12) United States Patent
Jin et al.

(10) Patent No.: US 9,068,986 B2
(45) Date of Patent: *Jun. 30, 2015

(54) INFLUENZA B VIRUSES HAVING ALTERATIONS IN THE HEMAGGLUTININ POLYPEPTIDE

(71) Applicant: MEDIMMUNE, LLC, Gaithersburg, MD (US)

(72) Inventors: Hong Jin, Cupertino, CA (US); Zhongying Chen, Cupertino, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/161,430

(22) Filed: Jan. 22, 2014

(65) Prior Publication Data

US 2014/0199683 A1 Jul. 17, 2014

Related U.S. Application Data

(63) Continuation of application No. 12/599,761, filed as application No. PCT/US2008/067301 on Jun. 18, 2008, now Pat. No. 8,673,613.

(60) Provisional application No. 60/944,600, filed on Jun. 18, 2007.

(51) Int. Cl.
| | |
|---|---|
| *C12N 7/00* | (2006.01) |
| *C12N 7/02* | (2006.01) |
| *G01N 33/569* | (2006.01) |
| *A61K 39/145* | (2006.01) |
| *C07K 14/005* | (2006.01) |
| *A61K 39/00* | (2006.01) |

(52) U.S. Cl.
CPC ........ *G01N 33/56983* (2013.01); *A61K 39/145* (2013.01); *A61K 2039/5254* (2013.01); *C07K 14/005* (2013.01); *C12N 7/00* (2013.01); *C12N 2760/16122* (2013.01); *C12N 2760/16222* (2013.01); *C12N 2760/16234* (2013.01); *C12N 2760/16243* (2013.01); *C12N 2760/16261* (2013.01)

(58) Field of Classification Search
None
See application file for complete search history.

(56) References Cited

U.S. PATENT DOCUMENTS

| | | | |
|---|---|---|---|
| 3,874,999 | A | 4/1975 | Zaremba et al. |
| 3,992,522 | A | 11/1976 | Chanock et al. |
| 4,000,257 | A | 12/1976 | Cano |
| 4,057,626 | A | 11/1977 | Metzgar et al. |
| 4,071,618 | A | 1/1978 | Konobe et al. |
| 4,337,242 | A | 6/1982 | Markus et al. |
| 4,338,296 | A | 7/1982 | Lobmann |
| 4,500,512 | A | 2/1985 | Barme |
| 4,512,285 | A | 4/1985 | McGehee |
| 4,512,972 | A | 4/1985 | Schmidt-Ruppin |
| 4,634,666 | A | 1/1987 | Engleman et al. |
| 4,659,569 | A | 4/1987 | Mitsuhashi et al. |
| 5,166,057 | A | 11/1992 | Palese et al. |
| 5,690,937 | A | 11/1997 | Parkin |
| 5,716,821 | A | 2/1998 | Wertz |
| 5,789,229 | A | 8/1998 | Wertz et al. |
| 5,820,871 | A | 10/1998 | Palese et al. |
| 5,840,520 | A | 11/1998 | Clark et al. |
| 5,854,037 | A | 12/1998 | Palese et al. |
| 5,922,326 | A | 7/1999 | Murphy |
| 6,033,886 | A | 3/2000 | Conzelmann |
| 6,039,958 | A | 3/2000 | Koyama |
| 6,090,391 | A | 7/2000 | Parkin |
| 6,146,642 | A | 11/2000 | Garcia-Sastre et al. |
| 6,146,873 | A | 11/2000 | Kistner et al. |
| 6,168,943 | B1 | 1/2001 | Rose |
| 6,177,082 | B1 | 1/2001 | Dowling et al. |
| 6,344,354 | B1 | 2/2002 | Webster |
| 6,649,372 | B1 | 11/2003 | Palese et al. |
| 6,656,720 | B2 | 12/2003 | Groner et al. |
| 6,887,699 | B1 | 5/2005 | Palese et al. |
| 6,951,754 | B2 | 10/2005 | Hoffmann |
| 7,037,707 | B2 | 5/2006 | Webster et al. |
| 7,262,045 | B2 | 8/2007 | Schwartz et al. |
| 7,465,456 | B2 | 12/2008 | Hoffmann |
| 8,012,736 | B2 | 9/2011 | Jin et al. |
| 8,093,033 | B2 | 1/2012 | Kemble |
| 8,409,843 | B2 | 4/2013 | Kemble |
| 8,574,591 | B2 | 11/2013 | Hoffmann et al. |

(Continued)

FOREIGN PATENT DOCUMENTS

| | | |
|---|---|---|
| CA | 2118234 | 4/1993 |
| CN | 1221795 | 7/1999 |
| EP | 0480949 | 4/1992 |
| EP | 0702085 | 3/1996 |
| EP | 0780475 | 6/1997 |

(Continued)

OTHER PUBLICATIONS

"Influenza Strain Details for \B/Jiangsu/10/03", Apr. 5, 2011, XP002633783, Retrieved from the Internet: URL: http://www.fludb.org/brc/fluStrainDetails.do?strainName=B/Jiangsu/10/03 &decorator=influenza [retrieved on Apr. 20, 2011].

(Continued)

*Primary Examiner* — Mary E Mosher
*Assistant Examiner* — Myron Hill
(74) *Attorney, Agent, or Firm* — Grant IP, Inc.

(57) ABSTRACT

The present invention encompasses methods of producing influenza B viruses in cell culture. The influenza B viruses may have desirable characteristics, such as enhanced replication in eggs and may be used, for example, in vaccines and in methods of treatment to protect against influenza B virus infection.

11 Claims, 47 Drawing Sheets

(56) References Cited

U.S. PATENT DOCUMENTS

| | | | |
|---|---|---|---|
| 8,673,613 B2* | 3/2014 | Jin et al. | 435/235.1 |
| 8,722,059 B2 | 5/2014 | Hoffman et al. | |
| 2002/0119445 A1 | 8/2002 | Parkin | |
| 2002/0164770 A1 | 11/2002 | Hoffmann | |
| 2003/0035814 A1 | 2/2003 | Kawaoka et al. | |
| 2003/0108859 A1 | 6/2003 | Kistner et al. | |
| 2003/0147916 A1 | 8/2003 | Ferko | |
| 2004/0029251 A1 | 2/2004 | Hoffman et al. | |
| 2004/0137013 A1 | 7/2004 | Katinger | |
| 2005/0042229 A1 | 2/2005 | Yang | |
| 2005/0054846 A1 | 3/2005 | Webster et al. | |
| 2005/0158342 A1 | 7/2005 | Kemble | |
| 2005/0186563 A1 | 8/2005 | Hoffmann | |
| 2005/0266026 A1 | 12/2005 | Hoffmann | |
| 2006/0110406 A1 | 5/2006 | Kemble | |
| 2007/0161085 A1 | 7/2007 | Trager et al. | |
| 2009/0175907 A1 | 7/2009 | Hoffman et al. | |
| 2009/0208527 A1 | 8/2009 | Kemble | |
| 2010/0322969 A1 | 12/2010 | Jin et al. | |
| 2012/0020997 A1 | 1/2012 | Hoffman et al. | |
| 2012/0196371 A1 | 8/2012 | Kemble et al. | |
| 2012/0288521 A1 | 11/2012 | Hoffmann et al. | |
| 2013/0189762 A1 | 7/2013 | Kemble et al. | |
| 2014/0134208 A1 | 5/2014 | Hoffmann et al. | |
| 2014/0220075 A1 | 8/2014 | Hoffman et al. | |

FOREIGN PATENT DOCUMENTS

| | | |
|---|---|---|
| EP | 0863202 | 9/1998 |
| EP | 0864645 | 9/1998 |
| EP | 1597400 | 2/2005 |
| EP | 1826269 | 8/2007 |
| GB | 660109 | 10/1951 |
| WO | WO 91/03552 | 3/1991 |
| WO | WO 93/21306 | 10/1993 |
| WO | WO 96/10632 | 4/1996 |
| WO | WO 96/10633 | 4/1996 |
| WO | WO 96/34625 | 11/1996 |
| WO | WO 97/06270 | 2/1997 |
| WO | WO 97/12032 | 4/1997 |
| WO | WO 97/14434 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 00/03019 | 1/2000 |
| WO | WO 00/53786 | 9/2000 |
| WO | WO 00/60050 | 10/2000 |
| WO | WO 01/22992 | 4/2001 |
| WO | WO 01/83794 | 11/2001 |
| WO | WO 03/091401 | 6/2003 |
| WO | WO 2005/014862 | 2/2005 |
| WO | WO 2005/062820 | 7/2005 |
| WO | WO 2005/115448 | 12/2005 |
| WO | WO 2006/041819 | 4/2006 |
| WO | WO 2008/157583 | 12/2008 |

OTHER PUBLICATIONS

"Influenza B virus (B/Jiangsu/10/2003 (recomb)) segment 4 hemagglutinin (HA) gene, partial cds.," [online], 2007. 05, [searched on Jun. 20, 2013], Accession No. EF473637.
Anderson, et al, ":Evaluation of a Cold-Adapted Influenza B/Texas/84 Reassortant Virus (CRB-87) Vaccine in Young Children," Journal of Clinical Microbiologu, Sep. 1993, p. 2230-2234.
Banerjee and Barik, 1992, "Gene expression of vesicular stomatitis virus genome RNA", Virology. 188(2):417-28.
Baron and Barrett, 1997, "Rescue of Rinderpest Virus from Cloned cDNA", J. Virol. 71:1265-1271.
Baron et al., Electroporation of antibodies, DNA, and other macromolecules into cells: a highly efficient method, Journal of Immunological Methods, 2000, vol. 242, pp. 115-126.
Basler et al., Mutation of Neuraminidase Cysteine Residues Yields Temperature-Sensitive Influenza Viruses, Journal of Virology, Oct. 1999, vol. 73, No. 10, p. 8095-8103.
Beare et al., 1975, "Trials in Man with Live Recombinants Made from A/NPR/8/34 (HO N1) and Wild H3 N2 Influenza Viruses", Lancet 2(7938):729-732.
Belshe, 1995 "A Review of Attenuation of Influenza Viruses by Genetic manipulationn," American Journal of Respiratory and Critical Care Medicine 152[4 Pt 2], 572-575. 1995.
Belshe, et al., "The Efficacy of live attenuated, cold-adapted, trivalent intranasal influenza virus vaccine in children," N. Eng J Med 338:1405-1412.
Bergmann, el al., "The relative amount of an influenza A virus segment present in the viral particle is not affected by a reduction in replication of that segment,". Journal of General Virology, 1995,76:3211-3215.
Boyce et al., 2001, "Safety and immunogonicity of adjuvanted and unadjuvanled subunit influenza vaccines administered Intranasally to healthy adults", Vaccine 19:217-226.
Boyer et al., 1994, "Infectious transcripts and cDNA clones of RNA viruses", Virology. 198(2):415-26.
Brandt et al., 2001, "Molecular Determinants of Virulence, Cell Tropism. and Pathogenic Phenotype of Infectious Bursal Disease Virus". Journal of Virology 75(24):11974-11982.
Brigden and Elliott. 1996, "Rescue of a Segmented Negative-Strand RNA Virus Entirely from Cloned Complementary DNAS", Proc. Natl. Acad. Sci. USA 93:15400-15404.
Buchholz et al., 1999 "Generation of Bovine Respiratory Syncytial Virus (BRSV) from cDNA: BRSV NS2 Is Not Essential for Virus Replication in Tissue Culture. and the Human RSV Leader Region Acts as a Functional BRSV Genome Promoter". J. Virol. 73:251-259.
Bukreyev et al., 1996, "Recovery of infectious respiratory syncytial virus expressing an additional, foreign gene", J Virol. 70(10):6634-6641.
Burmeister, "Sequence and crystallization of influenza virus b/Beijing/1/87 neuraminidase" Virology, 1991, vol. 180, No. 1, pp. 266-272.
Castrucci et al., 1995, "Reverse genetics system for generation of an influenza A virus mutant containing a deletion of the carboxyl-terminal residue of M2 protein", J Virol. 69(5):2725-2728.
Chen et al., 1999, "Influenza A virus NS1 protein targets poly (A)-binding protein II of the cellular 3'-end processing machinery", EMBO 18: 2273-2283.
Chen et al., "Genetic mapping of the cold-adapted phenotype of B/Ann Arbor/1/66, the master donor virus for live attenuated influenza vaccines (FluMist)" Virology vol. 345, No. 2, 2006, pp. 416-423.
Chen et al., "Molecular studies of temperature-sensitive replication of the cold-adapted B/Ann Arbor/1/66, the master donor virus for live attenuated influenza FluMist vaccines.", Virology Oct. 25, 2008 LNKDPUBMED: 18804834, vol. 380, No. 2, Oct. 25, 2008, pp. 354-362.
Chen et al., "Stabilizing the glycosylation pattern of influenza B hemagglutinin following adaptation to growth in eggs", Vaccine, Elsevier Ltd, GB, vol. 26, No. 3, Nov. 26, 2007, pp. 361-371.
Clarke et al., 2000, "Rescue of mumps virus from cDNAJ", J Virol. 74(10):4831-8.
Collins et al., 1991, "Rescue of Synthetic Analogs of Respiratory Syncytial Virus Genomic RNA and Effect of Truncations and Mutations on the Expression of a Foreign Reporter Gene", Proc. Natl. Acad. Sci. USA 88:9663 9657.
Collins et al., 1995, "Production of infectious human respiratory syncytial virus from cloned cDNA confirms an essential role . . . " PNAS 92: 11563-7.
Collins et al., 1996, "Parainfluenza Viruses", Fields Virology, Lippincott-Raven Publishers, Phila., Chapter 41, pp. 1205-1241.
Conzelmann et al., 1994, "Rescue of synthetic genomic RNA analogs of rabies virus by plasmid-encoded proteins", J Virol. 68(2):713-9.
Conzelmann et al., 1996, "Genetic engineering of animal RNA viruses", Trends Microbiol. 4(10):386-93.
Conzelmann et al., 1996, "Genetic manipulation of non-segmented negative-strand RNA viruses", J Gen Virol. 77 (Pt 3):381-389.

(56) References Cited

OTHER PUBLICATIONS

Conzelmann et al., 1998, "Nonsegmented negative-strand RNA viruses: genetics and manipulation of viral genomes", Annu Rev Genet. 32:123-62.
Cox. NJ et al., "Identification of sequence changes in the cold-adapted, live attenuated influenza vaccine strain . . . ". Virology. Dec. 1998; 167(2)554-567.
De and Banerjee, 1985, "Requirements and Functions of Vesicular Stomatitis Virus Land NS Proteins in the Transcription Process in vitro", Biochem. Biophys. Res. Commun. 126:40-49.
De and Banerjee, 1993, "Rescue of synthetic analogs of genome RNA of human parainfluenza virus type 3", Virology, 96(1 ):344-8.
De and Banerjee, 1994, "Reverse genetics of negative strand RNA viruses", Indian J Biochem Biophys. 31(5):367-76.
De la Luna et al., 1993. "Influenza virus naked RNA can be expressed upon transfection into cells co-expressing the three subunits of the polymerase and the nucleoprotein from simian virus 40 recombinant viruses", J Gen Virol. 74 (Pt 3):535-9.
De La Luna et al., 1995, "Influenza virus NS1 Protein Enhances the Rate of Translation Initiation of Viral mRNAs", J. of Virol. 69: 2427-2433.
DeBorde et al., 1988, Sequence comparison of wild-type and cold-adapted B/Ann Arbor/1/66 influenza virus genes Virology 163(2):429-443.
Dimock et al., 1993, Rescue of synthetic analogs of genomic RNA and replicative-intermediate RNA of human parainfluenza virus type 3 . . . J Virol. 67(5):2772-8.
Donabedian et al., "A Mutation in the PA Protein Gene of Cold-Adapted B/Ann Arbor/1/66 Influenza Virus Associated with Reversion of Temperature Sensitivity and Attenuated Virulence," Virology, 163, p. 444-451, (1988).
Dreher and Hall, 1988, "Mutational Analysis of the Sequence and Structural Requirements in Brome Mosaic Virus RNA for Minus Strand Promoter Activity", J. Mol. Biol. 201:31-40.
Dreher et al., 1984, "Mutant Viral RNAs Synthesized in vitro Show Altered Aminoacylation and Replicase Template Activities", Nature 311:171-175.
Dunn et al., 1995, "Transcription of a recombinant bunyavirus RNA template by transiently expressed bunyavirus proteins", Virology, 211 (1): 133-43.
Durbin et al., 1997, "Recovery of infectious Human Parainfluenza Virus Type 3 from cDNA", Virol. 235:323-332.
Edwards et al.. 1994. "A randomized controlled trial of cold adapted and inactivated vaccines for the prevention of influenza A disease", J Infect Dis 169:68-76.
Egorov et al., Transfectant Influenza A Viruses with Long Deletions in the NS1 Protein Grow Efficiently in Vero Cells, Journal of Virology, Aug. 1998, vol. 72, No. 8, p. 6437-6441.
Elliot et al., 1997, Abstract # 96 10.sup.th International conference on Negative Strand Viruses.
Elliott et al., 1991, "Some highlights of virus research in 1990", J Gen Virol.72 (Pt. 8):1761-79. Review. No abstract available.
Emerson and Yu, 1975, "Both NS and L Proteins are Required for in vitro RNA SynthesiS by Vosicular Stomatitis Virus", J. Virol. 15:1348-1356.
Enami and Palese, 1991, "High-Efficiency Formation of Influenza Virus Transfectants", J. Virol. 65:2711-2713.
Enami et al., 1991, "An influenza virus containing nine different RNA segments", Virology. 185(1):291-8.
Enami et aL, 1990, "Introduction of Site SpeCific Mutations into the Genome of Influenza Virus", Proc Natl Acad Sci USA 87: 3802-3805.
Enami et al., "Characterization of Influenza Virus NS1 Protein by Using a Novel Helper-Virus-Free Reverse Genetic System" Journal of Virology, 2000, 74(12):5556-5561.
European Search Report mailed on: May 4, 2011 in European Application No. 08771329 filed on: Jun. 18, 2008.
Extended European Search Report dated: Aug. 9, 2012 in European Application No. EP12168901 filed: Apr. 25, 2003.
Fahey and Schooley, 1992, "Status of Immune-Based Therapies in HIV Infection and AIDS", Clin. Exp. Immunol. 88:1-5.

Flandorfer et al., 2003, •Chimeric Influenza A Viruses with a Functional Influenza B Virus Neuraminidase or Hemagglutinin, J. of Virology—77(17):9116-9123.
Flick. et al., "Promoter elements in the influenza vRNA terminal structure," RNA, 1996: 2(10):1046-1057.
Fodor et al., "Rescue of Influenza A Virus from Recombinant DNA". J. of Virology, Am. Society for Microbiology. Nov. 1999, vol. 73, No. 11, pp. 9679-9682.
Fortes et al., 1994, "Influenza virus NS 1 protein inhibits pre-mRNA splicing and blocks mRNA nucleocytoplasmic transport", EMBO 13: 704-712.
Furminger, "Vaccine Production," Textbook of Influenza, pp. 324-332 (1996).
Garcia-Sastre A, Palese p, 1993. "Genetic manipulation of negative-strand RNA virus genomes", Annu Rev Microbiol. :47:765-90.
Garcin et al., 1995, A highly recombinogenic system for the recovery of infectious sendal paramyxovirus from cDNA: generation of a novel copy-back nondefeclive interfering virus•, EMBO J. 14: 6087-6094.
Ghendon, "Cold-Adapted, Live Influenza Vaccines Developed in Russia," Textbook of Influenza, Chapter 29, pp. 391-399 (1998).
Giudice et al., An MF59-adjuvanted inactivated influenza vaccine containing A/Panama/ 1999 (H3N2) induced broader serological protein against hetervariant influenza vaccine strain A/Fujian/2002 than a subunit and split influenza vaccine, 2006, Vaccine, vol. 24, pp. 3063-3065.
Goto et al., 1997, "Mutations Affecting the Sensitivity of the Influenza Virus Neuraminidase to 4-Guanidino-2,4-Dideoxy-2,3 Dehydro-N-Acetyineuraminic Acid", Virol. 238:265-272.
Govorkova, et al., "African Green Monkey Kidney (Vero) Cells Provide an Alternative Host Cell System for Influenza A and B Viruses". Journal of Virology. American Society for Microbiology. Aug. 1996. vol. 70. No. 8, pp. 5519-5524.
Grosfeld et al., 1995, RNA replication by respiratory syncytial virus (RSV) is directed by the N. P. and L proteins: transcription also occurs under lhese conditions but requires RSV superinfection for efficient synthesis of full-length mRNA. J Virol. 69(9):5677-86.
Guan, Vi, et al., "Molecular Characterization of H9N2 Influenza Viruses: Were They the Donors of the "Internal" Genes of H5N1 Viruses in Hong Kong?"Proc. Nail. Acad. Sci., U.S.A., Aug. 1999, vol. 96, pp. 9363-9367.
Ha et al., "X-ray structures of H5 avian and H9 swine influenza virus hem agglutinins bound to avian and human receptor analogs", PNAS, USA, vol. 98, No. 20, Sep. 25, 2001, pp. 11181-11186.
Halperin et al., "Saftey and immunogenicity of a new influenza vaccine grown in a mammailian cell culture," Vaccine 1998, vol. 16, No. 13, p. 1331-1335.
Hardy et al., Egg Fluids and Cells of the Chorioallantoic Membrane of Embryonated Chicken Eggs Can Select Different Variants of Influenza A (H3N2) Viruses, 1995. Virology, vol. 211, pp. 302-306.
Hatada and Fukudo, 1992, "Binding of influenza A virus NS1 protein to dsRNA in vitro", J. of Gen. Virol. 73: 3325-3329.
He et al., 1997, "Recovery of Infectious SV5 from Cloned DNA and Expression of a Foreign Gene", Virol. 237:249-260.
Herlocher et al., "Sequence Comparisons of AIAAJ6/60 Influenza Viruses: Mutations Which May Contribute to Attenuation", Virus Research, 42:11-25; (1996).
Hillman Maurice R., 2000, "Vaccines in historic evolution and perspective: a narrative of vaccine discoveries", Vaccine 18:1436-1447.
Hoffman and Banerjee, 1997. "An Infectious Clone of a Human Parainfluenza Virus Type 3", J. Virol. 71:4272-4277.
Hoffman et al., "A DNA transfection system for generation of influenza A virus from eight plasm ids", PNAS, May 23, 2000, vol. 97, No. 11, pp. 6108-6113.
Hoffman et al., 2002, "Rescue of influenza B virus from eight plasmids", PNAS 99: 11411-11416.
Hoffman et al., "Multiple gene 1-15 segments control the temperature sensitivity and attenuation phenotypes of ca B/Ann Arbor/1/66.", Journal of Virology Sep. 2005 LNKDPUBMED: 16103152, vol. 79, No. 17, Sep. 2005, pp. 11014-11021.
Hoffman et al., "Unidirectional RNA polymerase I-polymerase II transcription system for generation of influenza A virus from eight plasmids", J. of Gen Vir, 2000, 61, 2843-2847.

(56) References Cited

OTHER PUBLICATIONS

Hoffman et al.. "Eight-Plasmid Resue System for Influenza A Virus". International Congress Series. 1219:1007-1013; (2001).

Hoffman et al.. "Eight-Plasmid Resue System for Rapid Generation of Influenza Virus Vaccines", Vaccine, 20:3165-3170; (2002).

Hoffman et al.. 2000. "Ambisense approach for the generation of influenza A virus: vRNA and mRNA synthesis from one template", Virology 267:310-7.

Hoffmann et al., "Characterization of the Influenza A Virus Gene Pool in Avian Species in Southern China: Was H6N1 a Derivative or a Precursor of H5N1?" J. Virology. 2000. vol. 74. No. 14. pp. 6309-6315.

Hoffmann et al., "Universal primer set for the full-length amplification of all Influenza A viruses." Arch Virol. Dec. 2001; 146(12):2275-89.

Hoffmann, Erich, Aufbau eines RNA-Polymerase I-Vektorsystems zur gezlelten Mutagenese von Influenza A Vlren, Glessen 1997 (Doctoral Dissertation).With translation (Generation of an RNA-Polymerase Vector System for the Selective Mutagenesis of Influenza A).

Huang et al.. 1990, "Determination of Influenza virus proteins required for genome replication". J Virol. 64( 11 ):5669-5673.

International Search Report and Written Opinion maild on: Feb. 10, 2006 in International Application No. PCT/US2004/42669 filed on: Dec. 22, 2004 and published as WO 2005/062820 on Jul. 14, 2005.

International Search Report and Written Opinion maild on: Feb. 9, 2004 in International Application No. PCT/US2003/12728 filed on: Apr. 23, 2003 and published as WO 2003/091401 on Nov. 6, 2003.

International Search Report and Written Opinion maild on: Oct. 11, 2006 in International Application No. PCT/US2005/017734 filed on: May 20, 2005 and published as WO 2005/115448 on Dec. 8, 2005.

International Search Report and Written Opinion maild on: Sep. 2, 2008 in International Application No. PCT/US2008/067301 filed on: Jun. 18, 2008 and published as WO 2008/0157583 on Dec. 24, 2008.

International Search Report and Written Opinion mailed on: Feb. 10, 2006 in International application No. PCT/US45/42669 filed on Dec. 22, 2004.

Jackson et al. 2002, "A reverse genetics approach for recovery of recombinant influenza B Viruses . . . " J. of Virology 76(22): 11744-11747.

Jin et al., "Imparting Temperature Sensitivity and Attenuation in Ferrets to Al Puerto Rico/6/34 Influenza Virus by . . .". J. of Virology. Am. Society for Microbiology, pp. 995-998, Jan 2004.

Jin et al., Multiple Amino acid residues confer temperature sensitivity to human influenza vaccine strains (FluMist) derived from cold-adapted A/Ann Arbor/6/60, 2003, Virology, vol. 302, pp. 18-24.

Jin-Hua Liu et al: "Genetic Conservation of Hemagglutinin Gene of H9 Influenza Virus in Chicken Population in Mainland China" Virus Genes, Kluwer Academic Publishers, Bo, vol. 29, No. 3, Dec. 1, 2004, pp. 329-334.

Kaplan et al.. 1985. "In vitro Synthesis of Infectious Poliovirus RNA". Proc. Natl. Acad. Sci. USA 82:8424-8428.

Katinger et al., "Attenuated Influenza Virus as a Vector for Mucosal Immunization against HIV-1", Vaccines, pp. 315-319, (1997).

Kato et al., 1996, "Initiation of Sendai Virus Multiplication from Transfected cDNA or RNA with Negative or Positive Sense", Genes Cells 1 :569-579.

Keitel. et al., "Live Cold-Adapted, Reassortant Influenza Vaccines (USA)," Textbook of Influenza, Chapter 28, pp. 373-390 (1998).

Kimura et al., 1993, "An in vivo study of the replication origin in the influenza virus complementary RNA". J Biochem (Tokyo) 113(1):88-92.

Kimura et al., 1992, Transcription of a recombinant influenza virus RNA in cells that can express the influenza virus RNA polymerase and nucleoprotein genes•, J Gen Virol. 73 (Pt 6):1321-1328.

Kistner et al., Development of a Mammalian Cell (Vero) Derived Candidate Infleunza Virus Vaccine, Vaccine, 1998, vol. 16, No. 9-10, pp. 960-968.

Kobayashi, 1992, Reconstitution of influenza virus RNA polymerase from three subunits expressed using recombinant baculovirus system. Virus Res. 22(3):235-245.

Konarska et al., 1990, "Structure of RNAs replicated by the DNA-dependent T7 RNA polymerase", Cell. 63(3):609-18.

Krystal et al., 1986, Expression of the Three Influenza Virus Polymerase Proteins in a Single Cell Allows Growth Complementation of Viral Mutants•, Proc. Nail. Acad. Sci. USA 83:2709-2713.

Kunkel, 1985. "Rapid and Efficient Site-Specific MutagenesiS without Phenotypic Selection", Proc. Natl. Acad. Sci. USA 82:488•492.

Lamb et al., 1996, Fundamental Virology 3.sup.rd ed. Chapters 20 and 21.

Lawson et al., 1995, "Recombinant vesicular stomatitis viruses from DNA", Proc Natl Acad Sci U S A.92(1 0):4477-81.

Levis et al., 1986, "Deletion Mapping of Sindbis Virus 01 RNAs Derived from cDNAs Defines the Sequences Essential for Replication and Packaging", Cell 44:137-145.

Li et al., Virus Research, 1995, 37:153-161.

Li et al.. 1999, "Recombinant influenza A virus vaccines for the pathogenic human A/Hong Kong/97 (H5N1) viruses," J. of Infectious Diseases. 179:1132-8.

Lu Bin et al: "Improvement of influenza A/Fujian/411/02 (H3N2) virus growth in embryonated chicken eggs by balancing the hemagglutinin and neuraminidase activities, using reverse genetics" Journal of Virology, vol. 79, No. 11, Jun. 2005, pp. 6763-6771.

Lugovtsev et al., "Changes of the receptor-binding properties of influenza B virus B/Victoria/504/2000 during adaptation in chicken eggs", Virology, Academic Press,Orlando, US, vol. 394, No. 2, Nov. 25, 2009, pp. 218-226.

Lugovtsev V.Y. et al.: 'Generation of the influenza B viruses with improved growth phenotype by substitution of specific amino acids of hemagglutinin' Virology vol. 365, pp. 315-323.

Lugovtsev V.Y. et al.: 'Mutational pattern of influenza B viruses adapted to high growth replication in embryonated eggs' Virus Research vol. 109, No. 2, 2005, pp. 149-157.

Luytjes et al., "Amplification, expression, and packaging of foreign gene by influenza virus," 1989, Cell, 59:1107-1113.

Maassab et al., Evaluation of a Cold-Recombinant Influenza Virus Vaccine in Ferrets, J. of Infectious Diseases, 146:780-900; (1982).

Maassab et al., The Development of Live Attenuated Cold-Adapted Influenza Virus Vaccine for Humans,Reviews in Medical Virology, 1999, vol. 9, pp. 237-244.

Maassab et al., "Development and characterization of cold-adapted viruses for use as live virus vaccines," Vaccine, vol. 3, Dec. 1985, pp. 355-369.

Maassab et al.. "Evaluation of a Cold-Recombinant Influenza Virus Vaccine in Ferrets", J. of Infectious Diseases. 146:780-900; (1982).

Maassab, Adaptation and growth characteristics of influenza virus at 25 degrees C Nature. 213:612-614 (1967).

Marten et al., "Production of influenza virus in Cell Cultures for Vaccine Preparation", Novel Slrategies in Design and Production of Vaccines, pp. 141-151; (1996).

Martin at al., 1998, "Studies of the Binding Properties of Influenza Hemagglutinin Receptor-Site Mutants", Virology 241:101-111.

Medeiros Rita et al: "Hemagglutinin residues of recent human A (H3N2) influenza viruses that contribute to the inability to agglutinate chicken erythrocytes", Virology, vol. 289, No. 1, Oct. 10, 2001, pp. 74-85.

Melkonyan et al., Electroporation efficiency in mammalian cells is increased by dimethyl sulfoxide (DMSO). Nucleic Acids Research, 1996, vol. 24, No. 21, pp. 4356-4357.

Mena et al., 1994, "Synthesis of biologically active influenza virus core proteins using a vaccinia virus-T7 RNA polymerase expression system", J Gen Virol. 75 (Pt 8):2109-14.

Mena et al., 1996, "Rescue of a Synthetic Chloramphenicol Acetyltransferase RNA into Influenza Virus-Like Particles Obtained from Recombinant Plasmids", J. Virol. 70: 5015-S024.

Merten at at. "Production of influenza virus in Cell Cultures for Vaccine Preparation", Novel Strategies in Design and Production of Vaccines, pp. 141-151; (1996).

(56) References Cited

OTHER PUBLICATIONS

Mochalova L et al.: "Receptor-binding properties of modern human influenza viruses primarily isolated in Vero and MDCK ceils and chicken embryonated eggs", Virology, Academic Press,Orlando, US, vol. 313, No. 2, Sep. 1, 2003, pp. 473-480.
Moyer et al., 1991, "Assembly and transcription of synthetic vesicular stomatitis virus nucleocapsids", J Virol. 65(5):2170-8.
Murphy & Coelingh, "Principles Underlying the Development and Use of Live Attenuated Cold-Adapted Influenza A and B Virus Vaccines", ViralImmunol. 15:295-323; (2002).
Muster et al., 1991, "An influenza A virus containing influenza B virus S' and 3' noncoding regions on the neuraminidase gene is attenuated in mice:". Proc Natl Acad Sci U S A.88(12):5177-81.
Naito and Ishihama, 1976, "Function and Structure of RNA Polymerase from Vesicular Stomatitis Virus", J. Biol. Chern. 251 :4307-4314.
Nakagawa et al., "Neutralizing epitopes specific for influenza B virus Yamagata group strains are in the loop", Journal of General Virology vol. 84, No. 4, Apr. 2003, pp. 769-773.
Nakajima et al., 2003. "Restriction of Amino Acid Change in Influenza A Virus H3HA: Comparison of Amino Acid Changes Observed . . . "; J, of Virology 77(18):10088-10098.
Nara et al., 1987. "Simple, Rapid, Quantitative, Syncytlum-Fonmlng MIcorassay for the Detection of Human Immunodeficiency Virus Neutralizing Antibody", AIDS Res. Hum. Retroviruses 3:283-302.
Nemeroff et al., 1998, "Influenza Virus NS1 Protein Interacts with the Cellular 30 kDa Subunit of CPSF and Inhibits 3' End Formation of Cellular Pre-mRNAs", Mol. Cell1 :991•1000.
Neumann et al., 1994, "RNA Polymerase I-Mediated Expression of Influenza Viral RNA Molecules", Virol, 202:477-479.
Neumann et al. Generation of influenza A viruses entirely from cloned cDNAsn, Proc. Natl. Acad. Sci.. Microbiology, Aug. 1999, vol. 96, pp. 9345-9350.
Neumann G., et al., "Generation of Influenza A Virus from Clones cDNAs—Historical Perspective and Outlook for the New Millenium," Rev.Med. Virol, (2002)12; 13-30.
Neumann, et al., "Genetic Engineering of Influenza and Other Negative-Strand RNA Viruses Containing Segmented Genomes," Advances in Virus Research, 1999; 53: 265-300.
Nichol et al., "Effectiveness of live, attenuated Intranasal influenza vlrus vaccine in healthy, working adults: a randomized controlled trial", JAMA 281:137-44.
Oxford et al., "A host-cell-selected variant of influenza B virus with a single nucleotide substitution in HA affecting a potential glycosylation site was attenuated in virulence for volunteers," Arch Virol., vol. 110, pp. 37-46.
Oxford et al., "Direct isolation in eggs of influenza A (H1N1) and B Virus with haemagglutinins of different antigenic and amino acid compositions," J. Gen Virol 1991, vol. 72, No. 1, pp. 185-189.
Palese et al., 1996, "Negative-Strand RNA Viruses: Genetic Engineering and Applications", Proc. Natl. Acad. Sci. USA 93,11354-11358.
Paltnaik et al., 1991, •Cells that express all flVe proteins of vesicular stomatitis virus from cloned cDNAs support replication, assembly, and budding of defective Interfering particles, Proc Nail Acad Sci USA. 88(4):1379-83.
Paragas et al., "Influenza B and C Virus NEP (NS2) Proteins Possess Nuclear Export Activities," Journal of Virology, Aug. 2001, p. 7375-7383.
Park et al., 1991, "Rescue of a Foreign Gene by Sendai Virus", Proc. Natl. Acad. Sci. USA 88:5537-5541.
Parkin et al.. "Temperature Sensitive Mutants of Influenza A Virus Generated by Reverse Genetics . . . ". Vir. Res .• 46:31-44; (1996).
Parkin N. et al., "Genetically Engineered Live Atenuated Influenza A Virus Vaccine Candidates", J. Virol., pp. 2772-2778; (1997).
Peeters et al., 1999, "Rescue of Newcastle Disease Virus from Cloned cDNA: Evidence that Cleavability of the Fusion Protein is a Major Determinant for Virulence", J. Virol. 73:5001-5009.
Pekosz et al., 1999, "Reverse genetics of negative-strand RNA viruses: closing the circle", Proc Natl Acad Sci USA. 96(16):8804-6.

Percy et al., 1994, "Expression of a foreign protein by influenza A virus", J Virol 68(7):4486-92.
Perez, Daniel R. et al., "The Matrix 1 Protein of Influenza A Virus Inhibits the TransciptaseActivity of a Model Influenza Reporter Genome in Vivo", Article No. VY989318, Virology, 1998. vol. 249. pp. 52-61.
Perkin N. et al., "Genetically Engineered live Atenuated Influenza A Virus Vaccine Candidates", J. ViraL, pp. 2772-2778; (1997).
Pleschka et al., 1996, "A Plasmid-Based Reverse Genetics System for Influenza A Virus", J. Virol. 70:4188-4192.
Qiu et. al.. 1994, "The influenza virus NS1 protein is a poly(A)-binding protein that inhibits nuclear export of mRNAs containing poly(A)", J Virol. 68(4):2425-32.
Qiu et.al., 1995. the influenza virus NS1 protein binds to a specific region in human U6 snRNA and inhibits U6-U2 and U6-U4 snRNA . . . , RNA 1:304-16.
Racaniello et aL. 1981. "Cloned Poliovirus Complementary DNA is Infectious in Mammalian Cells", Science 214:916-919.
Radecke et al. 1995, "Rescue of measles viruses from cloned DNA". EMBO J. 14(23):5773-84.
Radecke et al.. "Reverse Genetics Meets the Nonsegmented Negative-Strand RNA Viruses", Medical Virology. vol. 7: 49-63 (1997).
Roberts and Rose. 1998. "Recovery of Negative-Strand RNA Viruses from Plasmid DNAs: a Positive Approach Revitalizes a Negative Field", Virol. 247:1-6.
Rocha et al., Comparison of 10 influenza A (H1 N1 and H3N2) haemagglutinin sequences obtained directly from clinical specimens to those of MOCK cell- and egg-grown viruses, 1993, Joumal of General Virology, vol. 74, pp. 2513-2518.
Rogers G N et al: "Single Amino-Acid Substitutions in Influenza Hem Agglutinin Change Receptor Binding Specificity", Nature (London), vol. 304, No. 5921, 1983, pp. 76-78.
Rose et al., 1996, "Positive Strands to the Rescue Again: . . . " PNAS USA 94:14998-15000.
Schickli et al., "Plasmid-only rescue of influenza A virus vaccine candidates," Philosophical Transactions of the Royal Society of London. Series B. Biological Sciences (London), 2001, 356:1965-1973.
Schlesinger et al., 1995. "RNA viruses as vectors for the expression of heterologous proteins", Mol Biotechnol. 3(2):155-165.
Schlicki et al., Plasmid-only rescue of influenza A virus vaccine candidates, Philosophical Transactions of the Royal Society of London Series S, 2001, vol. 356, p. 1965-1973.
Schnell et al.. 1994. "Infectious Rabies Viruses from Cloned eDNA", EMBO J. 13:4195-4203.
Scholtissek, et al., "The Nucleoprotein as a Possible Major Factor in Determining Host Specificity of Influenza H3N2 Viruses," Virology, 1985; 147:287-294.
Seong et al.. 1992. A new method for reconstituting influenza polymerase and RNA in vitro: a study of the promoter elements for cRNA and vRNA synthesis in vitro and viral rescue in vivo. Virology. 166(1):247-260.
Sidhu et al., 1995, "Rescue of synthetic measles virus minireplicons: measles genomic termini direct efficient expression and propagation of a reporter gene". Virology, 208(2):600-607.
Snyder et al., Four Viral Genes Independently Contribute to Attenuation of Live Influenza AIAnn Arbor/6/60 (H2N2) Cold-Adapted . . . J, Virol.. 62:488-95; (1988).
Stoeckle, "Segment-specific and common nucleotide sequences in the noncoding regions of influenza B virus genome RNAs," PNAS USA, 1987, vol. 84, No. 9, pp. 2703-2707.
Subbarao et al., The Attenuation Phenotype Conferred by the M Gene of the Influenza AIAnn Arbor/6/60 Cold-Adapted Virus (H2N2) on the . . . Virus. Res ., 25:37-50; (1992).
Subbarao et al., "Sequential Addition of Temperature-Sensitive Missense Mutations into the PB2 Gene of Influenza A Transfectanl . . . ". J. of Vir., Am. Society for Microbiology. Oct. 1995. pp. 5969-5977.
Subbarao, et al., "Rescue of a Influenza A Virus Wild-Type PB2 Gene and a Mutant Derivative Bearing a Site-Specific . . . " J. of Virology, 1993, pp. 7223-7228.
Subbarao, K., et al., "Evaluation of Genetically Modified Reassortant H5N1 Influenza A Virus Vaccine Candidate Generated by Plasmid-Based Reverse Genetics." Virology (2003) 305: 192-200.

(56) References Cited

OTHER PUBLICATIONS

Subrehmanyan et al., The Development of Double-Seeded and Mixed Cell Culture Systems for the Use in Diagnostic Virology, Archiv fur die desamte Virusforschung, 1974, vol. 44. pp. 291-297.
Supplementary European Search Report mailed on: Dec. 11, 2007 in European Patent Application No. EP03724208.8 filed on Apr. 25, 2003.
Supplementary European Search Report mailed on: Dec. 29, 2006 in European Patent Application No. EP0481407.6 filed on Dec. 22, 2004.
Supplementary Partial European Search Report mailed on: Apr. 1, 2009 in European Patent Application No. EP05750661.0 filed on May 20, 2005.
Supplementary Partial European Search Report mailed on: Sep. 24, 2007 in European Patent Application No. EP03724208.8 filed on Apr. 25, 2003.
Supplemetary Eurpoean Search Report mailed Dec. 29, 2006 in Eurpoean Application No. 04814807.6 filed on Dec. 22, 2004.
Szewczyk et al., 1988, •Purification, Thioredoxin Renaturation, and Reconstituted Activity of the Three Subunits of the Influenza A Virus RNA Polymerase. Proc. Nat. Acad. Sci. USA 85:7907-7911.
Taylor et al., 1990, "Newcastle Disease Virus Fusion Protein Expressed in a Fowlpox Virus Recombinant Confers Protection in ChiCkens", J. Viral. 64:1441-1450.
Treanor et al., "Evaluation of the Genetic Stability of the Temperature-Sensitive PB2 Gene Mutation of the Influenza A/Ann Arbor/6/60 Cold-Adapted Vaccine Virus," Journal of Virology Dec. 1994, p. 7684-7688.
Verhoeyen, "Complete nucleotide sequence of the influenza B/Singapore/222/79 virus hemagglutinin gene and comparison with the B/Lee/40 hemagglutinin" Nucleic Acids Res., 1983, vol. 11, No. 14, pp. 4703-4712.
Wang et al. Extensive Hetergeneity in the Hemagglutinin of Egg-Grown Influenza Viruses from different Patients, 1989, Virology, vol. 171, p. 275-279.
Ward et al., 1988, "Direct Measurement of the Poliovirus RNA Polymerase Error Frequency in Vitro", J. Virol. 62:558-562.
Wareing at al., 2001. Immunogenic and Isotype-Specific Responses to Russian and US Cold-Adapted Influenza A Vaccine Donor Strains . . . , J of Medical Virology 65:171-177.
Wareing, M. D., et al. "Preparation and Characterisation of Attenuated Cold-Adapted Influenza A Reassortants Derived from the AlLeningradl134117/57 Donor Strain." Vaccine (2002) 20: 2082-90.
Webby et al., 2004, "Responsiveness to a pandemic alert: use of reverse genetics for rapid development of influenza vaccines", Lancet 363:1099-1103.
Whelan et al., 1995, "Effiecient recovery of infectious vesicular stomatitis virus entirely from cDNA clones", Proc.Natl.Acad.Sci. USA 92: 8388-8392.
Xu et al., 1995 #AAB06964 (abstract only).
Xu et al., 1996, "Genetic Variation in Neuraminidase Genes of Influenza A (H3N2) Viruses", Virology 224:175-183.
Xu, Xiyan et al., "Genetic Characterization of the Pathogenic Influenza A/Goose/Guandong/1/96 (H5N1) Virus: Similarly of its Hemagglutinin Gene to Those of H5N1 Viruses form the 1997 Outbreaks in Hong Kong", Article 10 viro. 1999.9820, Virology, 1999, vol. 261, pp. 15-19.
Yamanaka et al.. "In vivo analysis of the promoter structure of the influenza virus RNA genome using a transfection system with an engineered RNA." Proc Nail Aced Sci USA 88: 5369-5373. 1991.
Yu et al., 1995, "Functional coNA clones of the human respiratory syncytial (RS) virus N, P, and L proteins support replication RS virus genomic RNA analogs and define minimal trans-acting requirements for RNA replication", J Virol. 69(4):2412-9.
Yusoff et al.. 1987, "Nucleotide Sequence Analysis of the L Gene of Newcastle Disease Virus: Homologies with Sendi and Vesicular Stomatitis Viruses" Nucleic Acids Res. 15: 3961-3976.
Zaghouani el al., 1991, "Induction of antibodies to the envelope protein of the human immunodeficiency virus by Immunization with monoclonal anti-idlotypes", Proc. Natl. Acad. Sci. USA 88:5645-5649.
Zaghouani et al., 1992. "Cells Expressing an H Chain to Gene Carrying a Viral T Cell Epitope Are Lysed by Specific Cytolytic T Cells", J. Immunol. 148:3604-3609.
Zambon et al., The Pathogenesis of Influenza in Humans, Reviews in Medical Virology, Jul.-Aug. 2001, vol. 11, No. 4, pp. 227-241.
Zhang and Air, 1994, "Expression of Functional Influenza Virus A Polymerase Proteins and Template from Cloned cDNAs in Recombinant Vaccinia Virus Infected Cells", Biochem. Biophys. Res. Commun. 200:95-101.
Zhang et al.. Persistence of four related human munodeficiency virus subtypes during the course of zidovudine therapy . . . J. Virol. 1994 66: 425-432.
Zhou, Yan, et al., "Membrane-Anchored Incorporation of a Foreign Protein in Recombinant Influenza Virions", Article No. VY989169, Virology, 1998, vol. 246, pp. 83-94.
Zobel et aL, 1993, "RNA polymerase I catalysed transcription of insert viral cDNA", Nucleic Acids Res. 21 (16):3607-14.
Extended European Search Report mailed on Sep. 2, 2013 in European Patent Application No. 13159978.9, filed on May 20, 2005.
Office Action mailed on: Jun. 20, 2008 in U.S. Appl. No. 11/018,624, filed Dec. 22, 2004 and published as: 2005-0158342 on: Jul. 21, 2005, now abandoned.
Office Action mailed on: Sep. 24, 2007 in U.S. Appl. No. 11/018,624, filed Dec. 22, 2004 and published as: 2005-0158342 on: Jul. 21, 2005, now abandoned.
Office Action mailed on: Feb. 2, 2007 in U.S. Appl. No. 11/018,624, filed Dec. 22, 2004 and published as: 2005-0158342 on: Jul. 21, 2005, now abandoned.
Office Action mailed on: Jun. 13, 2006 in U.S. Appl. No. 11/018,624, filed Dec. 22, 2004 and published as: 2005-0158342 on: Jul. 21, 2005, now abandoned.
Office Action mailed on: Apr. 28, 2006 in U.S. Appl. No. 11/018,624, filed Dec. 22, 2004 and published as: 2005-0158342 on: Jul. 21, 2005, now abandoned.
Office Action mailed on: May 18, 2010 in U.S. Appl. No. 12/336,158, filed Dec. 16, 2008 and published as: 2009-0208527 on: Aug. 20, 2009.
Office Action mailed on: Jun. 1, 2010 in U.S. Appl. No. 12/336,158, filed Dec. 16, 2008 and published as: 2009-0208527 on: Aug. 20, 2009.
Office Action mailed on:Nov. 8, 2010 in U.S. Appl. No. 12/336,158, filed Dec. 16, 2008 and published as: 2009-0208527 on: Aug. 20, 2009.
Office Action mailed on: May 18, 2011 in U.S. Appl. No. 12/336,158, filed Dec. 16, 2008 and published as: 2009-0208527 on: Aug. 20, 2009.
Office Action mailed on: Sep. 8, 2011 in U.S. Appl. No. 12/336,158, filed Dec. 16, 2008 and published as: 2009-0208527 on: Aug. 20, 2009.
Office Action mailed on: Nov. 30, 2012 in U.S. Appl. No. 13/309,498, filed Dec. 1, 2011 and published as: on:.
Office Action mailed on: Aug. 6, 2012 in U.S. Appl. No. 13/309,498, filed Dec. 1, 2011 and published as: on:.
Office Action mailed on: Jul. 22, 2008 in U.S. Appl. No. 11/133,345, filed May 20, 2005 and published as: 2005-0266026 on: Dec. 1, 2005, and issued as 7,465,456 on Dec. 16, 2008.
Office Action mailed on: Aug. 20, 2007 in U.S. Appl. No. 11/133,345, filed May 20, 2005 and published as: 2005-0266026 on: Dec. 1, 2005, and issued as 7,465,456 on Dec. 16, 2008.
Office Action mailed on: Nov. 27, 2006 in U.S. Appl. No. 11/133,345, filed May 20, 2005 and published as: 2005-0266026 on: Dec. 1, 2005, and issued as 7,465,456 on Dec. 16, 2008.
Office Action mailed on: Aug. 8, 2006 in U.S. Appl. No. 11/133,345, filed May 20, 2005 and published as: 2005-0266026 on: Dec. 1, 2005, and issued as 7,465,456 on Dec. 16, 2008.
Office Action mailed on: Jun. 28, 2013 in U.S. Appl. No. 13/296,933, filed Nov. 15, 2011 and published as: 2012-0288521 on: Nov. 15, 2012.

(56) References Cited

OTHER PUBLICATIONS

Office Action mailed on: Feb. 7, 2013 in U.S. Appl. No. 13/296,933, filed Nov. 15, 2011 and published as: 2012-0288521 on: Nov. 15, 2012.
Office Action mailed on: Oct. 24, 2012 in U.S. Appl. No. 13/296,933, filed Nov. 15, 2011 and published as: 2012-0288521 on: Nov. 15, 2012.
Office Action mailed on: Aug. 25, 2011 in U.S. Appl. No. 12/254,131, filed Oct. 20, 2008 and published as: 2009-0175907 on: Jul. 9, 2009 and issued as: 8,114,415 on Feb. 14, 2012.
Office Action mailed on: Apr. 21, 2011 in U.S. Appl. No. 12/254,131, filed Oct. 20, 2008 and published as: 2009-0175907 on: Jul. 9, 2009 and issued as: 8,114,415 on Feb. 14, 2012.
Office Action mailed on:Aug. 19, 2010 in U.S. Appl. No. 12/254,131, filed Oct. 20, 2008 and published as: 2009-0175907 on: Jul. 9, 2009 and issued as: 8,114,415 on Feb. 14, 2012.
Office Action mailed on: Mar. 23, 2010 in U.S. Appl. No. 12/254,131, filed Oct. 20, 2008 and published as: 2009-0175907 on: Jul. 9, 2009 and issued as: 8,114,415 on Feb. 14, 2012.
Office Action mailed on: Nov. 28, 2012 in U.S. Appl. No. 13/214,110, filed Aug. 19, 2011 and published as: 2012-0020997 on: Jan. 26, 2012.
Office Action mailed on: Jun. 11, 2012 in U.S. Appl. No. 13/214,110, filed Aug. 19, 2011 and published as: 2012-0020997 on: Jan. 26, 2012.
Office Action mailed on: Jul. 15, 2011 in U.S. Appl. No. 10/423,828, filed Apr. 25, 2003 and published as: 2004-0029251 on: Feb. 12, 2004 and issued as: 8,012,736 on Sep. 6, 2011.
Office Action mailed on: Jul. 5, 2011 in U.S. Appl. No. 10/423,828 filed, Apr. 25, 2003 and published as: 2004-0029251 on: Feb. 12, 2004 and issued as: 8,012,736 on Sep. 6, 2011.
Office Action mailed on: Oct. 13, 2010 in U.S. Appl. No. 10/423,828, filed Apr. 25, 2003 and published as: 2004-0029251 on: Feb. 12, 2004 and issued as: 8,012,736 on Sep. 6, 2011.
Office Action mailed on:Feb. 5, 2010 in U.S. Appl. No. 10/423,828, filed Apr. 25, 2003 and published as: 2004-0029251 on: Feb. 12, 2004 and issued as: 8,012,736 on Sep. 6, 2011.
Office Action mailed on:Dec. 8, 2008 in U.S. Appl. No. 10/423,828, filed Apr. 25, 2003 and published as: 2004-0029251 on: Feb. 12, 2004 and issued as: 8,012,736 on Sep. 6, 2011.
Office Action mailed on: Mar. 26, 2008 in U.S. Appl. No. 10/423,828, filed Apr. 25, 2003 and published as: 2004-0029251 on: Feb. 12, 2004 and issued as: 8,012,736 on Sep. 6, 2011.
Office Action mailed on: Jun. 11, 2007 in U.S. Appl. No. 10/423,828, filed Apr. 25, 2003 and published as: 2004-0029251 on: Feb. 12, 2004 and issued as: 8,012,736 on Sep. 6, 2011.
Office Action mailed on: Sep. 22, 2006 in U.S. Appl. No. 10/423,828, filed Apr. 25, 2003 and published as: 2004-0029251 on: Feb. 12, 2004 and issued as: 8,012,736 on Sep. 6, 2011.
Office Action mailed on: Feb. 7, 2006 in U.S. Appl. No. 10/423,828, filed Apr. 25, 2003 and published as: 2004-0029251 on: Feb. 12, 2004 and issued as: 8,012,736 on Sep. 6, 2011.
Extended European Search Report mailed on Nov. 15, 2013 in European Patent Application No. 13170051.0, filed on Jun. 18, 2008 and published as EP 2 674 486 on Dec. 18, 2013.
Office Action dated Oct. 25, 2013 in U.S. Appl. No. 12/599,761, filed Sep. 10, 2010 and published as US 2010-0322969 on Dec. 23, 2010.
Office Action mailed on: Jun. 10, 2013 in U.S. Appl. No. 12/599,761, filed Sep. 10, 2010 and published as: 2010-0322969 on: Dec. 23, 2010.
Office Action mailed on: Nov. 21, 2012 in U.S. Appl. No. 12/599,761, filed Sep. 10, 2010 and published as: 2010-0322969 on: Dec. 23, 2010.
Office Action dated Dec. 23, 2013 in U.S. Appl. No. 13/214,110, filed Aug. 19, 2011 and published as US 2012-0020997 on Jan. 26, 2012.
Office Action dated Sep. 8, 2014 in U.S. Appl. No. 13/779,549, filed Feb. 27, 2013 and published as US 2013-0189762 on Jul. 25, 2013.
Donabedian et al., "Genetics of cold-adapted B/Ann Arbor/1/66 influenza virus reassortants: the acidic polymerase (PA) protein gene confers temperature sensitivity and attenuated virulence" Microb. Pathog. (1987) 3(2):97-108.
Office Action dated Dec. 24, 2014 in U.S. Appl. No. 13/779,549, filed Feb. 27, 2013 and published as US 2013-0189762 on Jul. 25, 2013.
Office Action dated Jan. 16, 2015 in U.S. Appl. No. 14/222,461, filed Mar. 21, 2014 and published as US 2014-0220075 on Aug. 7, 2014.

* cited by examiner

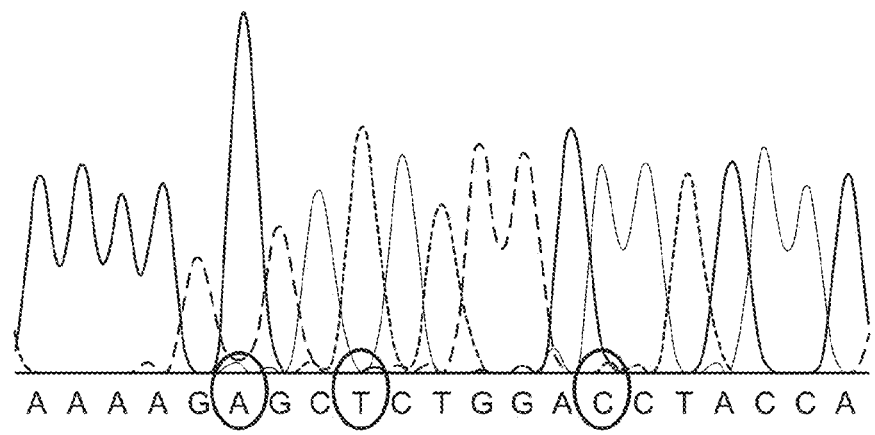
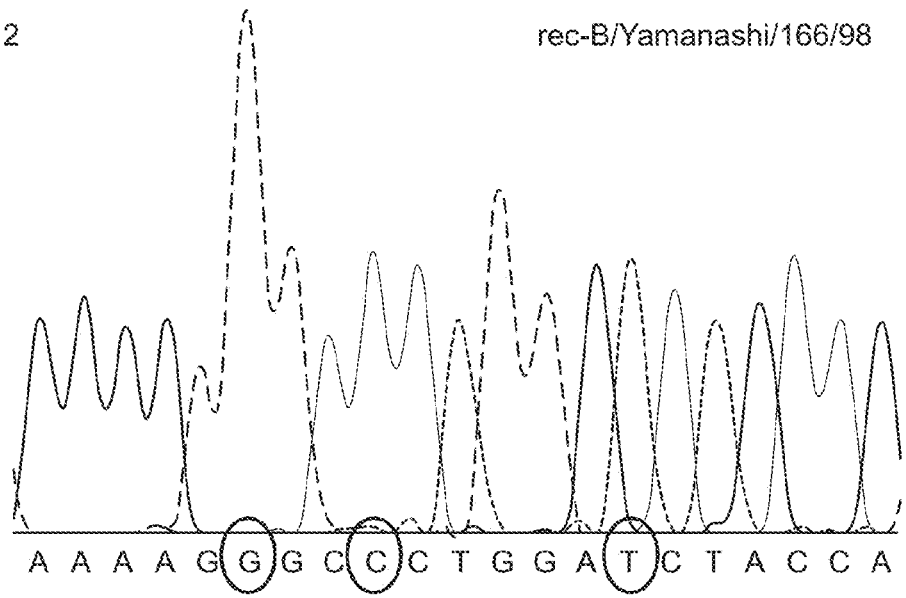
FIG. 3D

```
LOCUS       pAD3000      2836 bp    DNA    circular      14-JAN-2002
DEFINITION  Derivative of pHW2000 with SV40 PolyA Signal replacing BGH FEATURES             Location/Qualifiers
     promoter        2420..2799
                     /vntifkey="29"
                     /label=pCMV
                     /note="truncated CMV promoter (corresponding to 484-863
region of pcDNA3)"
     misc_marker     1422..2282
                     /vntifkey="22"
                     /label=bla
                     /note="beta lactamase"
     rep_origin      612..1172
                     /vntifkey="33"
                     /label=Col\E1ori
                     /note="Col E1 replication origin"
     terminator      11..45
                     /vntifkey="43"
                     /label=tI
                     /note="Pol I terminator"
     promoter        complement(65..276)
                     /vntifkey="29"
                     /label=PolI
                     /note="Human Pol I Promoter"
     exon            296..430
                     /vntifkey="61"
                     /label=pA
                     /note="pA(SV40)"
BASE COUNT      717 a      734 c      703 g      682 t
ORIGIN
        1 ctagcagtta accggagtac tggtcgacct ccgaagttgg gggggaggag acggtaccgt
       61 ctccaataac cggcggccc aaaatgccga ctcggagcga agatatacc tccccggg
      121 ccgggaggtc gcgtcaccga ccacgcgcc ggccaggcg acgcgcgaca cggacacctg
      181 tcccaaaaaa cgccaccatc gcagccacac acggacgcgcc cggggccctc tggtcaaccc
      241 caggacacac gcgggagcag cgccgggccg gggacgccct cccggcggtc acctcagaca
      301 tgataagata cattgatgag tttggacaaa ccacaactag aatgcagtga aaaaaatgct
      361 ttatttgtga aattgtgat gctattgctt tatttgtaac cattataagc tgcaataaac
      421 aaggatctgc attaatgaat cggccaacgc gcggggagag cggtttgcg tattgggcgc
      481 tcttccgctt cctcgctcac tgactcgctg cgctcggtcg ttcggctgcg gcgagcggta
      541 tcagctcact caaaggcggt aatacggtta tccacagaat caggggataa cgcaggaaag
      601 aacatgtgag caaaaggcca gcaaaaggcc aggaaccgta aaaaggccgc gttgctggcg
      661 ttttttccata ggctccgccc cctgacgag catcacaaaa atcgacgctc aagtcagagg
      721 tggcgaaacc cgacaggact ataaagatac caggcgttc ccctggaag ctccctcgtg
      781 cgctctcctg ttccgaccct gccgcttacc ggatacctgt ccgcctttct cccttcggga
      841 agcgtggcgc tttctcaatg ctcacgctgt aggtatctca gttcggtgta ggtcgttcgc
      901 tccaagctgg gctgtgtgca cgaaccccc gttcagcccg accgctgcgc cttatccggt
      961 aactatcgtc ttgagtccaa cccggtaaga cgacttatcg ccactggc agcagccact
     1021 ggtaacagga ttagcagagc gaggtatgta ggcggtgcta cagagttctt gaagtggtgg
     1081 cctaactacg gctacactag aaggacagta tttggtatct gcgctctgct gaagccagtt
     1141 accttcggaa aaagagttgg tagctcttga tccggcaaac aaaccaccgc tggtagcggt
     1201 ggtttttttg tttgcaagca gcagattacg cgcagaaaaa aaggatctca agaagatcct
     1261 ttgatctttt ctacggggtc tgacgctcag tggaacgaaa actcacgtta agggattttg
     1321 gtcatgagat tatcaaaaag gatcttcacc tagatccttt taaattaaaa atgaagtttt
```

Fig. 4A

```
1381 aaatcaatct aaagtatata tgagtaaact tggtctgaca gttaccaatg cttaatcagt
1441 gaggcaccta tctcagcgat ctgtctattt cgttcatcca tagttgcctg actccccgtc
1501 gtgtagataa ctacgatacg ggagggctta ccatctggcc ccagtgctgc aatgataccg
1561 cgagacccac gctcacggc tccagattta tcagcaataa accagccagc cggaagggcc
1621 gagcgcagaa gtggtcctgc aactttatcc gcctccatcc agtctattaa ttgttgccgg
1681 gaagctagag taagtagttc gccagttaat agtttgcgca acgttgttgc cattgctaca
1741 ggcatcgtgg tgtcacgctc gtcgtttggt atggcttcat tcagctccgg ttcccaacga
1801 tcaaggcgag ttacatgatc ccccatgttg tgcaaaaaag cggttagctc cttcggtcct
1861 ccgatcgttg tcagaagtaa gttggccgca gtgttatcac tcatggttat ggcagcactg
1921 cataattctc ttactgtcat gccatccgta agatgctttt ctgtgactgg tgagtactca
1981 accaagtcat tctgagaata gtgtatgcgg cgaccgagtt gctcttgccc ggcgtcaata
2041 cgggataata ccgcgccaca tagcagaact ttaaaagtgc tcatcattgg aaaacgttct
2101 tcggggcgaa aactctcaag gatcttaccg ctgttgagat ccagttcgat gtaacccact
2161 cgtgcaccca actgatcttc agcatctttt actttcacca gcgtttctgg gtgagcaaaa
2221 acaggaaggc aaaatgccgc aaaaaaggga taagggcga cacggaaatg ttgaatactc
2281 atactcttcc ttttttcaata ttattgaagc atttatcagg gttattgtct catgagcgga
2341 tacatatttg aatgtattta gaaaaataaa caaatagggg ttccgcgcac atttccccga
2401 aaagtgccac ctgacgtcga tatgccaagt acgccccta ttgacgtcaa tgacggtaaa
2461 tggcccgcct ggcattatgc ccagtacatg accttatggg actttcctac ttggcagtac
2521 atctacgtat tagtcatcgc tattaccatg gtgatgcggt tttggcagta catcaatggg
2581 cgtggatagc ggtttgactc acggggattt ccaagtctcc accccattga cgtcaatggg
2641 agtttgtttt ggcaccaaaa tcaacgggac tttccaaaat gtcgtaacaa ctccgcccca
2701 ttgacgcaaa tgggcggtag gcgtgtacgg tgggaggtct atataagcag agctctctgg
2761 ctaactagag aacccactgc ttactggctt atcgaaatta atacgactca ctatagggag
2821 acccaagctg ttaacg
```

```
                        *        20         *        40         *
pAB121-PB1 : ..................................................  :  50
MDV-B-PB1  : ..................................................  :  50
             AGCAGAAGCGGAGCCTTTAAGATGAATATAAATCCTTATTTTCTCTTCAT

60         *        80         *       100
pAB121-PB1 : ..................................................  : 100
MDV-B-PB1  : ..................................................  : 100
             AGATGTACCCATACAGGCAGCAATTTCAACAACATTCCCATACACCGGTG

*       120         *       140         *
pAB121-PB1 : ..................................................  : 150
MDV-B-PB1  : ..................................................  : 150
             TTCCCCCTTATTCCCATGGA

```
              *         520         *         540         *
pAB121-PB1 : ............................................... : 550
MDV-B-PB1  : ............................................... : 550
             GGGTGGATTAGTACCCTTTTGCCAAGATATCATTGATTCATTGGAC

```
pAB121-PB1 : .................................................. : 1100
MDV-B-PB1  : .................................................. : 1100
             TTCTCCAATAAAATAGCCAGATTGGGAAAAGGGTTCATGATAACAAGCAA

*         1120         *         1140         *
pAB121-PB1 : .................................................. : 1150
MDV-B-PB1  : .................................................. : 1150
             AACAAAAAGACTGAAGGCTCAAATACCTTGTCCCGATCTGTTTAATATAC

1160         *         1180         *         1200
pAB121-PB1 : .................................................. : 1200
MDV-B-PB1  : .................................................. : 1200
             CATTAGAAAGATATAATGAAGAAACAAGGGCAAAATTAAAAAAGCTGAAA

*         1220         *         1240         *
pAB121-PB1 : .................................................. : 1250
MDV-B-PB1  : .................................................. : 1250
             CCATTCTTCAATGAAGAAGGAACGGCATCTTTGTCGCCTGGGATGATGAT

1260         *         1280         *         1300
pAB121-PB1 : .................................................. : 1300
MDV-B-PB1  : .................................................. : 1300
             GGGAATGTTTAATATGCTATCTACCGTGTTGGGAGTAGCCGCACTAGGGA

*         1320         *         1340         *
pAB121-PB1 : .................................................. : 1350
MDV-B-PB1  : .................................................. : 1350
             TCAAAAACATTGGAAACAAAGAATACTTATGGGATGGACTGCAATCTTCT

1360         *         1380         *         1400
pAB121-PB1 : .................................................. : 1400
MDV-B-PB1  : .................................................. : 1400
             GATGATTTTGCTCTGTTTGTTAATGCAAAAGATGAAGAGACATGTATGGA

*         1420         *         1440         *
pAB121-PB1 : .................................................. : 1450
MDV-B-PB1  : .................................................. : 1450
             AGGAATAAACGATTTTTACCGAACATGTAAGCTATTGGGAATAAACATGA

1460         *         1480         *         1500
pAB121-PB1 : .................................................. : 1500
MDV-B-PB1  : .................................................. : 1500
             GCAAAAAGAAAAGTTACTGTAATGAAACTGGAATGTTTGAATTTACAAGC

*         1520         *         1540         *
pAB121-PB1 : .................................................. : 1550
MDV-B-PB1  : .................................................. : 1550
             ATGTTCTACAGAGATGGATTTGTATCTAATTTTGCAATGGAACTTCCTTC

1560         *         1580         *         1600
pAB121-PB1 : .................................................. : 1600
MDV-B-PB1  : .................................................. : 1600
             ATTTGGAGTTGCTGGAGTAAATGAATCAGCAGATATGGCAATAGGAATGA
```

Fig. 5C

```
                    *         1620          *         1640          *
pAB121-PB1 : ................................................... : 1650
MDV-B-PB1  : ................................................... : 1650
             CAATAATAAAGAACAATATGATCAACAATGGGATGGGTCCAGCAACAGCA

1660          *         1680          *         1700
pAB121-PB1 : ................................................... : 1700
MDV-B-PB1  : ................................................... : 1700
             CAAACAGCCATACAATTATTCATAGCTGATTATAGATACACCTACAAATG

*         1720          *         1740          *
pAB121-PB1 : T................................................. : 1750
MDV-B-PB1  : ................................................... : 1750
             CCACAGGGGAGATTCCAAAGTGGAAGGAAAGAGAATGAAAATTATAAAGG

1760          *         1780          *         1800
pAB121-PB1 : ................................................... : 1800
MDV-B-PB1  : ................................................... : 1800
             AGCTATGGGAAAACACTAAAGCAAGAGATGGTCTGTTAGTAGCAGATGGT

*         1820          *         1840          *
pAB121-PB1 : ................................................... : 1850
MDV-B-PB1  : ................................................... : 1850
             GGGCCTAACATTTACAATTTGAGAAACTTGCATATCCCAGAAATAGTATT

1860          *         1880          *         1900
pAB121-PB1 : ................................................... : 1900
MDV-B-PB1  : ................................................... : 1900
             AAAGTACAACCTAATGGACCCTGAATACAAAGGGCGGTTACTGCATCCTC

*         1920          *         1940          *
pAB121-PB1 : ................................................... : 1950
MDV-B-PB1  : ................................................... : 1950
             AAAATCCCTTTGTAGGACATTTGTCTATTGAGGGCATCAAAGAGGCAGAT

1960          *         1980          *         2000
pAB121-PB1 : ................................................... : 2000
MDV-B-PB1  : ................................................... : 2000
             ATAACCCCAGCACATGGTCCAGTAAAGAAAATGGACTATGATGCGGTATC

*         2020          *         2040          *
pAB121-PB1 : ................................................... : 2050
MDV-B-PB1  : ................................................... : 2050
             TGGAACTCATAGTTGGAGAACCAAAAGGAACAGATCTATACTAAACACTG

2060          *         2080          *         2100
pAB121-PB1 : ................................................... : 2100
MDV-B-PB1  : ................................................... : 2100
             ATCAGAGGAACATGATTCTTGAGGAACAATGCTACGCTAAGTGTTGCAAC

*         2120          *         2140          *
pAB121-PB1 : ................................................... : 2150
MDV-B-PB1  : ................................................... : 2150
             CTTTTTGAGGCCTGTTTTAACAGTGCATCATACAGGAAACCAGTAGGTCA

```
pAB121-PB1 : ..................................................... : 2200
MDV-B-PB1  : ..................................................... : 2200
             GCACAGCATGCTTGAGGCTATGGCCCACAGATTAAGAATGGATGCACGAC

*         2220        *         2240        *
pAB121-PB1 : ..................................................... : 2250
MDV-B-PB1  : ..................................................... : 2250
             TAGATTATGAATCAGGAAGAATGTCAAAGGATGATTTTGAGAAAGCAATG

2260         *         2280        *         2300
pAB121-PB1 : ..................................................... : 2300
MDV-B-PB1  : ..................................................... : 2300
             GCTCACCTTGGTGAGATTGGGTACATATAAGCTTCGAAGATGTCTATGGG

*         2320        *         2340        *
pAB121-PB1 : ..................................................... : 2350
MDV-B-PB1  : ..................................................... : 2350
             GTTATTGGTCATCATTGAATACATGCGGTACACAAATGATTAAAATGAAA 2360
pAB121-PB1 : ..................... : 2369
MDV-B-PB1  : ..................... : 2369
             AAAGGCTCGTGTTTCTACT
```

```
                    *        20         *        40         *
pAB122-PB2 : .................................................. :  50
MDV-B-PB2  : .................................................. :  50
             AGCAGAAGCGGAGCGTTTTCAAGATGACATTGGCCAAAATTGAATTGTTA

60         *        80         *       100
pAB122-PB2 : .................................................. : 100
MDV-B-PB2  : .................................................. : 100
             AAACAACTGTTAAGGGACAATGAAGCCAAAACGGTATTGAAACAAACAAC

*       120         *       140         *
pAB122-PB2 : .................................................. : 150
MDV-B-PB2  : .................................................. : 150
             GGTAGACCAATATAACATAATAAGAAAATTCAATACATCAAGAATTGAAA

160         *       180         *       200
pAB122-PB2 : .................................................. : 200
MDV-B-PB2  : .................................................. : 200
             AGAACCCTTCATTAAGGATGAAGTGGGCCATGTGTTCTAATTTTCCCTTG

*       220         *       240         *
pAB122-PB2 : .................................................. : 250
MDV-B-PB2  : .................................................. : 250
             GCTCTGACCAAGGGTGATATGGCAAATAGAATCCCCTTGGAATACAAGGG

260         *       280         *       300
pAB122-PB2 : .................................................. : 300
MDV-B-PB2  : .................................................. : 300
             AATACAACTTAAAACAAATGCTGAAGACATAGGAACCAAAGGCCAAATGT

*       320         *       340         *
pAB122-PB2 : .................................................. : 350
MDV-B-PB2  : .................................................. : 350
             GCTCAATAGCAGCAGTTACCTGGTGGAATACATATGGACCAATAGGAGAT

360         *       380         *       400
pAB122-PB2 : .................................................. : 400
MDV-B-PB2  : .................................................. : 400
             ACTGAAGGTTTCGAAAAGGTCTACGAAAGCTTTTTTCTCAGAAAGATGAG

*       420         *       440         *
pAB122-PB2 : .................................................. : 450
MDV-B-PB2  : .................................................. : 450
             ACTTGACAATGCCACTTGGGGCCGAATAACTTTTGGCCCAGTTGAAAGAG

460         *       480         *       500
pAB122-PB2 : .................................................. : 500
MDV-B-PB2  : .................................................. : 500
             TGAGAAAAAGGGTACTGCTAAACCCTCTCACCAAGGAAATGCCTCCAGAT

*       520         *       540         *
pAB122-PB2 : .................................................. : 550
MDV-B-PB2  : .................................................. : 550
             GAAGCGAGCAATGTGATAATGGAAATATTGTTCCCTAAGAAGCAGGAAT

```
pAB122-PB2  : ................................................ : 600
MDV-B-PB2   : ................................................ : 600
              ACCAAGAGAATCTACTTGGATACATAGGGAACTGATAAAAGAAAAAGAG

*         620         *         640         *
pAB122-PB2  : ................................................ : 650
MDV-B-PB2   : ................................................ : 650
              AAAAATTGAAAGGAACGATGATAACTCCCATTGTACTGGCATACATGCTT

660         *         680         *         700
pAB122-PB2  : ................................................ : 700
MDV-B-PB2   : ................................................ : 700
              GAGAGAGAACTGCTTGCCCGAAGAAGGTTCCTGCCAGTCGCAGGAGCAAC

*         720         *         740         *
pAB122-PB2  : ................................................ : 750
MDV-B-PB2   : ................................................ : 750
              ATCAGCCGAGTTCATAGAAATGCTACACTGCTTACAAGGTGAAAATTGGA

760         *         780         *         800
pAB122-PB2  : ................................................ : 800
MDV-B-PB2   : ................................................ : 800
              GACAAATATATCACCCAGGAGGGAATAAACTAACTGAATCTAGGTCTCAA

*         820         *         840         *
pAB122-PB2  : ................................................ : 850
MDV-B-PB2   : ................................................ : 850
              TCAATGATTGTAGCTTGTAGAAAAATAATCAGAAGATCAATAGTCGCATC

860         *         880         *         900
pAB122-PB2  : ................................................ : 900
MDV-B-PB2   : ................................................ : 900
              AAACCCACTAGAGCTAGCTGTAGAAATTGCAAACAAGACTGTGATAGATA

*         920         *         940         *
pAB122-PB2  : ................................................ : 950
MDV-B-PB2   : ................................................ : 950
              CTGAACCTTTAAAATCATGTCTGGCAGCCATAGACGGAGGTGATGTAGCC

960         *         980         *        1000
pAB122-PB2  : ................................................ : 1000
MDV-B-PB2   : ................................................ : 1000
              TGTGACATAATAAGAGCTGCATTAGGACTAAAGATCAGACAAACACAAAG

*        1020         *        1040         *
pAB122-PB2  : ................................................ : 1050
MDV-B-PB2   : ................................................ : 1050
              ATTTGGACGGCTTGAACTAAAGAGAATATCAGGAAGAGGATTCAAAAATG

1060         *        1080         *        1100
pAB122-PB2  : ................................................ : 1100
MDV-B-PB2   : ................................................ : 1100
              ATGAAGAAATATTAATCGGGAACGGAACAATACAGAAAATTGGAATATGG
```

Fig. 5G

```
                         *         1120         *         1140         *
pAB122-PB2 : ................................................. : 1150
MDV-B-PB2  : ................................................. : 1150
             GACGGAGAAGAGGAGTTCCATGTAAGATGTGGTGAATGCAGGGGAATATT

1160         *         1180         *         1200
pAB122-PB2 : ................................................. : 1200
MDV-B-PB2  : ................................................. : 1200
             AAAAAAGAGCAAAATGACAATGGAAAAACTACTAATAAATTCAGCCAAAA

*         1220         *         1240         *
pAB122-PB2 : ................................................. : 1250
MDV-B-PB2  : ................................................. : 1250
             AGGAGGACATGAAAGATTTAATAATCTTGTGCATGGTATTTTCTCAAGAC

1260         *

```
pAB122-PB2 : ............................................... : 1700
MDV-B-PB2  : ............................................... : 1700
             CCAAAGAACTGGTGCAAAACACCTACCAATGGGTGCTAAAAAATTTGGTA

*        1720         *        1740         *
pAB122-PB2 : ............................................... : 1750
MDV-B-PB2  : ............................................... : 1750
             ACACTGAAGGCTCAGTTTCTTCTGGGAAAAGAAGACATGTTCCAATGGGA

1760        *        1780         *       1800
pAB122-PB2 : ............................................... : 1800
MDV-B-PB2  : ............................................... : 1800
             TGCATTTGAAGCATTTGAAAGCATAATCCCCCAGAAGATGGCTGGCCAGT

*        1820         *        1840         *
pAB122-PB2 : ............................................... : 1850
MDV-B-PB2  : ............................................... : 1850
             ACAGTGGATTTGCAAGAGCAGTGCTCAAACAAATGAGAGACCAAGAGGTT

1860        *        1880         *       1900
pAB122-PB2 : ............................................... : 1900
MDV-B-PB2  : ............................................... : 1900
             ATGAAAACTGACCAGTTCATAAAGTTGTTGCCTTTCTGTTTCTCACCACC

*        1920         *        1940         *
pAB122-PB2 : ............................................... : 1950
MDV-B-PB2  : ............................................... : 1950
             AAAATTAAGGAGAAATGGGGAGCCTTATCAATTCTTGAGGCTTATGTTGA

1960        *        1980         *       2000
pAB122-PB2 : ............................................... : 2000
MDV-B-PB2  : ............................................... : 2000
             AGGGAGGAGGGGAAAATTTCATCGAAGTAAGGAAAGGGTCCCTCTATTC

*        2020         *        2040         *
pAB122-PB2 : ............................................... : 2050
MDV-B-PB2  : ............................................... : 2050
             TCCTACAATCCACAAACAGAAGTCCTAACTATATGCGGCAGAATGATGTC

2060        *        2080         *       2100
pAB122-PB2 : ............................................... : 2100
MDV-B-PB2  : ............................................... : 2100
             ATTAAAAGGAAAAATTGAAGATGAAGAAAGGAATAGATCAATGGGGAATG

*        2120         *        2140         *
pAB122-PB2 : ............................................... : 2150
MDV-B-PB2  : ............................................... : 2150
             CAGTATTGGCAGGCTTTCTCGTTAGTGGCAAGTATGACCCAGATCTTGGA

2160        *        2180         *       2200
pAB122-PB2 : ............................................... : 2200
MDV-B-PB2  : ............................................... : 2200
             GATTTCAAAACTATTGAAGAACTTGAAAAGCTAAAACCGGGGGAAAAAGC
```

Fig. 5I

```
              *      2220         *      2240         *
pAB122-PB2 : ................................................ : 2250
MDV-B-PB2  : ................................................ : 2250
             AAACATCTTACTTTATCAAGGAAAGCCCGTTAAAGTAGTTAAAAGGAAAA

2260         *      2280         *      2300
pAB122-PB2 : ................................................ : 2300
MDV-B-PB2  : ................................................ : 2300
             GATATAGTGCTTTATCCAATGACATTTCACAAGGAATTAAGAGACAAAGA

*      2320         *      2340         *
pAB122-PB2 : ................................................ : 2350
MDV-B-PB2  : ................................................ : 2350
             ATGACAGTTGAGTCCATGGGGTGGGCCTTGAGCTAATATAAATTTATCCA

2360         *      2380         *
pAB122-PB2 : .............................................. : 2396
MDV-B-PB2  : .............................................. : 2396
             TTAATTCAATAGACACAATTGAGTGAAAAATGCTCGTGTTTCTACT
```

```
                         *        20         *        40         *
pAB123-PA  : .................................................. :  50
MDV-B-PA   : .................................................. :  50
             AGCAGAAGCGGTGCGTTTGATTTGCCATAATGGATACTTTTATTACAAGA

60         *        80         *       100
pAB123-PA  : .................................................. : 100
MDV-B-PA   : .................................................. : 100
             AACTTCCAGACTACAATAATACAAAAGGCCAAAAACACAATGGCAGAATT

*       120         *       140         *
pAB123-PA  : .................................................. : 150
MDV-B-PA   : .................................................. : 150
             TAGTGAAGATCCTGAATTACAACCAGCAATGCTATTCAACATCTGCGTCC

160         *       180         *       200
pAB123-PA  : .................................................. : 200
MDV-B-PA   : .................................................. : 200
             ATCTGGAGGTCTGCTATGTAATAAGTGATATGAATTTTCTTGATGAAGAA

*       220         *       240         *
pAB123-PA  : .................................................. : 250
MDV-B-PA   : .................................................. : 250
             GGAAAAACATATACAGCATTAGAAGGACAAGGAAAAGAACAAAACTTGAG

260         *       280         *       300
pAB123-PA  : .................................................. : 300
MDV-B-PA   : .................................................. : 300
             ACCACAATATGAAGTGATTGAGGGAATGCCAAGAAACATAGCATGGATGG

*       320         *       340         *
pAB123-PA  : .................................................. : 350
MDV-B-PA   : .................................................. : 350
             TTCAAAGATCCTTAGCCCAAGAGCATGGAATAGAGACTCCAAGGTATCTG

360         *       380         *       400
pAB123-PA  : .................................................. : 400
MDV-B-PA   : .................................................. : 400
             GCTGATTTGTTCGATTATAAAACCAAGAGGTTTATAGAAGTTGGAATAAC

*       420         *       440         *
pAB123-PA  : .................................................. : 450
MDV-B-PA   : .................................................. : 450
             AAAGGGATTGGCTGACGATTACTTTTGGAAAAAGAAAGAAAAGCTGGGGA

460         *       480         *       500
pAB123-PA  : .................................................. : 500
MDV-B-PA   : .................................................. : 500
             ATAGCATGGAACTGATGATATTCAGCTACAATCAAGACTATTCGTTAAGT

*       520         *       540         *
pAB123-PA  : .................................................. : 550
MDV-B-PA   : .................................................. : 550
             AATGAATCCTCATTGGATGAGGAAGGAAAAGGGAGAGTGCTAAGCAGACT

560         *       580         *       600
pAB123-PA  : .................................................. : 600
```

Fig. 5K

```
MDV-B-PA    : .................................................. :  600
              CACAGAACTTCAGGCTGAGTTAAGTCTGAAAAATCTATGGCAAGTTCTCA

*         620         *         640         *
pAB123-PA   : .................................................. :  650
MDV-B-PA    : .................................................. :  650
              TAGGAGAAGAAGATATTGAAAAAGGAATTGACTTCAAACTTGGACAAACA

660         *         680         *        700
pAB123-PA   : .................................................. :  700
MDV-B-PA    : .................................................. :  700
              ATATCTAAACTAAGGGATATATCTGTTCCAGCTGGTTTCTCCAATTTTGA

*         720         *         740         *
pAB123-PA   : .................................................. :  750
MDV-B-PA    : .................................................. :  750
              AGGAATGAGGAGCTACATAGACAATATAGATCCTAAAGGAGCAATAGAGA

760         *         780         *        800
pAB123-PA   : .................................................. :  800
MDV-B-PA    : .................................................. :  800
              GAAATCTAGCAAGGATGTCTCCCTTAGTATCAGTTACACCTAAAAAGTTG

*         820         *         840         *
pAB123-PA   : .................................................. :  850
MDV-B-PA    : .................................................. :  850
              AAATGGGAGGACCTAAGACCAATAGGGCCTCACATTTACAACCATGAGCT

860         *         880         *        900
pAB123-PA   : .................................................. :  900
MDV-B-PA    : .................................................. :  900
              ACCAGAAGTTCCATATAATGCCTTTCTTCTAATGTCTGATGAGTTGGGGC

*         920         *         940         *
pAB123-PA   : .................................................. :  950
MDV-B-PA    : .................................................. :  950
              TGGCTAATATGACTCAAGGGAAGTCCAAGAAACCGAAGACCTTAGCCAAA

960         *         980         *       1000
pAB123-PA   : .................................................. : 1000
MDV-B-PA    : .................................................. : 1000
              GAATGTCTAGAAAAGTACTCAACACTACGGGATCAAACTGACCCAATATT

*        1020         *        1040         *
pAB123-PA   : .................................................. : 1050
MDV-B-PA    : .................................................. : 1050
              AATAATGAAAAGCGAAAAAGCTAACGAAAACTTCTTATGGAAGCTGTGGA

1060         *        1080         *       1100
pAB123-PA   : .................................................. : 1100
MDV-B-PA    : .................................................. : 1100
              GGGACTGTGTAAATACAATAAGTAATGAGGAAACAAGTAACGAATTACAG
```

Fig. 5L

```
                  *        1120         *        1140         *
pAB123-PA  : ............................................... : 1150
MDV-B-PA   : ............................................... : 1150
             AAAACCAATTATGCCAAGTGGGCCACAGGAGATGGATTAACATACCAGAA

1160         *        1180         *        1200
pAB123-PA  : ............................................... : 1200
MDV-B-PA   : ............................................... : 1200
             AATAATGAAAGAAGTAGCAATAGATGACGAAACAATGTACCAAGAAGAGC

*        1220         *        1240         *
pAB123-PA  : ............................................... : 1250
MDV-B-PA   : ............................................... : 1250
             CCAAAATACCTAACAAATGTAGAGTGGCTGCTTGGGTTCAAACAGAGATG

1260         *        1280         *        1300
pAB123-PA  : ............................................... : 1300
MDV-B-PA   : ............................................... : 1300
             AATCTATTGAGCACTCTGACAAGTAAAAGGGCCCTGGATCTACCAGAAAT

*        1320         *        1340         *
pAB123-PA  : ............................................... : 1350
MDV-B-PA   : ............................................... : 1350
             AGGGCCAGACGTAGCACCCATGGAGCATGTAGGGAGTGAAAGAAGGAAAT

1360         *        1380         *        1400
pAB123-PA  : ............................................... : 1400
MDV-B-PA   : ............................................... : 1400
             ACTTTGTTAATGAAATCAACTACTGTAAGGCCTCTACCGTTATGATGAAG

*        1420         *        1440         *
pAB123-PA  : ............................................... : 1450
MDV-B-PA   : ............................................... : 1450
             TATGTACTTTTTCACACTTCATTATTAAATGAAAGCAATGCCAGCATGGG

1460         *        1480         *        1500
pAB123-PA  : ............................................... : 1500
MDV-B-PA   : ............................................... : 1500
             AAAATATAAAGTAATACCAATAACCAACAGAGTAGTAAATGAAAAAGGAC

*        1520         *        1540         *
pAB123-PA  : ............................................... : 1550
MDV-B-PA   : ............................................... : 1550
             AAAGTTTTGACATGCTTCATGGTCTGGCGGTTAAAGGGCAATCTCATCTG

1560         *        1580         *        1600
pAB123-PA  : ............................................... : 1600
MDV-B-PA   : ............................................... : 1600
             AGGGGAGATACTGATGTTGTAACAGTTGTGACTTTCGAATTTAGTAGTAC

*        1620         *        1640         *
pAB123-PA  : ............................................... : 1650
MDV-B-PA   : ............................................... : 1650
             AGATCCCAGAGTGGACTCAGGAAAGTGGCCAAAATATACTGTATTTAGAA

```
pAB123-PA : .................................................. : 1700
MDV-B-PA  : .................................................. : 1700
            TTGGCTCCTTATTTGTGAGTGGAAGGGAAAAATCTGTGTACCTATATTGC

*      1720         *      1740         *
pAB123-PA : .................................................. : 1750
MDV-B-PA  : .................................................. : 1750
            CGAGTGAATGGTACAAATAAGATCCAAATGAAATGGGGAATGGAAGCTAG

1760         *      1780         *      1800
pAB123-PA : .................................................. : 1800
MDV-B-PA  : .................................................. : 1800
            AAGATGTCTGCTTCAATCAATGCAACAAATGGAAGCAATTGTTGAACAAG

*      1820         *      1840         *
pAB123-PA : .................................................. : 1850
MDV-B-PA  : .................................................. : 1850
            AATCATCGATACAAGGATATGACATGACCAAAGCTTGTTTCAAGGGAGAC

1860         *      1880         *      1900
pAB123-PA : .................................................. : 1900
MDV-B-PA  : .................................................. : 1900
            AGAGTGAATAGTCCCAAAACTTTCAGTATTGGGACTCAAGAAGGAAAACT

*      1920         *      1940         *
pAB123-PA : .................................................. : 1950
MDV-B-PA  : .................................................. : 1950
            AGTAAAAGGATCCTTTGGGAAAGCACTAAGAGTAATATTCACCAAATGTT

1960         *      1980         *      2000
pAB123-PA : .................................................. : 2000
MDV-B-PA  : .................................................. : 2000
            TGATGCACTATGTATTTGGAAATGCCCAATTGGAGGGGTTTAGTGCCGAA

*      2020         *      2040         *
pAB123-PA : .................................................. : 2050
MDV-B-PA  : .................................................. : 2050
            TCTAGGAGACTTCTACTGTTAATTCAGGCATTAAAGGACAGAAAGGGCCC

2060         *      2080         *      2100
pAB123-PA : .................................................. : 2100
MDV-B-PA  : .................................................. : 2100
            TTGGGTATTCGACTTAGAGGGAATGTATTCTGGAATAGAAGAATGTATTA

*      2120         *      2140         *
pAB123-PA : .................................................. : 2150
MDV-B-PA  : .................................................. : 2150
            GTAACAACCCTTGGGTAATACAGAGTGCATACTGGTTTAATGAATGGTTG

2160         *      2180         *      2200
pAB123-PA : .................................................. : 2200
MDV-B-PA  : .................................................. : 2200
            GGCTTTGAAAAAGAGGGGAGTAAAGTATTAGAATCAATAGATGAAATAAT
```

Fig. 5N

```
              *         2220         *        2240         *
pAB123-PA : ................................................ : 2250
MDV-B-PA  : ................................................ : 2250
            GGATGAATGAAAGAAGGGCATAGCGCTCAATTTGGTACTATTTTGTTCAT

2260        *         2280         *        2300
pAB123-PA : ................................................ : 2300
MDV-B-PA  : ................................................ : 2300
            TATGTATCTAAACATCCAATAAAAAGAATTGAGAATTAAAAATGCACGTG pAB123-PA : ........ : 2308
MDV-B-PA  : ........ : 2308
            TTTCTACT
```

```
                         *        20         *        40         *
MDV-B-HA   : .................................................. :  50
pAB124-HA  : .................................................. :  50
             AGCAGAAGCAGAGCATTTTCTAATATCCACAAAATGAAGGCAATAATTGT

60         *        80         *       100
MDV-B-HA   : .................................................. : 100
pAB124-HA  : .................................................. : 100
             ACTACTCATGGTAGTAACATCCAATGCAGATCGAATCTGCACTGGGATAA

*       120         *       140         *
MDV-B-HA   : ................................................t : 150
pAB124-HA  : .................................................. : 150
             CATCGTCAAACTCACCCCATGTGGTCAAAACTGCTACTCAAGGGGAAGTC

160         *       180         *       200
MDV-B-HA   : ...t.............................................. : 200
pAB124-HA  : .................................................. : 200
             AACGTGACTGGTGTGATACCACTGACAACAACACCTACCAAATCTCATTT

*       220         *       240         *
MDV-B-HA   : .................................................. : 250
pAB124-HA  : .................................................. : 250
             TGCAAATCTCAAAGGAACACAGACCAGAGGGAAACTATGCCCAAACTGTC

260         *       280         *       300
MDV-B-HA   : .................................................. : 300
pAB124-HA  : .................................................. : 300
             TCAACTGCACAGATCTGGACGTGGCCTTGGGCAGACCAAAGTGTATGGGG

*       320         *       340         *
MDV-B-HA   : .................................................. : 350
pAB124-HA  : .................................................. : 350
             ACCATACCTTCGGCAAAAGCTTCAATACTCCACGAAGTCAAACCTGTTAC

360         *       380         *       400
MDV-B-HA   : .................................................. : 400
pAB124-HA  : .................................................. : 400
             ATCTGGGTGCTTTCCTATAATGCACGACAGAACAAAAATCAGACAGCTAC

*       420         *       440         *
MDV-B-HA   : .................................................. : 450
pAB124-HA  : .................................................. : 450
             CCAATCTTCTCAGAGGATATGAAAATATCAGGTTATCAGCCCGTAACGTT

460         *       480         *       500
MDV-B-HA   : .................................................. : 500
pAB124-HA  : .................................................. : 500
             ATCAACGCAGAAACGGCACCAGGAGGACCCTACATAGTTGGAACCTCAGG

*       520         *       540         *
MDV-B-HA   : .................................................. : 550
pAB124-HA  : .................................................. : 550
             ATCTTGCCCTAACGTTACCAATGGCAAAGGATTCTTCGCAACAATGGCTT

560         *       580         *       600
MDV-B-HA   : .................................................. : 600
```

Fig. 5P

```
pAB124-HA    : ............................................... :  600
               GGGCTGTCCCAAAAAACAACAAAACCAAAACAGCAACGAACCCATTAACA

*        620         *        640        *
MDV-B-HA     : ............................................... :  650
pAB124-HA    : ............................................... :  650
               GTAGAAGTACCATACATTTGTACAAAAGGAGAAGACCAAATTACTGTTTG

660         *        680         *        700
MDV-B-HA     : ............................................... :  700
pAB124-HA    : ............................................... :  700
               GGGGTTCCATTCTGATGACGAAACCCAAATGGTAACACTCTATGGAGACT

*        720         *        740        *
MDV-B-HA     : ............................................... :  750
pAB124-HA    : ............................................... :  750
               CGAAGCCTCAAAAGTTCACCTCATCTGCCAACGGAGTAACCACACATTAT

760         *        780         *        800
MDV-B-HA     : ............................................... :  800
pAB124-HA    : ............................................... :  800
               GTTTCTCAGATTGGTGGCTTCCCAAATCAAACAGAAGACGAAGGGCTACC

*        820         *        840        *
MDV-B-HA     : ............................................... :  850
pAB124-HA    : ............................................... :  850
               ACAAAGCGGCAGAATTGTTGTTGATTACATGGTGCAAAAACCTGGAAAAA

860         *        880         *        900
MDV-B-HA     : ............................................... :  900
pAB124-HA    : ............................................... :  900
               CAGGAACAATTGTCTATCAAAGAGGTGTTTTATTGCCTCAAAAAGTGTGG

*        920         *        940        *
MDV-B-HA     : ............................................... :  950
pAB124-HA    : ............................................... :  950
               TGCGCAAGTGGCAGGAGCAAGGTAATAAAAGGGGCCTTGCCTTTAATTGG

960         *        980         *       1000
MDV-B-HA     : ............................................... : 1000
pAB124-HA    : ............................................... : 1000
               TGAAGCAGATTGCCTCCACGAAAAATACGGTGGATTAAACAAAAGCAAGC

*       1020         *       1040        *
MDV-B-HA     : ............................................... : 1050
pAB124-HA    : ............................................... : 1050
               CTTACTACACAGGAGAACATGCAAAAGCCATAGGAAATTGCCCAATATGG

1060        *       1080         *       1100
MDV-B-HA     : ............................................... : 1100
pAB124-HA    : ............................................... : 1100
               GTGAAAACACCCTTGAAGCTGGCCAATGGAACCAAATATAGACCTCCTGC
```

Fig. 5Q

```
                  *         1120          *         1140          *
MDV-B-HA   : ..............................................: 1150
pAB124-HA  : ..............................................: 1150
             AAAACTATTAAAGGAAAGGGGTTTCTTCGGAGCTATTGCTGGTTTCTTGG

1160          *         1180          *         1200
MDV-B-HA   : ..............................................: 1200
pAB124-HA  : ..............................................: 1200
             AAGGAGGATGGGAAGGAATGATTGCAGGTTGGCACGGATACACATCTCAT

*         1220          *         1240          *
MDV-B-HA   : ..............................................: 1250
pAB124-HA  : ..............................................: 1250
             GGAGCACATGGAGTGGCAGTGGCAGCAGACCTTAAGAGTACGCAAGAAGC

1260          *         1280          *         1300
MDV-B-HA   : ..............................................: 1300
pAB124-HA  : ..............................................: 1300
             TATAAACAAGATAACAAAAAATCTCAATTCTTTAAGTGAGCTAGAAGTAA

*         1320          *         1340          *
MDV-B-HA   : ..............................................: 1350
pAB124-HA  : ..............................................: 1350
             AGAATCTTCAAAGACTAAGCGGTGCAATGGATGAACTCCACAACGAAATA

1360          *         1380          *         1400
MDV-B-HA   : ..............................................: 1400
pAB124-HA  : ..............................................: 1400
             CTCGAGCTGGATGAGAAAGTGGATGATCTCAGAGCTGATACAATAAGCTC

*         1420          *         1440          *
MDV-B-HA   : ..............................................: 1450
pAB124-HA  : ..............................................: 1450
             GCAAATAGAGCTTGCAGTCTTGCTTTCCAACGAAGGAATAATAAACAGTG

1460          *         1480          *         1500
MDV-B-HA   : ..............................................: 1500
pAB124-HA  : ..............................................: 1500
             AAGATGAGCATCTCTTGGCACTTGAAAGAAAACTGAAGAAAATGCTGGGC

*         1520          *         1540          *
MDV-B-HA   : ..............................................: 1550
pAB124-HA  : ..............................................: 1550
             CCCTCTGCTGTAGACATAGGGAATGGATGCTTCGAAACCAAACACAAATG

1560          *         1580          *         1600
MDV-B-HA   : ..............................................: 1600
pAB124-HA  : ..............................................: 1600
             CAACCAGACTTGCCTAGACAGGATAGCTGCTGGCACCTTTAATGCAGGAG

*         1620          *         1640          *
MDV-B-HA   : ..............................................: 1650
pAB124-HA  : ..............................................: 1650
             AATTTTCTCTTCCCACTTTTGATTCACTAAATATTACTGCTGCATCTTTA

```
MDV-B-HA    : ................................................ : 1700
pAB124-HA   : ................................................ : 1700
              AATGATGATGGATTGGATAATCATACTATACTGCTCTACTACTCAACTGC

*        1720         *        1740         *
MDV-B-HA    : ................................................ : 1750
pAB124-HA   : ................................................ : 1750
              TGCTTCTAGTTTGGCTGTAACATTGATGATAGCTATCTTTATTGTTTATA

1760         *        1780         *        1800
MDV-B-HA    : ................................................ : 1800
pAB124-HA   : ................................................ : 1800
              TGGTCTCCAGAGACAATGTTTCTTGCTCCATCTGTCTATAAGGAAAATTA

*        1820         *        1840         *
MDV-B-HA    : ................................................ : 1850
pAB124-HA   : ................................................ : 1850
              AGCCCTGTATTTTCCTTTATTGTAGTGCTTGTTTGCTTGTCACCATTACA

1860         *        1880
MDV-B-HA    : ..............................- : 1884
pAB124-HA   : ..............................- : 1884
              AAAAACGTTATTGAAAAATGCTCTTGTTACTACT
```

```
              10         20         30         40         50
pAB125-NP : .................................................. :  50
MDV-B-NP  : .................................................. :  50
            AGCAGAAGCACAGCATTTTCTTGTGAACTTCAAGTACCAACAAAAACTGA 60         70         80         90        100
pAB125-NP : .................................................. : 100
MDV-B-NP  : .................................................. : 100
            AAATCAAAATGTCCAACATGGATATTGACGGCATCAACACTGGAACAATT 110        120        130        140        150
pAB125-NP : .................................................. : 150
MDV-B-NP  : .................................................. : 150
            GACAAAACACCAGAAGAAATAACTTCCGGAACCAGTGGGGCAACCAGACC 160        170        180        190        200
pAB125-NP : .................................................. : 200
MDV-B-NP  : .................................................. : 200
            AATCATCAAACCAGCAACCCTTGCCCCACCAAGCAACAAACGAACCCGAA 210        220        230        240        250
pAB125-NP : .................................................. : 250
MDV-B-NP  : .................................................. : 250
            ACCCATCCCCGGAAAGGGCAGCCACAAGCAGTGAAGCTGATGTCGGAAGG 260        270        280        290        300
pAB125-NP : .................................................. : 300
MDV-B-NP  : .................................................. : 300
            AGAACCCAAAAGAAACAAACCCCGACAGAGATAAAGAAGAGCGTCTACAA 310        320        330        340        350
pAB125-NP : .................................................. : 350
MDV-B-NP  : .................................................. : 350
            TATGGTAGTGAAACTGGGTGAATTCTACAACCAGATGATGGTCAAAGCTG 360        370        380        390        400
pAB125-NP : .................................................. : 400
MDV-B-NP  : .................................................. : 400
            GACTCAACGATGACATGGAGAGAAACCTAATCCAAAATGCACATGCTGCG 410        420        430        440        450
pAB125-NP : .................................................. : 450
MDV-B-NP  : .................................................. : 450
            GAAAGAATTCTATTGGCTGCTACTGATGACAAGAAAACTGAATTCCAAAA 460        470        480        490        500
pAB125-NP : .................................................. : 500
MDV-B-NP  : .................................................. : 500
            GAAAAAGAATGCCAGAGATGTCAAAGAAGGGAAAGAAGAAATAGACCACA 510        520        530        540        550
pAB125-NP : .................................................. : 550
MDV-B-NP  : .................................................. : 550
            ACAAAACAGGAGGCACCTTTTACAAGATGGTAAGAGATGATAAAACCATC 560        570        580        590        600
pAB125-NP : .................................................. : 600
```

Fig. 5T

```
MDV-B-NP  : .................................................. :  600
            TACTTCAGCCCTATAAGAATTACCTTTTTAAAAGAAGAGGTGAAAACAAT 610       620       630       640       650
pAB125-NP : .................................................. :  650
MDV-B-NP  : .................................................. :  650
            GTACAAAACCACCATGGGGAGTGATGGTTTCAGTGGACTAAATCACATCA 660       670       680       690       700
pAB125-NP : .................................................. :  700
MDV-B-NP  : .................................................. :  700
            TGATTGGGCATTCACAGATGAACGATGTCTGTTTCCAAAGATCAAAGGCA 710       720       730       740       750
pAB125-NP : .................................................. :  750
MDV-B-NP  : .................................................. :  750
            CTAAAAAGAGTTGGACTTGACCCTTCATTAATCAGTACTTTTGCAGGAAG 760       770       780       790       800
pAB125-NP : .................................................. :  800
MDV-B-NP  : .................................................. :  800
            CACACTCCCCAGAAGATCAGGTGCAACTGGTGTTGCGATCAAAGGAGGTG 810       820       830       840       850
pAB125-NP : .................................................. :  850
MDV-B-NP  : .................................................. :  850
            GAACTTTAGTGGCAGAAGCCATTCGATTTATAGGAAGAGCAATGGCAGAC 860       870       880       890       900
pAB125-NP : .................................................. :  900
MDV-B-NP  : .................................................. :  900
            AGAGGGCTATTGAGAGACATCAGAGCCAAGACGGCCTATGAAAAGATTCT 910       920       930       940       950
pAB125-NP : .................................................. :  950
MDV-B-NP  : .................................................. :  950
            TCTGAATCTGAAAAACAAGTGCTCTGCGCCCCAACAAAAGGCTCTAGTTG 960       970       980       990      1000
pAB125-NP : .................................................. : 1000
MDV-B-NP  : .................................................. : 1000
            ATCAAGTGATCGGAAGTAGAAATCCAGGGATTGCAGACATAGAAGACCTA 1010      1020      1030      1040      1050
pAB125-NP : .................................................. : 1050
MDV-B-NP  : .................................................. : 1050
            ACCCTGCTTGCCCGAAGCATGGTCGTTGTCAGGCCCTCTGTAGCGAGCAA 1060      1070      1080      1090      1100
pAB125-NP : .................................................. : 1100
MDV-B-NP  : .................................................. : 1100
            AGTGGTGCTTCCCATAAGCATTTATGCCAAAATACCTCAACTAGGGTTCA
```

Fig 5U

```
                 1110      1120      1130      1140      1150
pAB125-NP : .................................................. : 1150
MDV-B-NP  : .................................................. : 1150
            ATGTTGAAGAATACTCTATGGTTGGGTATGAAGCCATGGCTCTTTATAAT 1160      1170      1180      1190      1200
pAB125-NP : .................................................. : 1200
MDV-B-NP  : .................................................. : 1200
            ATGGCAACACCTGTTTCCATATTAAGAATGGGAGACGATGCAAAAGATAA 1210      1220      1230      1240      1250
pAB125-NP : .................................................. : 1250
MDV-B-NP  : .................................................. : 1250
            ATCACAATTATTCTTCATGTCTTGCTTCGGAGCTGCCTATGAAGACCTAA 1260      1270      1280      1290      1300
pAB125-NP : .................................................. : 1300
MDV-B-NP  : .................................................. : 1300
            GAGTTTTGTCTGCACTAACAGGCACAGAATTCAAGCATAGGTCAGCATTA 1310      1320      1330      1340      1350
pAB125-NP : .................................................. : 1350
MDV-B-NP  : .................................................. : 1350
            AAGTGCAAGGGTTTCCACGTTCCAGCAAAGGAGCAAGTGGAAGGAATGGG 1360      1370      1380      1390      1400
pAB125-NP : .................................................. : 1400
MDV-B-NP  : .................................................. : 1400
            GGCAGCTCTGATGTCCATCAAGCTCCAGTTTTGGGCTCCAATGACCAGAT 1410      1420      1430      1440      1450
pAB125-NP : .................................................. : 1450
MDV-B-NP  : .................................................. : 1450
            CTGGGGGGAATGAAGTAGGTGGAGACGGAGGGTCTGGTCAAATAAGTTGC 1460      1470      1480      1490      1500
pAB125-NP : .................................................. : 1500
MDV-B-NP  : .................................................. : 1500
            AGCCCCGTGTTTGCAGTAGAAAGACCTATTGCTCTAAGCAAGCAAGCTGT 1510      1520      1530      1540      1550
pAB125-NP : .................................................. : 1550
MDV-B-NP  : .................................................. : 1550
            AAGAAGAATGCTGTCAATGAATATTGAGGGACGTGATGCAGATGTCAAAG 1560      1570      1580      1590      1600
pAB125-NP : .................................................. : 1600
MDV-B-NP  : .................................................. : 1600
            GAAATCTACTCAAGATGATGAATGATTCAATGACTAAGAAAACCAATGGA 1610      1620      1630      1640      1650
pAB125-NP : .................................................. : 1650
MDV-B-NP  : .................................................. : 1650
            AATGCTTTCATTGGGAAGAAAATGTTTCAAATATCAGACAAAAACAAAAC 1660      1670      1680      1690      1700
pAB125-NP : .................................................. : 1700
```

Fig 5V

```
MDV-B-NP   : .................................................. : 1700
             CAATCCCATTGAGATTCCAATTAAGCAGACCATCCCCAATTTCTTCTTTG 1710       1720       1730       1740       1750
pAB125-NP  : .................................................. : 1750
MDV-B-NP   : .................................................. : 1750
             GGAGGGACACAGCAGAGGATTATGATGACCTCGATTATTAAAGCAACAAA 1760       1770       1780       1790       1800
pAB125-NP  : .................................................. : 1800
MDV-B-NP   : .................................................. : 1800
             ATAGACACTATGGCTGTGACTGTTTCAGTACGTTTGGAATGTGGGTGTTT 1810       1820       1830       1840       1850
pAB125-NP  : ..........................................-------- : 1842
MDV-B-NP   : ..........................................-------- : 1842
             ACTTTTATTGAAATAAATGTAAAAAATGCTGTTGTTTCTACT pAB125-NP  : -------- :   -
MDV-B-NP   : -------- :   -
```

```
              *        20         *        40         *
pAB126-NA : ..................................................  :  50
MDV-B-NA  : ..................................................  :  50
            AGCAGAAGCAGAGCATCTTCTCAAAACTGAAGCAAATAGCCCAAAAATGA

60        *        80         *       100
pAB126-NA : ..................................................  : 100
MDV-B-NA  : ..................................................  : 100
            ACAATGCTACCTTCAACTATACAAACGTTAACCCTATTTCTCACATCAGG

*       120         *       140         *
pAB126-NA : ..................................................  : 150
MDV-B-NA  : ..................................................  : 150
            GGGAGTGTTATTATCACTATATGTGTCAGCTTCACTGTCATACTTATTGT

160        *       180         *       200
pAB126-NA : ..................................................  : 200
MDV-B-NA  : ..................................................  : 200
            ATTCGGATATATTGCTAAAATTTTCACCAACAAAAATAACTGCACCAACA

*       220         *       240         *
pAB126-NA : ..................................................  : 250
MDV-B-NA  : ..................................................  : 250
            ATGTCATTGGATTGCGCGAACGTATCAAATGTTCAGGCTGTGAACCGTTC

260        *       280         *       300
pAB126-NA : ..................................................  : 300
MDV-B-NA  : ..................................................  : 300
            TGCAACAAAAGAGATGACATTTCTTCTCCCAGAGCCGGAGTGGACATACC

*       320         *       340         *
pAB126-NA : ..................................................  : 350
MDV-B-NA  : ..................................................  : 350
            CTCGTTTATCTTGCCAGGGCTCAACCTTTCAGAAAGCACTCCTAATTAGC

360        *       380         *       400
pAB126-NA : ..................................................  : 400
MDV-B-NA  : ..................................................  : 400
            CCTCATAGGTTCGGAGAAACCAGAGGAAACTCAGCTCCCTTGATAATAAG

*       420         *       440         *
pAB126-NA : ..................................................  : 450
MDV-B-NA  : ..................................................  : 450
            GGAACCCTTTGTTGCTTGTGGACCAAAGGAATGCAGACACTTTGCTCTAA

460        *       480         *       500
pAB126-NA : ..................................................  : 500
MDV-B-NA  : ..................................................  : 500
            CCCATTATGCAGCTCAACCAGGGGGATACTACAATGGAACAAGAAAGGAC

*       520         *       540         *
pAB126-NA : ..................................................  : 550
MDV-B-NA  : ..................................................  : 550
            AGAAACAAGCTGAGGCATCTGATTTCAGTCAAATTAGGCAAAATCCCAAC

```
pAB126-NA : .................................................. :  600
MDV-B-NA  : .................................................. :  600
            TGTAGAAAACTCCATTTTCCACATGGCAGCTTGGAGTGGTCCGCATGCC

*       620         *       640         *
pAB126-NA : .................................................. :  650
MDV-B-NA  : .................................................. :  650
            ATGATGGTAGAGAATGGACATATATCGGAGTTGATGGCCCTGACAGTAAT

660          *       680         *       700
pAB126-NA : .................................................. :  700
MDV-B-NA  : .................................................. :  700
            GCACTGATCAAAATAAAATATGGAGAAGCATATACTGACACATACCATTC

*       720         *       740         *
pAB126-NA : .................................................. :  750
MDV-B-NA  : .................................................. :  750
            CTATGCAAACAACATCCTAAGAACACAAGAAAGTGCCTGCAATTGCATCG

760          *       780         *       800
pAB126-NA : .................................................. :  800
MDV-B-NA  : .................................................. :  800
            GGGGAGATTGTTATCTTATGATAACTGATGGCTCAGCTTCAGGAATTAGT

*       820         *       840         *
pAB126-NA : .................................................. :  850
MDV-B-NA  : .................................................. :  850
            AAATGCAGATTTCTTAAAATTCGAGAGGGTCGAATAATAAAAGAAATATT

860          *       880         *       900
pAB126-NA : .................................................. :  900
MDV-B-NA  : .................................................. :  900
            TCCAACAGGAAGAGTAGAGCATACTGAAGAATGCACATGCGGGTTCGCCA

*       920         *       940         *
pAB126-NA : .................................................. :  950
MDV-B-NA  : .................................................. :  950
            GCAATAAAACCATAGAATGTGCCTGTAGAGATAACAGTTACACAGCAAAA

960          *       980         *      1000
pAB126-NA : .................................................. : 1000
MDV-B-NA  : .................................................. : 1000
            AGACCCTTTGTCAAATTAAATGTGGAGACTGATACAGCTGAAATAAGATT

*      1020         *      1040         *
pAB126-NA : .................................................. : 1050
MDV-B-NA  : .................................................. : 1050
            GATGTGCACAGAGACTTATTTGGACACCCCCAGACCAGATGATGGAAGCA

1060          *      1080         *      1100
pAB126-NA : .................................................. : 1100
MDV-B-NA  : .................................................. : 1100
            TAACAGGGCCTTGCGAATCTAATGGGGACAAAGGGCTTGGAGGCATCAAA
```

Fig. 5Y

```
                    *         1120         *         1140         *
pAB126-NA  : ........................................................ : 1150
MDV-B-NA   : ........................................................ : 1150
             GGAGGATTTGTCCATCAAAGAATGGCATCTAAGATTGGAAGATGGTACTC

1160         *         1180         *         1200
pAB126-NA  : ........................................................ : 1200
MDV-B-NA   : ........................................................ : 1200
             CCGAACGATGTCTAAAACTGAAAGAATGGGGATGGAACTGTATGTCAAGT

*         1220         *         1240         *
pAB126-NA  : ........................................................ : 1250
MDV-B-NA   : ........................................................ : 1250
             ATGATGGAGACCCATGGACTGACAGTGACGCCCTTGCTCCTAGTGGAGTA

1260         *         1280         *         1300
pAB126-NA  : ........................................................ : 1300
MDV-B-NA   : ........................................................ : 1300
             ATGGTTTCAATGAAAGAACCTGGTTGGTATTCTTTTGGCTTCGAAATAAA

*         1320         *         1340         *
pAB126-NA  : ........................................................ : 1350
MDV-B-NA   : ........................................................ : 1350
             AGATAAGAAATGTGATGTCCCCTGTATTGGGATAGAGATGGTACACGATG

1360         *         1380         *         1400
pAB126-NA  : ........................................................ : 1400
MDV-B-NA   : ........................................................ : 1400
             GTGGAAAAGAGACTTGGCACTCAGCAGCAACAGCCATTTACTGTTTGATG

*         1420         *         1440         *
pAB126-NA  : ........................................................ : 1450
MDV-B-NA   : ........................................................ : 1450
             GGCTCAGGACAATTGCTATGGGACACTGTCACAGGTGTTGATATGGCTCT

1460         *         1480         *         1500
pAB126-NA  : ........................................................ : 1500
MDV-B-NA   : ........................................................ : 1500
             GTAATGGAGGAATGGTTGAATCTGTTCTAAACCCTTTGTTCCTATTTTGT

*         1520         *         1540         *
pAB126-NA  : ........................................................ : 1550
MDV-B-NA   : ........................................................ : 1550
             TTGAACAATTGTCCTTACTGGACTTAATTGTTTCTGAAAAATGCTCTTGT pAB126-NA  : ........ : 1557
MDV-B-NA   : ........ : 1557
             TACTACT
```

```
                     *         20         *         40         *
pAB127-M : ..................................................  :  50
MDV-B-M  : ..................................................  :  50
           AGCAGAAGCACGCACTTTCTTAAAATGTCGCTGTTTGGAGACACAATTGC

60         *         80         *        100
pAB127-M : ..................................................  : 100
MDV-B-M  : ..................................................  : 100
           CTACCTGCTTTCACTAACAGAAGATGGAGAAGGCAAAGCAGAACTAGCAG

*        120         *        140         *
pAB127-M : ..................................................  : 150
MDV-B-M  : ..................................................  : 150
           AAAAATTACACTGTTGGTTCGGTGGGAAAGAATTTGACCTAGACTCTGCT

160         *        180         *        200
pAB127-M : ..................................................  : 200
MDV-B-M  : ..................................................  : 200
           TTGGAATGGATAAAAAACAAAAGATGCCTAACTGATATACAAAAAGCACT

*        220         *        240         *
pAB127-M : ..................................................  : 250
MDV-B-M  : ..................................................  : 250
           AATTGGTGCCTCTATCTGCTTTTTAAAACCCAAAGACCAAGAAAGAAAAA

260         *        280         *        300
pAB127-M : ..................................................  : 300
MDV-B-M  : ..................................................  : 300
           GAAGATTCATCACAGAGCCCCTGTCAGGAATGGGAACAACAGCAACAAAA

*        320         *        340         *
pAB127-M : ..................................................  : 350
MDV-B-M  : ..................................................  : 350
           AAGAAAGGCCTGATTCTAGCTGAGAGAAAAATGAGAAGATGTGTGAGTTT

360         *        380         *        400
pAB127-M : ..................................................  : 400
MDV-B-M  : ..................................................  : 400
           TCATGAAGCATTTGAAATAGCAGAAGGCCATGAAAGCTCAGCACTACTAT

*        420         *        440         *
pAB127-M : ..................................................  : 450
MDV-B-M  : ..................................................  : 450
           ATTGTCTCATGGTCATGTACCTGAACCCTGGAAATTATTCAATGCAAGTA

460         *        480         *        500
pAB127-M : ..................................................  : 500
MDV-B-M  : ..................................................  : 500
           AAACTAGGAACGCTCTGTGCTTTATGCGAGAAACAAGCATCACATTCACA

*        520         *        540         *
pAB127-M : ..................................................  : 550
MDV-B-M  : ..................................................  : 550
           AAGAGCTCATAGCAGAGCAGCAAGATCTTCAGTGCCTGGAGTGAGGCGAG

560         *        580         *        600
pAB127-M : ..................................................  : 600
```

Fig. 5AA

```
MDV-B-M    : .................................................. :  600
             AAATGCAGATGGTTTCAGCTGTAACACAGCAAAAACAATGAATGGAATG

*       520         *       640         *
pAB127-M   : .................................................. :  650
MDV-B-M    : .................................................. :  650
             GGGAAGGGAGAAGACGTCCAAAAACTGGCAGAAGAGCTGCAAAGCAACAT

660         *       680         *       700
pAB127-M   : .................................................. :  700
MDV-B-M    : .................................................. :  700
             TGGAGTATTGAGATCTCTGGGGGCAAGTCAAAAGAATGGAGAAGGAATTG

*       720         *       740         *
pAB127-M   : .................................................. :  750
MDV-B-M    : .................................................. :  750
             CAAAGGATGTAATGGAAGTGCTAAAGCAGAGCTCTATGGGAAATTCAGCT

760         *       780         *       800
pAB127-M   : .................................................. :  800
MDV-B-M    : .................................................. :  800
             CTTGTGAAGAAATACCTATAATGCTCGAACCATTTCAGATTCTTTCAATT

*       820         *       840         *
pAB127-M   : .................................................. :  850
MDV-B-M    : .................................................. :  850
             TGTTCTTTCATTTTATCAGCTCTCCATTTCATGGCTTGGACAATAGGGCA

860         *       880         *       900
pAB127-M   : .................................................. :  900
MDV-B-M    : .................................................. :  900
             TTTGAATCAAATAAAAGAGGAGTAAACCTGAAAATACGAATAAGAAATC

*       920         *       940         *
pAB127-M   : .................................................. :  950
MDV-B-M    : .................................................. :  950
             CAAATAAAGAGACAATAAACAGAGAGGTATCAATTTTGAGACACAGTTAC

960         *       980         *      1000
pAB127-M   : .................................................. : 1000
MDV-B-M    : .................................................. : 1000
             CAAAAGAAATCCAAGCCAAAGAAACAATGAAGGAAGTACTCTGACAA

*      1020         *      1040         *
pAB127-M   : .................................................. : 1050
MDV-B-M    : .................................................. : 1050
             CATGGAGATATTGAGTGACCACATAGTAATTGAGGGGCTTTCTGCTGAAG

1060         *      1080         *      1100
pAB127-M   : .................................................. : 1100
MDV-B-M    : .................................................. : 1100
             AGATAATAAAAATGGGTGAAACAGTTTTGGAGGTAGAAGAATTGCAGTAA
```

Fig. 5AB

```
            *         1120         *         1140         *
pAB127-M : ............................................. : 1150
MDV-B-M  : ............................................. : 1150
           ACCCAATTTTCACCGTATTTCTTGCTATGCATTTAAGCAAATTGTAATCA

1160         *         1180         *
pAB127-M : ............................................. : 1190
MDV-B-M  : ............................................. : 1190
           ATGTCAGCAAATAAACTGGAAAAAGTGCGTTGTTTCTACT
```

```
                10        20        30        40        50
pAB128-NS  : .................................................. :  50
MDV-B-NS   : .................................................. :  50
             AGCAGAAGCAGAGGATTTGTTTAGTCACTGGCAAACGGAAAAAAATGGCG 60        70        80        90       100
pAB128-NS  : .................................................. : 100
MDV-B-NS   : .................................................. : 100
             GACAACATGACCACAACACAAATTGAGGTAGGTCCGGGAGCAACCAATGC 110       120       130       140       150
pAB128-NS  : .................................................. : 150
MDV-B-NS   : .................................................. : 150
             CACCATAAACTTTGAAGCAGGAATTCTGGAGTGCTATGAAAGGCTTTCAT 160       170       180       190       200
pAB128-NS  : .................................................. : 200
MDV-B-NS   : .................................................. : 200
             GGCAAAGAGCCCTTGACTACCCTGGTCAAGACCGCCTAAACAGACTAAAG 210       220       230       240       250
pAB128-NS  : .................................................. : 250
MDV-B-NS   : .................................................. : 250
             AGAAAATTAGAATCAAGAATAAAGACTCACAACAAAAGTGAGCCTGAAAG 260       270       280       290       300
pAB128-NS  : .................................................. : 300
MDV-B-NS   : .................................................. : 300
             TAAAAGGATGTCTCTTGAAGAGAGAAAAGCAATTGGGGTAAAAATGATGA 310       320       330       340       350
pAB128-NS  : .................................................. : 350
MDV-B-NS   : .................................................. : 350
             AAGTGCTCCTATTTATGAATCCATCTGCTGGAATTGAAGGGTTTGAGCCA 360       370       380       390       400
pAB128-NS  : .................................................. : 400
MDV-B-NS   : .................................................. : 400
             TACTGTATGAAAAATTCCTCAAATAGCAACTGTCCAAACTGCAATTGGAC 410       420       430       440       450
pAB128-NS  : ...........G...................................... : 450
MDV-B-NS   : .................................................. : 450
             CGATTACCCTCCAACACCAGGAAAGTGCCTTGATGACATAGAAGAAGAAC 460       470       480       490       500
pAB128-NS  : .................................................. : 500
MDV-B-NS   : .................................................. : 500
             CGGAGAATGTTGATGACCCAACTGAAATAGTATTGAGGGACATGAACAAC 510       520       530       540       550
pAB128-NS  : .................................................. : 550
MDV-B-NS   : .................................................. : 550
             AAAGATGCAAGGCAAAAGATAAAGGAGGAAGTAAACACTCAGAAAGAAGG 560       570       580       590       600
pAB128-NS  : .................................................. : 600
```

Fig. 5AD

```
MDV-B-NS    : ............................................................ :  600
              GAAGTTCCGTTTGACAATAAAAAGGGATATACGTAATGTGTTGTCCTTGA 610       620       630       640       650
pAB128-NS   : ..................................................           :  650
MDV-B-NS    : ..................................................           :  650
              GAGTGTTGGTAAACGGAACATTCCTCAAGCACCCTAATGGATACAAGTCC 660       670       680       690       700
pAB128-NS   : ..................................................           :  700
MDV-B-NS    : ..................................................           :  700
              TTATCAACTCTGCATAGATTGAATGCATATGACCAGAGTGGGAGGCTTGT 710       720       730       740       750
pAB128-NS   : ..................................................           :  750
MDV-B-NS    : ..................................................           :  750
              TGCTAAACTTGTTGCTACTGATGATCTTACAGTGGAGGATGAAGAAGATG 760       770       780       790       800
pAB128-NS   : ..................................................           :  800
MDV-B-NS    : ..................................................           :  800
              GCCATCGGATCCTCAACTCACTCTTCGAGCGTTTTAATGAAGGACATTCA 810       820       830       840       850
pAB128-NS   : ..................................................           :  850
MDV-B-NS    : ..................................................           :  850
              AAGCCAATTCGAGCAGCTGAAACTGCGGTGGGAGTCTTATCCCAATTTGG 860       870       880       890       900
pAB128-NS   : ..................................................           :  900
MDV-B-NS    : ..................................................           :  900
              TCAAGAGCACCGATTATCACCAGAGGAGGGAGACAATTAGACTGGTTACG 910       920       930       940       950
pAB128-NS   : ..................................................           :  950
MDV-B-NS    : ..................................................           :  950
              GAAGAACTTTATCTTTTAAGTAAAAGAATTGATGATAACATATTGTTCCA 960       970       980       990      1000
pAB128-NS   : ..................................................           : 1000
MDV-B-NS    : ..................................................           : 1000
              CAAAACAGTAATAGCTAACAGCTCCATAATAGCTGACATGATTGTATCAT 1010      1020      1030      1040      1050
pAB128-NS   : ..................................................           : 1050
MDV-B-NS    : ..................................................           : 1050
              TATCATTATTGGAAACATTGTATGAAATGAAGGATGTGGTTGAAGTGTAC 1060      1070      1080      1090
pAB128-NS   : ...............................................              : 1098
MDV-B-NS    : ...............................................              : 1098
              AGCAGGCAGTGCTTGTGAATTTAAAATAAAAATCCTCTTGTTACTACT
```

Fig. 5AE

| PA 431 497 | NP 55 114 410 509 | M1 159 183 | ts | MDCK log pfu/ml 33°C | MDCK 37°C | MDCK Δlog | PCK log TCID$_{50}$/ml 33°C | PCK 37°C | PCK Δlog |
|---|---|---|---|---|---|---|---|---|---|
| M H | A A H T | Q V | ts | 6.6 | <2 | >3 | 5.6 | 3.0 | 2.6 |
| V Y | T V P A | H M | non-ts | 7.6 | 6.6 | 1.0 | 8.1 | 7.4 | 0.7 |
| V Y | A V P A | H M | non-ts | 7.6 | 7.1 | 0.5 | 7.4 | 6.5 | 0.95 |
| V Y | A V P A | H M | non-ts | 8.1 | 7.1 | 1.0 | 7.7 | 6.5 | 1.20 |
| M H | A A H T | Q V | ts | 7.1 | 3.1 | 4.0 | 7.1 | 3.5 | 3.6 |
| V Y | T V P A | H M | non-ts | 8.1 | 7.1 | 1.0 | 8.7 | 7.8 | 0.9 |
| V Y | A V P A | H M | non-ts | 8.1 | 7.2 | 0.9 | 8.5 | 7.8 | 0.7 |

Fig. 8

| PA 431 | PA 497 | NP 55 | NP 114 | NP 410 | NP 509 | M1 159 | M1 183 | phenotype | MDCK log pfu/ml 33°C | MDCK 37°C | MDCK Δlog | PCK log TCID50/ml 33°C | PCK 37°C | PCK Δlog |
|---|---|---|---|---|---|---|---|---|---|---|---|---|---|---|
| M | H | A | A | H | T | H | M | ts | 7.1 | 3.2 | 3.9 | 6.2 | 3.3 | 2.9 |
| M | H | A | V | P | A | Q | V | ts | n.d. | 3.2 | 3.0 | 5.8 | 2.9 | 2.9 |
| V | Y | A | A | H | T | Q | V | ts | 6.2 | 3.2 | 3.0 | 6.1 | 2.7 | 3.4 |
| V | Y | A | A | H | T | H | M | ts | 7.4 | 4.4 | 3.0 | 7.5 | 3.4 | 4.1 |
| V | Y | A | A | H | T | H | M | ts | 7.6 | 4.2 | 3.4 | 8.3 | 4.3 | 4.0 |
| M | H | A | V | P | A | H | M | ts | 7.4 | 4.4 | 3.0 | 8.1 | 4.3 | 3.8 |
| M | H | T | V | P | A | H | M | ts | 8.0 | 6.0 | 2.0 | 8.4 | 4.3 | 4.1 |
| V | Y | T | V | P | A | Q | V | non-ts | 5.6 | 6.0 | -0.4 | 6.4 | 4.5 | 1.9 |
| V | Y | T | V | P | A | Q | V | non-ts | 6.6 | 5.8 | 0.8 | 6.8 | 4.8 | 2.0 |

Fig. 9

| PA | | NP | | | M1 | | MDCK log pfu/ml | | | PCK log TCID$_{50}$/ml | | |
|---|---|---|---|---|---|---|---|---|---|---|---|---|
| 431 | 497 | 55 | 114 | 410 509 | 159 | 183 | | 33°C | 37°C | Δlog | 33°C | 37°C | Δlog |
| V | Y | A | V | P T | Q | V | non-ts | 6.2 | 5.2 | 1.0 | 6.8 | 5.5 | 1.4 |
| V | Y | A | A | P T | Q | V | non-ts | 6.8 | 6.4 | 0.4 | 7.2 | 6.1 | 1.1 |
| V | Y | A | A | P T | Q | V | non-ts | 6.4 | 6.2 | 0

| | 140 | | | 150 | | 160 | |
|---|---|---|---|---|---|---|---|
| Victoria lineage | | | | | | | |
| | 170 | 180 | | 190 | | | 200 |
| B/Victoria/2/87 | SGSCPNVTNGNGFFATMAWAVPKNDNNKTATNPLTVEVPYICTEGEDQITVWGFHSDSETQMVKLYGDSKP | | | | | | |
| B/Hong_Kong/330/01 | | | E | S | I | | SET A |
| B/Brisbane/32/02 | | | | S | I | | NEA A |
| B/Malaysia/2506/04 | | | | S | I | | NEX A |
| B/Hawaii/13/04 | | | | S | I | | NEX A |
| B/Ohio/1/05 | | | | S | I | I | SET A |
| Yamagata lineage | | | | | | | |
| B/Yamagata/16/88 | SGSCPNVTSRNGFFATMAWAVPRDN..KTATNPLTVEVPYICTKGEDQITVWGFHSDDKTQMKKLYGDSNP | | | | | | |
| B/Yamanashi/166/98 | | A | S | K N. | | HI E | DKT N |
| B/Johannesburg/5/99 | | A | KS | N. | | HI E | DKT N |
| B/Victoria/504/00 | | A | KS | N. | | HI E | DKT N |
| B/Shanghai/361/02 | | A | KS | K N. | | E | DKT N |
| B/Jilin/20/03 | | A | KS | K N. | | V E | NKTP N |
| B/Jiangsu/10/03 | R | A | KS | K N. | | E | NKT N |
| B/Florida/7/04 | | A | KS | K N. | | V E | XKXX N |

Fig. 12

INFLUENZA B VIRUSES HAVING ALTERATIONS IN THE HEMAGGLUTININ POLYPEPTIDE

RELATED PATENT APPLICATIONS

This application is a continuation of U.S. patent application Ser. No. 12/599,761, filed Nov. 11, 2009, now U.S. Pat. No. 8,673,613, which was filed under 35 U.S.C. § 371 as the U.S. national phase of International Application PCT/US2008/067301, filed Jun. 18, 2008, entitled INFLUENZA B VIRUSES HAVING ALTERATIONS IN THE HEMAGGLUTININ POLYPEPTIDE, naming as inventors Hong Jin and Zhongying Chen, which designated the U.S. and claims priority to U.S. application Ser. No. 60/944,600, filed Jun. 18, 2007. Each of the foregoing patent applications is incorporated herein by reference in its entirety, including all text, tables and drawings.

SEQUENCE LISTING

The instant application contains a Sequence Listing which has been submitted in ASCII format via EFS-Web and is hereby incorporated by reference in its entirety. Said ASCII copy, created on Feb. 19, 2013, is named MDI-0150-US_S-L.txt and is 41,021 bytes in size.

BACKGROUND OF THE INVENTION

Influenza viruses are made up of an internal ribonucleoprotein core containing a segmented single-stranded RNA genome and an outer lipoprotein envelope lined by a matrix protein. Influenza A and B viruses each contain eight segments of single stranded RNA with negative polarity. The eight genome segments of influenza B encode 11 proteins. The three largest genes code for components of the RNA polymerase, PB 1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and BM2. The smallest segment encodes two products: NS1 is translated from the full length RNA, while NS2 is translated from a spliced mRNA variant.

Vaccines capable of producing a protective immune response specific for influenza viruses have been produced for over 50 years. Vaccines can be characterized as whole virus vaccines, split virus vaccines, surface antigen vaccines and live attenuated virus vaccines. While appropriate formulations of any of these vaccine types is able to produce a systemic immune response, live attenuated virus vaccines are also able to stimulate local mucosal immunity in the respiratory tract.

FluMist™ is a live, attenuated vaccine that protects children and adults from influenza illness (Belshe et al. (1998) *The efficacy of live attenuated, cold-adapted, trivalent, intranasal influenza virus vaccine in children N Engl J Med* 338: 1405-12; Nichol et al. (1999) *Effectiveness of live, attenuated intranasal influenza virus vaccine in healthy, working adults: a randomized controlled trial JAMA* 282:137-44). FluMist™ vaccine strains contain HA and NA gene segments derived from the currently circulating wild-type strains along with six internal gene segments from a common master donor virus (MDV).

To date, commercially available influenza vaccines in the United States are propagated in embryonated hen's eggs. Many strains of influenza B viruses do not grow well in eggs and must become "egg-adapted." Unfortunately, egg adaptation of influenza B viruses results in loss of an N-linked glycosylation site at amino acid residue 196 or 197 of the HA polypeptide. Loss of the N-linked glycosylation site affects virus antigenicity and corresponding vaccine efficacy. Stabilization of the N-linked glycosylation site in influenza B viruses grown in eggs could be of significance in, inter alia, influenza B vaccine manufacture.

SUMMARY OF THE INVENTION

One embodiment of the invention encompasses a method of preparing an influenza B virus. A mutation resulting in an amino acid substitution at HA position 141 to arginine is introduced into an influenza B virus genome. The mutated influenza B virus genome is replicated under conditions whereby influenza B virus is produced.

Another embodiment of the invention encompasses a method of preparing an influenza B virus. A plurality of vectors is introduced into a population of host cells. The vectors comprise nucleotide sequences corresponding to: (a) at least 6 internal genome segments of a first influenza B strain, and (b) one or more genome segments encoding HA and NA polypeptides of at least a second influenza B strain. The HA polypeptide comprises an arginine at amino acid residue 141. The population of host cells is cultured at a temperature that does not exceed 35 degrees. The influenza virus is recovered.

BRIEF DESCRIPTION OF THE DRAWINGS

FIG. 3A-D: FIG. 3A and FIG. 3B, Characterization of recombinant MDV-B virus by RT-PCR, PB1 (SEQ ID NO: 40), HA (SEQ ID NO: 41), NS (SEQ ID NO: 42); FIG. 3C and FIG. 3D; Characterization of recombinant B/Yamanashi/166/98 by RT-PCR, wt-B/Yamanashi/166/98 (SEQ ID NO: 43), rec-B/Yamanashi/166/98 (SEQ ID NO: 44).

FIGS. 4A and B: Sequence of pAD3000 in GeneBank format (SEQ ID NO:3).

FIG. 5A-5AE: Sequence alignment with MDV-B and eight plasmids, FIGS. 5A-E, PB1 segment, MDV-B-PB1 (SEQ ID NO:4) and pAB121-PB1 (SEQ ID NO: 45); FIGS. 5F-J, PB2 segment, MDV-B-PB2 and pAB122-PB2 (SEQ ID NO:5); FIGS. 5K-0,PA segment, MDV-B-PA and pAB123-PA (SEQ ID NO:6); FIGS. 5P-5S, HA segment, MDV-B-HA (SEQ ID NO: 46) and pAB124-HA (SEQ ID NO:7); FIGS. 5T-5W, NP segment, MDV-B-NP and pAB125-NP (SEQ ID NO:8); FIGS. 5X-5Z, NA segment, MDV-B-NA and pAB126-NA (SEQ ID NO:9); FIGS. 5AA-5AC, M segment, MDV-B-M and pAB127-M (SEQ ID NO:10); FIGS. 5AD-5AE, NS segment, MDV-B-NS (SEQ ID NO:11) and pAB128-NS (SEQ ID NO: 47).

FIG. 8: Schematic illustration of triple-gene recombinants with wild type residues in PA, NP, and M1 proteins.

FIG. 9: Tabulation of growth of single-gene and double-gene recombinant viruses.

FIG. 10: Tabulation of amino acid residue of the nucleoprotein corresponding to non-ts phenotype.

FIG. 12: Alignment of the HA sequences near the 196/197 glycosylation site of several egg amplified influenza B strains. The Victoria lineage viruses are aligned with reference strain B/Victoria/2/87 (SEQ ID NO:12). The Yamagata lineage viruses are aligned with B/Yamagata/16/88 (SEQ ID NO:13). Only the residues differing from the reference strain are shown in the alignment. The potential N-glycosylation site (N—X-T/S) at position of 196/197 is indicated as underlined and in arrow. "." indicates amino acid deletion in the B/Yamagata lineages. "x" indicates mixed amino acid.

DETAILED DESCRIPTION

Figure 1:
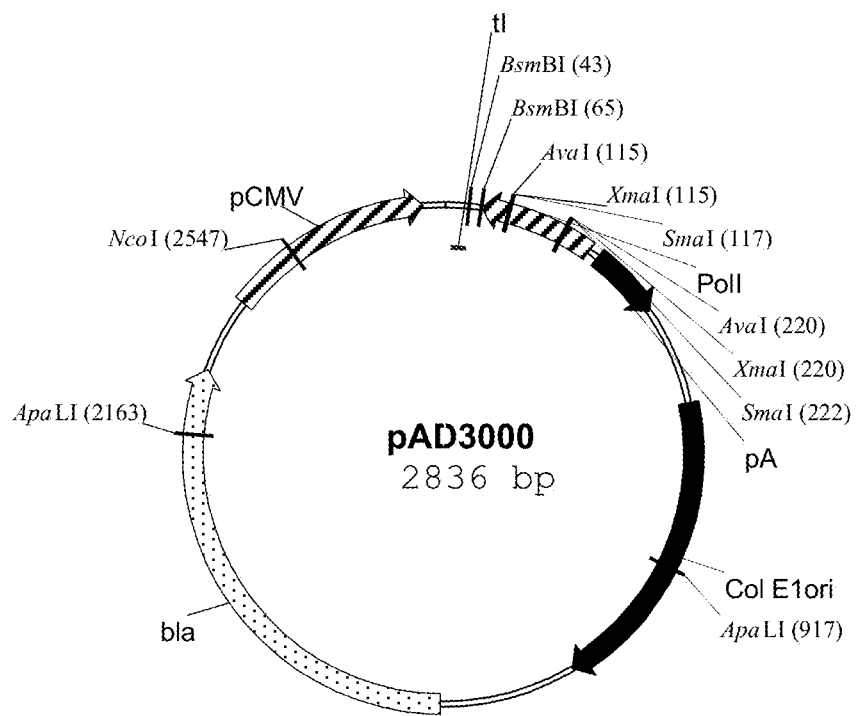
FIG. 1: Illustration of pAD3000 plasmid.

The present invention encompasses a system for producing influenza B viruses by introducing vectors into cultured cells. The influenza B viruses produced by the method may have amino acid residues at particular positions which influence the viruses ability to replicate in eggs, or may influence the characteristics of the viruses once replicated in eggs.

Unless defined otherwise, all scientific and technical terms are understood to have the same meaning as commonly used in the art to which they pertain. For the purpose of the present invention the following terms are defined below.

A "nucleic acid," "polynucleotide," "polynucleotide sequence" and "nucleic acid sequence" may be a single-stranded or double-stranded deoxyribonucleotide or ribonucleotide polymer, or a chimera or analogue thereof. These terms may also include polymers of analogs of naturally occurring nucleotides having the essential nature of natural nucleotides in that they hybridize to single-stranded nucleic acids in a manner similar to naturally occurring nucleotides (e.g., peptide nucleic acids).

A "gene" may refer to any nucleic acid associated with a biological function. Genes include coding sequences and/or the regulatory sequences required for their expression. A "gene" may refer to a specific genomic sequence, as well as to a cDNA or an mRNA encoded by that genomic sequence.

Genes may further include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one which regulates transcription in a specific tissue type or cell type, or types.

A "vector" may be a means by which a nucleic can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating.

An "expression vector" may be a vector, such as a plasmid, which is capable of promoting expression, as well as replication of a nucleic acid incorporated therein. A nucleic acid to be expressed may be "operably linked" to a promoter and/or enhancer, and subject to transcription regulatory control by the promoter and/or enhancer.

A "bi-directional expression vector" is typically characterized by two alternative promoters oriented in opposite directions relative to a nucleic acid situated between the two promoters, such that expression can be initiated in both orientations resulting in, e.g., transcription of both plus (+) or sense strand, and negative (−) or antisense strand RNAs. Alternatively, the bi-directional expression vector can be an ambisense vector, in which the viral mRNA and viral genomic RNA (as a cRNA) are expressed from the same strand.

"Isolated," when referring to a biological material, such as a nucleic acid or a protein, may be a biological material which is substantially free from components that normally accompany or interact with it in its naturally occurring environment. The isolated material may optionally comprise materials not found with the material in its natural environment, e.g., a cell.

"Recombinant" may indicate a material (e.g., a nucleic acid or protein) that has been artificially or synthetically (non-naturally) altered by human intervention. The alteration can be performed on the material within, or removed from, its natural environment or state.

Reassortant viruses include viruses that include genetic and/or polypeptide components derived from more than one parental viral strain or source. For example, a 7:1 reassortant includes 7 viral genomic segments (or gene segments) derived from a first parental virus, and 1 viral genomic segment, e.g., encoding hemagglutinin or neuraminidase, from a second parental virus. A 6:2 reassortant includes 6 genomic segments, most commonly the 6 internal genes from a first parental virus, and two genomic segments, e.g., hemagglutinin and neuraminidase, from a second parental virus. A 6:1:1 reassortant may include 6 genomic segments, most commonly the 6 internal genes from a first parental virus, 1 genomic segment from a second parental virus encoding hemagglutinin, and 1 genomic segment from a third parental virus encoding neuraminidase. The 6 internal genes may be those of more than one parental virus as well.

Introduction of vectors or nucleic acids may refer to the incorporation of the nucleic acids into a eukaryotic or prokaryotic cell. The vectors or nucleic acids may be incorporated into the cell by incorporation in its genome (e.g., chromosome, plasmid, plastid or mitochondrial DNA), may be converted into an autonomous replicon, or may be transiently expressed (e.g., transfected mRNA). Introduction includes such methods as "infection," "transfection," "transformation" and "transduction." Introduction may be performed by electroporation, calcium phosphate precipitation, or lipid mediated transfection (lipofection).

A host cell may be a cell which contains a heterologous nucleic acid, such as a vector, and which supports the replication and/or expression of the nucleic acid. Host cells can be prokaryotic cells such as *E. coli*, or eukaryotic cells such as yeast, insect, amphibian, avian or mammalian cells, including human cells. Host cells include Vero (African green monkey kidney) cells, Per.C6 cells (human embryonic retinal cells), BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COST cells). Host cell also encompasses combinations or mixtures of cells including, e.g., mixed cultures of different cell types or cell lines (e.g., Vero and CEK cells). Co-cultivation of electroporated Vero cells is described, for example, in PCT/US04/42669 filed Dec. 22, 2004, which is incorporated by reference in their entirety.

A temperature sensitive (ts) virus typically exhibits a 100-fold or greater reduction in titer at 37° C. relative to 33° C. for influenza B strains. A cold adapted (ca) virus typically exhibits growth at 25° C. within 100-fold of its growth at 33° C. An attenuated (att) virus typically replicates in the upper airways of ferrets but is not detectable in lung tissues, and does not cause influenza-like illness in the animals. Growth indicates viral quantity as indicated by titer, plaque size or morphology, particle density or other measures known to those of skill in the art.

An artificially engineered virus, viral nucleic acid, or virally encoded product, e.g., a polypeptide, a vaccine, is a virus, nucleic acid or product, which includes at least one mutation introduced by recombinant methods, e.g., site directed mutagenesis, PCR mutagenesis, etc. An artificially engineered virus (or viral component or product) comprising one or more nucleotide mutations and/or amino acid substitutions indicates that the viral genome or genome segment encoding the virus (or viral component or product) is not derived from naturally occurring sources, such as a naturally occurring or previously existing laboratory strain of virus produced by non-recombinant methods (such as progressive passage at 25° C.), e.g., a wild type or cold adapted A/Ann Arbor/6/60 or B/Ann Arbor/1/66 strain.

Vectors

In some methods encompassed by the invention, viral genomic segments corresponding to each of the eight segments of the influenza B virus may be inserted into a plurality of vectors for manipulation and production of influenza viruses. Eight vectors may be included in the plurality of vectors; eight vectors comprising nucleic acid sequences corresponding to the eight genomic segments of one or more influenza B viruses. The plurality of vectors may include more or fewer vectors. For instance, 11 vectors may be included in the plurality of vectors; 11 vectors comprising nucleic acid sequences corresponding to the coding sequences of the 11 influenza B virus proteins. Alternatively, one vector may be included in the plurality of vectors; one vector comprising each of the eight genomic segments of the one or more influenza B viruses. Two, three, four, five, six, seven, nine, or ten vectors may also be included in the plurality of vectors.

The vectors may be viral vectors, plasmids, cosmids, phage, or artificial chromosomes. If the vectors are plasmids, the plasmids may provide one or more origins of replication functional in bacterial and eukaryotic cells, and, optionally, a marker convenient for screening or selecting cells incorporating the plasmid sequence. An example vector, plasmid pAD3000 is illustrated in FIG. 1.

If the vectors are plasmids the plasmids may be bi-directional expression vectors capable of initiating transcription of the viral genomic segments in either direction, that is, giving rise to both (+) strand and (−) strand viral RNA molecules. To effect bi-directional transcription, each of the viral genomic segments is inserted into a vector having at least two independent promoters, such that copies of viral genomic RNA are transcribed by a first RNA polymerase promoter (e.g., Pol I), from one strand, and viral mRNAs are synthesized from a second RNA polymerase promoter (e.g., Pol II). Accordingly, the two promoters are arranged in opposite orientations flanking at least one cloning site (i.e., a restriction enzyme recognition sequence) preferably a unique cloning site, suitable for insertion of viral genomic RNA segments. Alternatively, an "ambisense" vector can be employed in which the (+) strand mRNA and the (−) strand viral RNA (as a cRNA) are transcribed from the same strand of the vector.

Expression Vectors

The influenza virus genome segment to be expressed is operably linked to an appropriate transcription control sequence (promoter) to direct mRNA synthesis. A variety of promoters are suitable for use in expression vectors for regulating transcription of influenza virus genome segments. In certain embodiments, e.g., wherein the vector is the plasmid pAD3000, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like. In addition, bacteriophage promoters can be employed in conjunction with the cognate RNA polymerase, e.g., the T7 promoter.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha.-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) *Heat stress promoters and transcription factors Results Probl Cell Differ* 20:125-62; Kriegler et al. (1990) *Assembly of enhancers, promoters, and splice signals to control expression of transferred genes Methods in Enzymol* 185: 512-27). Optionally, the amplicon can also contain a ribosome binding site or an internal ribosome entry site (IRES) for translation initiation.

The vectors of the invention may also include sequences necessary for the termination of transcription and for stabilizing the mRNA, such as a polyadenylation site or a terminator sequence. Such sequences are commonly available from the 5' and, occasionally 3', untranslated regions of eukaryotic or viral DNAs or cDNAs. In one embodiment, e.g., involving the plasmid pAD3000, the SV40 polyadenylation sequences provide a polyadenylation signal.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate DNA sequence as described above, as well as an appropriate promoter or control sequence, can be employed to transform a host cell permitting expression of the protein.

Additional Expression Elements

A genome segment encoding an influenza virus protein may include any additional sequences necessary for expression of the segment. For example, specific initiation signals which aid in the efficient translation of the heterologous coding sequence may be included. These signals can include, e.g., the ATG initiation codon and adjacent sequences. To insure translation of the entire protein encoded by the genome segment, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

Additional polynucleotide sequences such as signal sequences, secretion or localization sequences, and the like can be incorporated into the vector, usually, in-frame with the polynucleotide sequence of interest, e.g., to target polypeptide expression to a desired cellular compartment, membrane, or organelle, or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Internal Genome Segments

Internal genomic segments of an influenza B virus strain may be the internal genomic segments of one or more master influenza B virus. The one or more master influenza B virus may be selected on the basis of desirable properties relevant to vaccine administration. For example, a master donor influenza B virus strain may be selected for an attenuated phenotype, cold adaptation and/or temperature sensitivity. In this context, ca B/Ann Arbor/1/66, or an artificially engineered influenza B strain incorporating one or more of the amino acid substitutions specified in Table 17 may be the master donor influenza B strain. These amino acid substitutions may include substitutions at one or more of PB2$^{630}$; PA$^{431}$; PA$^{497}$; NP$^{55}$; NP$^{114}$; NP$^{410}$; NP509; M1$^{159}$ and M1$^{183}$. The amino acid substitutions may include one or more of the following: PB2$^{630}$ (S630R); PA$^{431}$ (V431M); PA$^{497}$ (Y497H); NP$^{55}$ (T55A); NP$^{114}$ (V114A); NP$^{410}$ (P410H); NP509 (A509T); M1$^{159}$ (H159Q) and M1$^{183}$ (M183V). The amino acid substitutions may include substitutions at all of PB2$^{630}$; PA$^{431}$; PA$^{497}$; NP$^{55}$; NP$^{114}$; NP$^{410}$; NP509; M1$^{159}$ and M1$^{183}$. The substitutions may be all of PB2$^{630}$ (S630R); PA$^{431}$ (V431M); PA$^{497}$ (Y497H); NP$^{55}$ (T55A); NP$^{114}$ (V114A); NP$^{410}$ (P410H); NP509 (A509T); M1$^{159}$ (H159Q) and M1$^{183}$ (M183V).

The six internal genomic segments of the one or more influenza master influenza B virus strain, (i.e., PB1, PB2, PA, NP, NB, M1, BM2, NS1 and NS2) may transfected into suitable host cells in combination with hemagglutinin and neuraminidase segments from an antigenically desirable strain, e.g., a strain predicted to cause significant local or global influenza infection. Following replication of the reassortant virus in cell culture at appropriate temperatures for efficient recovery, e.g., equal to or less than 35° C., such as between about 30° C. and 35° C., such as between about 32° C. and 35° C., such as between about 32° C. and 34° C., or at about 30° C., or at about 31° C., or at about 32° C., or at about 33° C., or at about 34° C. or at about 35° C., reassortant viruses is recovered. The recovered virus may be replicated in embryonated eggs. The recovered virus may be replicated in cultured cells. The recovered virus, which may have been replicated in embryonated eggs or cultured cells, may be inactivated using a denaturing agent such as formaldehyde or β-propiolactone.

Influenza B Viruses with Altered Attributes

The methods of the present invention also encompass introducing a mutation resulting in an amino acid substitution at HA position 141. The mutation may increase the ability of the influenza B viruses to replicate in embryonated chicken eggs when compared to HA unsubstituted influenza viruses. The substitution at HA position 141 may further allow the influenza virus to retain glycosylation at HA amino acid residue 196/197. The substitution at HA position 141 may further not significantly alter antigenicity of the HA. The substitution at HA position 141 may be for an arginine, a histine, or a cysteine.

The introduction of the amino acid substitution into HA may enhance the ability of the influenza B virus to replicate in eggs by at least 10%, or by at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% when compared to the unmodified influenza virus. The titer of the virus with the enhanced ability to replicate in eggs may be at least 5.0 log$_{10}$ PFU/ml, at least 6.0 log$_{10}$ PFU/ml, at least 6.5 log$_{10}$ PFU/ml, at least 7.0 log$_{10}$ PFU/ml, at least 7.25 log$_{10}$ PFU/ml, at least 7.5 log$_{10}$ PFU/ml, at least 7.75 log$_{10}$ PFU/ml, at least 8.0 log$_{10}$ PFU/ml, at least 8.25 log$_{10}$ PFU/ml, at least 8.5 log$_{10}$ PFU/ml, at least 8.75 log$_{10}$ PFU/ml, at least 9.0 log$_{10}$ PFU/ml, or at least 9.5 log$_{10}$ PFU/ml. The influenza B virus with the enhanced ability to replicate in eggs when compared to the unmodified influenza virus will also retain HA glycosylation at amino acid residue position 196/197.

The introduction of the amino acid substitution may further not significantly alter the antigenicity of the substituted influenza virus when compared to the unsubstituted virus. The antigenicity of the substituted influenza virus when compared to the unsubstituted virus differs by less then 5%, 10%, 20%, 25%, 30%, 40%, or 50%. Methods to determine viral antigenicity are well known in the art.

Introduction of a mutation which results in the amino acid substitution in the HA at residue position 141 may modulate receptor binding activity of the HA. Receptor binding activity of the HA includes but is not limited to the binding of HA to sialic acid residues (e.g., 2,6-linked sialyl-galactosyl moieties [Siaα(2,6)Gal] and 2,3-linked sialyl-galactosyl moieties [Siaα(2,3)Gal]) present on the cell surface glycoproteins or glycolipids. Methods to assay HA binding are well known in the art. Introduction of the mutation that results in an amino acid substitution at HA residue 141 may enhance the binding of HA to [Siaα(2,3)Gal] moieties. Enhanced binding to [Siaα(2,3)Gal] moieties may be by at least 10%, or by at least 20%, or by at least 30%, or by at least 40%, or by at least 50%, or by at least 60%, or by at least 70%, or by at least 80%, or by at least 90%, or by at least 100%, or by at least 200% in an, e.g., hemaagglutination, assay well known to those of skill in the art.

The influenza B variant virus may further have one or more attributes including attenuation, a cold adaptation, temperature sensitivity, or any combination thereof. The influenza B variant virus may have one or more of these attributes owing to incorporation of internal genome segments of a master influenza B donor virus, such as influenza B/Ann Arbor/1/66.

The influenza B variant virus may be any influenza B virus that comprises an HA polypeptide with a glycine residue at position 141. The influenza B virus HA polypeptide may be that of influenza strain B/Victoria/2/87, B/Hong Kong/330/01, B/Brisbane/32/02, B/Malaysia/2506/04, B/Hawaii/13/04, B/Ohio/1/05, B/Yamagata/16/88, B/Yamanashi/166/98, B/Johannesburg/5/99, B/Vicotria/504/00, B/Shanghai/361/02, B/Jilin/20/03, or B/Florida/7/04.

Cell Culture

In some methods encompassed by the invention, a plurality of vectors is introduced into host cells. These host cells include, e.g., Vero cells, Per.C6 cells, BHK cells, MDCK cells, 293 cells and COS cells, including 293T cells, COST cells. Alternatively, co-cultures including two of the above cell lines, e.g., MDCK cells and either 293T or COS cells may employed at a ratio, e.g., of 1:1. The cells may be maintained in suitable commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) *Culture of Animal Cells: Manual of Basic Technique*, Alan R. Liss, New York; Paul (1975) *Cell and Tissue Culture*, 5th ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation*. In Cohen and Shafferman (eds) *Novel Strategies in Design and Production of Vaccines*, which is incorporated herein in its entirety. Additionally, variations in such procedures adapted to the present invention are readily determined through routine experimentation.

Cells for production of influenza B virus may be cultured in serum-containing or serum free medium. In some case, e.g., for the preparation of purified viruses, it may be desirable to grow the host cells in serum free conditions.

Cells may be cultured on any scale. Cells may be cultured on small scale, e.g., less than 25 ml medium, in culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it may be desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, the cultures may be maintained at a temperature less than or equal to 35° C., less than or equal to 34° C., less than or equal to 33° C., less than or equal to 32° C., less than or equal to 31° C., or less than or equal to 30° C. The cells may be cultured at a temperature between about 30° C. and 35° C., between about 32° C. and 35° C., between about 32° C. and about 34° C., or between about 32° C. and 33° C.

Introduction of Vectors into Host Cells

Vectors comprising nucleotide sequences corresponding to influenza genome segments may be introduced (e.g., transfected) into host cells according to methods well known in the art including, e.g., calcium phosphate co-precipitation, electroporation, microinjection, lipofection, and transfection employing polyamine transfection reagents. By way of example, vectors, e.g., plasmids, can be transfected into host cells, such as COS cells, 293T cells or combinations of COS or 293T cells and MDCK cells, using the polyamine transfection reagent TransIT-LT1 (Minis) according to the manufacturer's instructions. Approximately 1 µg of each vector can be introduced into the population of host cells with approximately 2 µl of TransIT-LT1 diluted in 160 µl medium in a total volume of 200 µl. The DNA:transfection reagent mixtures are incubated at room temperature for 45 min followed by addition of 800 µl of medium. The transfection mixture is added to the host cells, and the cells are cultured as described above.

Alternatively, electroporation can be employed to introduce vectors comprising nucleotide sequences corresponding to influenza genome segments into host cells. By way of example, plasmid vectors comprising nucleotide sequences corresponding to influenza B genome segments may be introduced into Vero cells using electroporation according to the following procedure. $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 µl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS or OPTI-MEM without serum. The cuvette is washed to recover any remaining cells and the wash suspension is divided between the two wells. Final volume is approximately 3.5 mls. The cells are then incubated under conditions permissive for viral growth.

Recovery of Viruses

Viruses may be recovered from the culture medium of cells into which a plurality of vectors had been introduced. Crude medium may be obtained and clarified, and influenza viruses in the clarified medium may then be concentrated. Common methods of concentration include filtration, ultrafiltration, adsorption on barium sulfate and elution, and centrifugation. By way of example, crude medium from infected cultures may first be clarified by centrifugation at, e.g., 1000-2000×g for a time sufficient to remove cell debris and other large particulate matter, e.g., between 10 and 30 minutes. Alternatively, the medium may be filtered through a 0.8 μm cellulose acetate filter to remove intact cells and other large particulate matter. Optionally, the clarified medium supernatant may then be centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus may be concentrated by density gradient centrifugation on sucrose (60%-12%) or potassium tartrate (50%-10%). Either continuous or step gradients, e.g., a sucrose gradient between 12% and 60% in four 12% steps, are suitable. The gradients may be centrifuged at a speed, and for a time, sufficient for the viruses to concentrate into a visible band for recovery. Alternatively, and for large scale commercial applications, virus may be elutriated from density gradients using a zonal-centrifuge rotor operating in continuous mode. Additional details sufficient to guide one of skill through the preparation of influenza viruses from tissue culture are provided, e.g., in Furminger. *Vaccine Production*, in Nicholson et al. (eds) *Textbook of Influenza* pp. 324-332; Merten et al. (1996) *Production of influenza virus in cell cultures for vaccine preparation*, in Cohen & Shafferman (eds) *Novel Strategies in Design and Production of Vaccines* pp. 141-151, and U.S. Pat. No. 5,690,937. If desired, the recovered viruses can be stored at −80° C. in the presence of sucrose-phosphate-glutamate (SPG) as a stabilizer.

Methods and Compositions for Prophylactic Administration of Vaccines

Recombinant and reassortant viruses of the invention can be administered prophylactically in an appropriate carrier or excipient to stimulate an immune response specific for one or more strains of influenza virus. The carrier or excipient may be a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected Hens' eggs (i.e., normal allantoic fluid "NAF") or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

Generally, the influenza viruses of the invention are administered in a quantity sufficient to stimulate an immune response specific for one or more strains of influenza virus. Dosages and methods for eliciting a protective immune response against one or more influenza strains are known to those of skill in the art. By way of example, inactivated influenza viruses may be provided in the range of about 1-1000 $HID_{50}$ (human infectious dose), i.e., about $10^5$-$10^8$ pfu (plaque forming units) per dose administered. Alternatively, about 10-50 μg, e.g., about 15 μg HA is administered without an adjuvant, with smaller doses being administered with an adjuvant. Typically, the dose will be adjusted within this range based on, e.g., age, physical condition, body weight, sex, diet, time of administration, and other clinical factors. The prophylactic vaccine formulation may be systemically administered, e.g., by subcutaneous or intramuscular injection using a needle and syringe, or a needleless injection device. Alternatively, the vaccine formulation may be administered intranasally, either by drops, large particle aerosol (greater than about 10 microns), or spray into the upper respiratory tract. For intranasal administration, attenuated live virus vaccines may be used, e.g., an attenuated, cold adapted and/or temperature sensitive recombinant or reassortant influenza virus. While stimulation of a protective immune response with a single dose is preferred, additional dosages may be administered, by the same or different route, to achieve the desired prophylactic effect.

Alternatively, an immune response can be stimulated by ex vivo or in vivo targeting of dendritic cells with influenza viruses. For example, proliferating dendritic cells can be exposed to viruses in a sufficient amount and for a sufficient period of time to permit capture of the influenza antigens by the dendritic cells. The cells are then transferred into a subject to be vaccinated by standard intravenous transplantation methods.

One or more influenza B viruses may be present in a formulation for prophylactic or therapeutic treatment of influenza. A formulation may comprise one influenza B virus. A formulation may comprise one influenza B virus and one influenza A virus. A formulation may comprise one influenza B virus and two influenza A viruses. A formulation may comprise two influenza B viruses and two influenza A viruses. A formulation may comprise two influenza B viruses. At least one influenza B virus in the formulation may comprise an arginine at amino acid residue 141.

A formulation for prophylactic administration of the influenza viruses, or subunits thereof, may also contain one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

The formulation for prophylactic administration of influenza viruses may be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein or an expression vector encoding the protein can be administered to produce an immunostimulatory effect.

In another embodiment, the vectors of the invention comprising nucleotide sequences corresponding to influenza genome segments may be employed to introduce heterologous nucleic acids into a host organism or host cell, such as a mammalian cell, e.g., cells derived from a human subject, in combination with a suitable pharmaceutical carrier or excipient as described above. A heterologous nucleic acid may be inserted into a non-essential region of a gene or genome segment. The heterologous polynucleotide sequence can encode a polypeptide or peptide, or an RNA such as an antisense RNA or ribozyme. The heterologous nucleic acid is then introduced into a host or host cells by producing recombinant viruses incorporating the heterologous nucleic, and the viruses are administered as described above.

Alternatively, a vector of the invention including a heterologous nucleic acid can be introduced and expressed in a host cells by co-transfecting the vector into a cell infected with an influenza virus. Optionally, the cells are then returned or delivered to the subject, typically to the site from which they were obtained. In some applications, the cells are grafted onto a tissue, organ, or system site (as described above) of interest, using established cell transfer or grafting procedures. For example, stem cells of the hematopoietic lineage, such as bone marrow, cord blood, or peripheral blood derived hematopoietic stem cells can be delivered to a subject using standard delivery or transfusion techniques.

Alternatively, the viruses comprising a heterologous nucleic acid can be delivered to the cells of a subject in vivo. Such methods may involve the administration of vector particles to a target cell population (e.g., blood cells, skin cells, liver cells, neural (including brain) cells, kidney cells, uterine cells, muscle cells, intestinal cells, cervical cells, vaginal cells, prostate cells, etc., as well as tumor cells derived from a variety of cells, tissues and/or organs. Administration can be either systemic, e.g., by intravenous administration of viral particles, or by delivering the viral particles directly to a site or sites of interest by a variety of methods, including injection (e.g., using a needle or syringe), needleless vaccine delivery, topical administration, or pushing into a tissue, organ or skin site. For example, the viral vector particles can be delivered by inhalation, orally, intravenously, subcutaneously, subdermally, intradermally, intramuscularly, intraperitoneally, intrathecally, by vaginal or rectal administration, or by placing the viral particles within a cavity or other site of the body, e.g., during surgery.

The methods and viruses encompassed by the present invention can be used to therapeutically or prophylactically treat a wide variety of disorders, including genetic and acquired disorders, e.g., as vaccines for infectious diseases, due to viruses, bacteria, and the like.

Kits

To facilitate use of the vectors and influenza viruses encompassed by the invention any of these, and additional components, such as, buffer, cells, culture medium, useful for packaging and infection of influenza viruses for experimental or therapeutic purposes, can be packaged in the form of a kit. The kit may contain, in addition to the above components, additional materials, e.g., instructions for performing the methods of the invention, packaging material, and a container.

Manipulation of Viral Nucleic Acids and Proteins

In the context of the invention, influenza virus nucleic acids and/or proteins are manipulated according to well known molecular biology techniques. Detailed protocols for numerous such procedures, including amplification, cloning, mutagenesis, transformation, and the like, are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomeli et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies including mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (mcrc@oligos.com), The Great American Gene Company (www.genco.com), ExpressGen, Inc. (www.expressgen.com), Operon Technologies, Inc. (www.operon.com), and many others.

In addition, substitutions of selected amino acid residues in viral polypeptides can be accomplished by, e.g., site directed mutagenesis. For example, viral polypeptides with amino acid substitutions functionally correlated with desirable phenotypic characteristic, e.g., an attenuated phenotype, cold adaptation, temperature sensitivity, can be produced by introducing specific mutations into a viral nucleic acid segment encoding the polypeptide. Methods for site directed mutagenesis are well known in the art, and described, e.g., in Ausubel, Sambrook, and Berger, supra. Numerous kits for performing site directed mutagenesis are commercially available, e.g., the Chameleon Site Directed Mutagenesis Kit (Stratagene, La Jolla), and can be used according to the manufacturers instructions to introduce, e.g., one or more amino acid substitutions described in Table 6 or Table 17, into a genome segment encoding a influenza A or B polypeptide, respectively.

SPECIFIC EMBODIMENTS

1. A method of preparing an HA glycosylated influenza B virus having increased replication in eggs comprising:
    (a) introducing a mutation resulting in an amino acid substitution at HA position 141 to arginine in an influenza B virus genome; and
    (b) replicating the mutated influenza virus genome under conditions whereby influenza B virus is produced.
2. The method of embodiment 2 wherein the step of introducing is performed by site-directed mutagenesis.
3. A method of preparing an HA glycosylated influenza B virus having increased replication in eggs comprising:
    (a) introducing into a population of host cells a plurality of vectors, said vectors comprising nucleotide sequences corresponding to:
        (i) at least 6 internal genome segments of a first influenza B strain; and
        (ii) one or more genome segments encoding HA and NA polypeptides of at least a second influenza B strain, wherein the HA polypeptide comprises an arginine at amino acid residue 141;

(b) culturing the population of host cells at a temperature that does not exceed 35 degrees; and
(c) recovering the influenza virus.

4. The method of embodiment 3 further comprising, prior to step (i):
introducing a mutation in one vector of the plurality of vectors,
wherein the one vector comprises nucleotide sequences corresponding to the genome segment encoding HA, and
wherein the mutation results in the arginine at amino acid residue 141.

5. The method of embodiment 3 or 4 wherein the first influenza B virus has one of the following attributes: temperature sensitivity, attenuation, or cold-adaptation.

6. The method of any one of embodiments 3-5 wherein the first influenza B virus comprises amino acid residues: PB2630 (630R); PA431 (431M); PA497 (497H); NP55 (55A); NP114 (114A); NP410 (410H); NP510 (510T); M1159 (159Q) and M1183 (183V).

7. The method of embodiment 6 further comprising a step of:
introducing mutations in vectors of the plurality of vectors, wherein the vectors comprise nucleotide sequences corresponding to the 6 internal genome segments of the first influenza B strains,
wherein the mutations result in presence of the amino acid residues PB2630 (630R); PA431 (431M); PA497 (497H); NP55 (55A); NP114 (114A); NP410 (410H); NP510 (510T); M1159 (159Q) and M1183 (183V).

8. The method of any one of embodiments 3-7 wherein the first influenza B virus is strain B/Ann Arbor/1/66.

9. The method of any one of embodiments 3-8 wherein the cells are one of Vero cells, Per.C6 cells, BHK cells, PCK cells, MDCK cells, MDBK cells, 293 cells, or COS cells.

10. The method of any one of embodiments 3-9 wherein the vectors are plasmids.

11. The method of any one of embodiments 3-10 wherein the plurality comprises sets of eight plasmids, wherein each of the eight plasmids comprises a nucleotide sequence corresponding to a different genome segment of the first or the second influenza B strain.

12. The method of any one of embodiments 3-11 wherein each plasmid of the plurality comprises all the nucleotide sequences.

13. The method of any one of embodiments 3-12, wherein the method does not comprise employing a helper virus.

14. The method of any one of embodiments 3-13 wherein the step of introducing is performed by lipid-mediated transfection or electroporation.

15. The method of any one of embodiments 3-14 where the temperature is between 30 and 35 degrees.

16. The method of any one of embodiments 3-15 wherein the temperature is between 32 and 35 degrees.

17. The method of any one of embodiments 3-16 further comprising replicating the recovered influenza virus on eggs; wherein the influenza virus replicated on eggs retains the HA amino acid residue position 196/197 glycosylation site; and wherein the influenza virus replicates to at least a peak titer of 7.0 log 10 PFU/ml on the eggs.

18. An influenza B virus prepared by the method of any one of embodiments 1-17.

19. An immunogenic composition comprising the influenza B virus of embodiment 18.

20. A vaccine comprising the influenza B virus of embodiment 19.

21. The vaccine of embodiment 20 which is suitable for intranasal administration.

22. The method of any one of embodiments 3-17 further comprising:
killing the recovered virus.

23. The method of embodiment 1 or 2 further comprising:
a) recovering the influenza virus; and
b) killing the recovered virus.

24. A live attenuated influenza B virus vaccine comprising the virus produced by the method of any one of embodiments 1-17.

24. A method of treatment of viral infection in a subject comprising:
administering to the subject the virus produced by the method of any one of embodiments 1-17 in an amount effective to produce an immunogenic response against the viral infection.

EXAMPLES

Example 1

Construction of pAD3000

The plasmid pHW2000 (Hoffmann et al. (2000) *A DNA transfection system for generation of influenza A virus from eight plasmids Proc Natl Acad Sci USA* 97:6108-6113) was modified to replace the bovine growth hormone (BGH) polyadenylation signals with a polyadenylation signal sequences derived from Simian virus 40 (SV40).

Sequences derived from SV40 were amplified with Taq MasterMix (Qiagen) using the following oligonucleotides, designated in the 5' to 3' direction:

```
                                            (SEQ ID NO: 1)
polyA.1:  AACAATTGAGATCTCGGTCACCTCAGACATGATAAGATAC
          ATTGATGAGT (SEQ ID NO: 2)
polyA.2:  TATAACTGCAGACTAGTGATATCCTTGTTTATTGCAGCTT
          ATAATGGTTA
```

The plasmid pSV2H is was used as a template. A fragment consistent with the predicted 175 bp product was obtained and cloned into pcDNA3.1, using a Topo TA cloning vector (Invitrogen) according to the manufacturer's directions. The desired 138 bp fragment containing the SV40 polyadenylation signals was excised from the resulting plasmid with EcoRV and BstEII, isolated from an agarose gel, and ligated between the unique PvuII and BstEII sites in pHW2000 using conventional techniques (see, e.g., Ausubel, Berger, Sambrook). The resulting plasmid, pAD3000 (FIG. 1), was sequenced and found to contain the SV40 polyadenylation site in the correct orientation. Nucleotides 295-423 in pAD3000 correspond to nucleotides 2466-2594, respectively, in SV40 strain 777 (AF332562).

Example 2

Eight Plasmid System for Production of MDV-B

Viral RNA from a cold adapted variant of influenza B/Ann Arbor/1/66 (ca/Master Ann Arbor/1/66 P1 Aviron 10/2/97), an exemplary influenza B master donor strain (MDV-B) was extracted from 100 µl of allantoic fluid from infected embryonated eggs using the RNeasy Kit (Qiagen, Valencia, Calif.), and the RNA was eluted into 40 µl H$_2$0. RT-PCR of genomic segments was performed using the One Step RT-PCR kit (Qiagen, Valencia, Calif.) according to the protocol provided, using 1 µl of extracted RNA for each reaction. The RT-reaction was performed 50 min at 50° C., followed by 15 min at 94° C. The PCR was performed for 25 cycles at 94° C. for 1 min, 54° C. for 1 min, and 72° C. for 3 min. The P-genes were amplified using segment specific primers with BsmBI-sites that resulted in the generation of two fragments (Table 1).

TABLE 1

RT-PCR primers for amplification of the eight vRNAs of influenza ca B/Ann Arbor/1/66.

| | Forward primer | Reverse primer |
|---|---|---|
| PB1 [1A] | Bm-PB1b-1: (SEQ ID NO: 14)<br>TATTCGTCTCAGGGAGCAGAAGCGGAGCCTTTAAGATG | Bm-PB1b-1200R: (SEQ ID NO:15)<br>TATTCGTCTCGATGCCGTTCCTTCTTCATTGAAGAATGG |
| PB1 [1B] | Bm-PB1b-1220: (SEQ ID NO: 16)<br>TATTCGTCTCGGCATCTTTGTCGCCTGGGATGATGATG | Bm-PB1b-2369R: (SEQ ID NO:17)<br>ATATCGTCTCGTATTAGTAGAAACACGAGCCTT |
| PB2 [2A] | Bm-PB2b-1: (SEQ ID NO: 18)<br>TATTCGTCTCAGGGAGCAGAAGCGGAGCGTTTTCAAGATG | Bm-PB2b-1145R: (SEQ ID NO:19)<br>TATTCGTCTCTCTCATTTTGCTCTTTTTTAATATTCCCC |
| PB2 [2B] | Bm-PB2b-1142: (SEQ ID NO: 20)<br>TATTCGTCTCATGAGAATGGAAAAAC-TACTAATAAATTCAGC | Bm-PB2b-2396R: (SEQ ID NO:21)<br>ATATCGTCTCGTATTAGTAGAAACACGAGCATT |
| PA [3A] | Bm-Pab-1: (SEQ ID NO: 22)<br>TATTCGTCTCAGGGAGCAGAAGCGGTGCGTTTGA | Bm-PAb-1261R: (SEQ ID NO:23)<br>TATTCGTCTCCCAGGGCCCTTTTACTTGTCAGAGTGC |
| PA [3B] | Bm-Pab-1283: (SEQ ID NO: 24)<br>TATTCGTCTCTCCTGGATCTACCAGAAATAGGGCCAGAC | Bm-PAb-2308R: (SEQ ID NO:25)<br>ATATCGTCTCGTATTAGTAGAAACACGTGCATT |
| HA | MDV-B 5'BsmBI-HA: (SEQ ID NO: 26)<br>TATTCGTCTCAGGGAGCAGAAGCAGAGCATTTTCTAATATC | MDV-B 3'BsmBI-HA: (SEQ ID NO:27)<br>ATATCGTCTCGTATTAGTAGTAACAAGAGCATTTTTC |
| NP | Ba-NPb-1: (SEQ ID NO: 28)<br>TATTGGTCTCAGGGAGCAGAAGCACAGCATTTTCTTGT | Ba-NPb-1842R: (SEQ ID NO:29)<br>ATATGGTCTCGTATTAGTAGAAACAACAGCATTTTT |
| NA | MDV-B 5'BsmBI-NA: (SEQ ID NO: 30)<br>TATTCGTCTCAGGGAGCAGAAGCAGAGCATCTTCTCAAAAC | MDV-B 3'BsmBI-NA: (SEQ ID NO:31)<br>ATATCGTCTCGTATTAGTAGTAACAAGAGCATTTTTCAG |
| M | MDV-B 5'BsmBI-M: (SEQ ID NO: 32)<br>TATTCGTCTCAGGGAGCAGAAGCACGCACTTTCTTAAAATG | MDV-B 3'BsmBI-M: (SEQ ID NO:33)<br>ATATCGTCTCGTATTAGTAGAAACAACGCACTTTTTCCAG |
| NS | MDV-B 5'BsmBI-NS: (SEQ ID NO: 34)<br>TATTCGTCTCAGGGAGCAGAAGCAGAGGATTTGTTTAGTC | MDV-B 3'BsmBI-NS: (SEQ ID NO:35)<br>ATATCGTCTCGTATTAGTAGTAACAAGAGGATTTTTAT |

The sequences complementary to the influenza sequences are shown in bold. The 5'-ends have recognition sequences for the restriction endonucleases BsmBI (Bm) or BsaI (Ba).

Cloning of Plasmids

PCR fragments were isolated, digested with BsmBI (or BsaI for NP) and inserted into pAD3000 (a derivative of pHW2000 which allows the transcription of negative sense vRNA and positive mRNA) at the BsmBI site as described above. Two to four each of the resultant plasmids were sequenced and compared to the consensus sequence of MDV-B based on sequencing the RT-PCR fragments directly. Plasmids which had nucleotide substitutions resulting in amino acid changes different from the consensus sequence were "repaired" either by cloning of plasmids or by utilizing the Quikchange kit (Stratagene, La Jolla, Calif.). The resultant B/Ann Arbor/1/66 plasmids were designated pAB 121-PB 1, pAB 122-PB2, pAB 123-PA, pAB 124-HA, pAB 125-NP, pAB126-NA, pAB127-M, and pAB128-NS. Using this bi-directional transcription system all viral RNAs and proteins are produced intracellularly, resulting in the generation of infectious influenza B viruses (FIG. 2).

It is noteworthy that pAB121-PB1 and pAB124-HA had 2 and pAB128-NS had 1 silent nucleotide substitution compared to the consensus sequence (Table 2). These nucleotide changes do not result in amino acid alterations, and are not anticipated to affect viral growth and rescue. These silent substitutions have been retained to facilitate genotyping of the recombinant viruses.

TABLE 2

Plasmid Set Representing The Eight Segments of B/Ann Arbor/1/66 (MDV-B)

| Seg. | plasmids | nucleotides | protein |
|---|---|---|---|
| PB1 | PAB121-PB1 | A924 > G924; C1701 > T1701 | silent |
| PB2 | PAB122-PB2 | consensus | — |
| PA | PAB123-PA | consensus | — |
| HA | PAB124-HA | T150 > C150; T153 > C153 | silent |
| NP | PAB125-NP | consensus | — |
| NA | PAB126-NA | consensus | — |
| M | PAB127-M | consensus | — |
| NS | PAB128-NS | A416 > G416 | NS1: silent |

For construction of the plasmids with nucleotide substitution in PA, NP, and M1 genes the plasmids pAB123-PA, pAB125-NP, pAB127-M were used as templates. Nucleotides were changed by Quikchange kit (Stratagene, La Jolla, Calif.). Alternatively, two fragments were amplified by PCR using primers which contained the desired mutations, digested with BsmBI and inserted into pAD3000-BsmBI in a three fragment ligation reaction. The generated plasmids were sequenced to ensure that the cDNA did not contain unwanted mutations.

The sequence of template DNA was determined by using Rhodamine or dRhodamine dye-terminator cycle sequencing ready reaction kits with AmpliTaq® DNA polymerase FS (Perkin-Elmer Applied Biosystems, Inc, Foster City, Calif.). Samples were separated by electrophoresis and analyzed on PE/ABI model 373, model 373 Stretch, or model 377 DNA sequencers.

In a separate experiment, viral RNA from influenza B/Yamanshi/166/98 was amplified and cloned into pAD3000 as described above with respect to the MDV-B strain, with the exception that amplification was performed for 25 cycles at 94° C. for 30 seconds, 54° C. for 30 seconds and 72° C. for 3 minutes. Identical primers were used for amplification of the B/Yamanashi/166/98 strain segments, with the substitution of the following primers for amplification of the NP and NA segments: MDV-B 5'BsmBI-NP: TATTCGTCTCAGGGAG-CAGAAGCACAGCATTTTCTTGTG (SEQ ID NO:36) and MDV-B 3'BsmBI-NP:ATATCGTCTCGTATTAGTAGAAA-CAACAGCATTTTTTAC (SEQ ID NO:37) and Bm-NAb-1: TATTCGTCTCAGGGAGCAGAAGCAGAGCA (SEQ ID NO:38) and Bm-NAb-1557R:ATATCGTCTCGTATTAG-TAGTAACAAGAGCA TTTT (SEQ ID NO:39), respectively. The B/Yamanashi/166/98 plasmids were designated pAB251-PB1, pAB252-PB2, pAB253-PA, pAB254-HA, pAB255-NP, pAB256-NA, pAB257-M, and pAB258-NS. Three silent nucleotide differences were identified in PA facilitating genotyping of recombinant and reassortant B/Yamanishi/166/98 virus.

Example 3

Generation of Infectious Recombinant Influenza B and Reassorted Influenza Virus

Infectious recombinant influenza B viruses were produced by co-culturing 293T or COS-7 cells (primate cells with high transfection efficiency and polI activity) with MDCK cells (permissive for influenza virus). 293T cells were maintained in OptiMEM I-AB medium containing 5% FBS cells, COS-7 cells were maintained in DMEM I-AB medium containing 10% FBS. MDCK cells were maintained in 1×MEM, 10% FBS with the addition of antibiotic and antimycotic agents. Prior to transfection with the viral genome vectors, the cells were washed once with 5 ml PBS or medium without FBS. Ten ml trypsin-EDTA was added to confluent cells in a 75 cm² flask (MDCK cells were incubated for 20-45 min, 293T cells were incubated for 1 min) The cells were centrifuged, and resuspended in 10 ml OptiMEM I-AB. One ml of each suspended cell line was then diluted into 18 ml OptiMEM I-AB, and mixed. The cells were then aliquoted into a 6 well plate at 3 ml/well. After 6-24 hours, 1 ng of each plasmid was mixed in an 1.5 ml Eppendorf tube with OptiMEM I-AB to the plasmids (x µl plasmids+x µl OptiMEM I-AB+x µl TransIT-LT1=200 µl); 2 µl TransIT-LT1 per µg of plasmid DNA. The mixture was incubated at room temperature for 45 min. Then 800 µl of OptiMEM I-AB was added. The medium was removed from the cells, and the transfection mixture was added to the cells (t=0) at 33° C. for 6-15 hours. The transfection mixture was slowly removed from the cells, and 1 ml of OptiMEM I-AB was added, and the cells were incubated at 33° C. for 24 hours. Forty-eight hours following transfection, 1 ml of OptiMEM I-AB containing 1 µg/ml TPCK-trypsin was added to the cells. At 96 hours post-transfection, 1 ml of OptiMEM I-AB containing 1 µg/ml TPCK-trypsin was added to the cells.

Between 4 days and 7 days following transfection 1 ml of the cell culture supernatant was withdrawn and monitored by HA or plaque assay. Briefly, 1 ml of supernatant was aliquoted into an Eppendorf tube and centrifuge at 5000 rpm for 5 min. Nine hundred µl of supernatant was transferred to a new tube, and serial dilutions were performed at 500 µl/well to MDCK cells (e.g., in 12 well plates). The supernatant was incubated with the cells for 1 hour then removed, and replaced with infection medium (1×MEM) containing 1 µg/ml of TPCK-trypsin. HA assay or plaque assays were then performed. For example, for the plaque assays supernatants were titrated on MDCK cells which were incubated with an 0.8% agarose overlay for three days at 33° C. For infection of eggs the supernatant of transfected cells were harvested six or seven days after transfection, 100 µl of the virus dilutions in Opti-MEM I were injected into 11 days old embryonated chicken eggs at 33° C. The titer was determined three days after inoculation by $TCID_{50}$ assay in MDCK cells.

To generate MDV-B, either co-cultured 293T-MDCK or COS-7-MDCK cells were transfected with 1 µg of each plasmid. When examined at 5 to 7 days post-transfection the co-cultured MDCK cells showed cytopathic effects (CPE), indicating the generation of infectious MDV-B virus from cloned cDNA. No CPE was observed in cells transfected with seven plasmids (Table 3). To determine the efficiency of the DNA transfection system for virus generation, supernatants of cells were titrated seven days after transfection on MDCK cells and the virus titer was determined by plaque assay. The virus titer of the supernatant of co-cultured 293T-MDCK was $5.0 \times 10^6$ pfu/ml and $7.6 \times 10^6$ pfu/ml in COST-MDCK cells.

TABLE 3

Generation of infectious Influenza-B virus from eight plasmids

| | segment | | | |
|---|---|---|---|---|
| | 1 | 2 | 3 | 4 |
| PB1 | pAB121-PB1 | — | PAB121-PB1 | — |
| PB2 | pAB122-PB2 | pAB122-PB2 | PAB122-PB2 | pAB122-PB2 |
| PA | pAB123-PA | pAB123-PA | pAB123-PA | pAB123-PA |
| HA | pAB124-HA | pAB124-HA | pAB124-HA | pAB124-HA |
| NP | pAB125-NP | pAB125-NP | pAB125-NP | pAB125-NP |
| NA | pAB126-NA | pAB126-NA | pAB126-NA | pAB126-NA |
| M | pAB127-M | pAB127-M | pAB127-M | pAB127-M |
| NS | pAB128-NS | pAB128-NS | pAB128-NS | pAB128-NS |

| | co-cultured 293T-MDCK cells | | co-cultured COS-7-MDCK cells | |
|---|---|---|---|---|
| CPE | + | − | + | − |
| pfu/ml | $5.0 \times 10^6$ | 0 | $7.6 \times 10^6$ | 0 |

Transiently co-cultured 293T-MDCK (1, 2) or co-cultured COST-MDCK cells (3, 4) were transfected with seven or eight plasmids. Cytopathic effect (CPE) was monitored seven days after transfection in the co-cultured MDCK cells. Seven days after transfection the supernatants of transfected cells were titrated on MDCK cells. The data of pfu/ml represent the average of multiple, (e.g., three or four) transfection experiments.

Comparable results were obtained in transfection experiments utilizing the B/Yamanashi/166/98 plasmid vectors. These results show that the transfection system allows the reproducible de novo generation of influenza B virus from eight plasmids.

Genotyping of Recombinant Influenza B

Figure 3A:
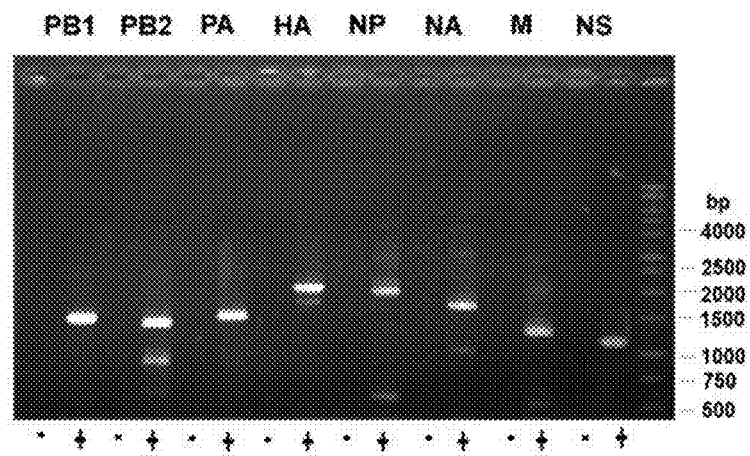
Figure 3B:
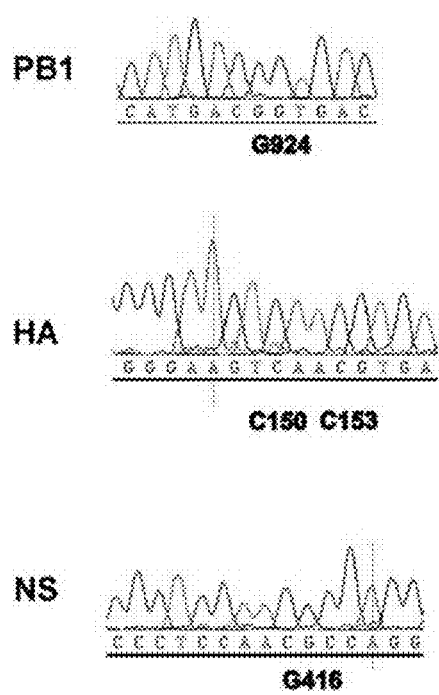

After a subsequent passage on MDCK cells, RT-PCR of the supernatant of infected cells was used to confirm the authenticity of the generated virus. RT-PCR was performed with segment specific primers for all eight segments (Table 1). As shown in FIG. 3A, PCR products were generated for all segments. Direct sequencing of the PCR products of the PB1, HA, and NS segments revealed that the four nucleotides analyzed were the same as found in the plasmid pAB121-PB1, pAB124-HA, and pAB128-NS. These results confirmed that the generated virus was generated from the designed plasmids and exclude (in addition to the negative controls) any possible laboratory contamination with the parent virus (FIG. 3B).

Figure 3C:
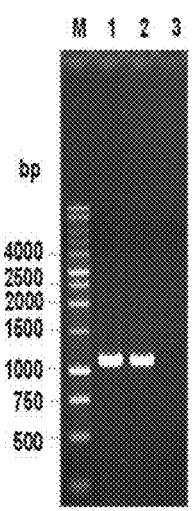

Similarly, following transfection with the B/Yamanashi/166/98 plasmid vectors, virus was recovered and the region encompassing nucleotides 1280-1290 of the PA segment were amplified. Sequencing confirmed that the recovered virus corresponded to the plasmid-derived recombinant B/Yamanashi/166/98 (FIGS. 3C and D).

Phenotyping of rMDV-B

The MDV-B virus shows two characteristic phenotypes: temperature sensitivity (ts) and cold adaptation (ca). By definition a 2 log(or higher) difference in virus titer at 37° C. compared to 33° C. defines ts, ca is defined by less than 2 log difference in virus growth at 25° C. compared to 33° C. Primary chicken kidney (PCK) cells were infected with the parent virus MDV-B and with the transfected virus derived from plasmids to determine the viral growth at three temperatures.

For plaque assay confluent MDCK cells (ECACC) in six well plates were used. Virus dilutions were incubated for 30-60 min. at 33° C. The cells were overlayed with an 0.8% agarose overlay. Infected cells were incubated at 33° C. or 37° C. Three days after infection the cells were stained with 0.1% crystal violet solution and the number of plaques determined.

Figure 2:
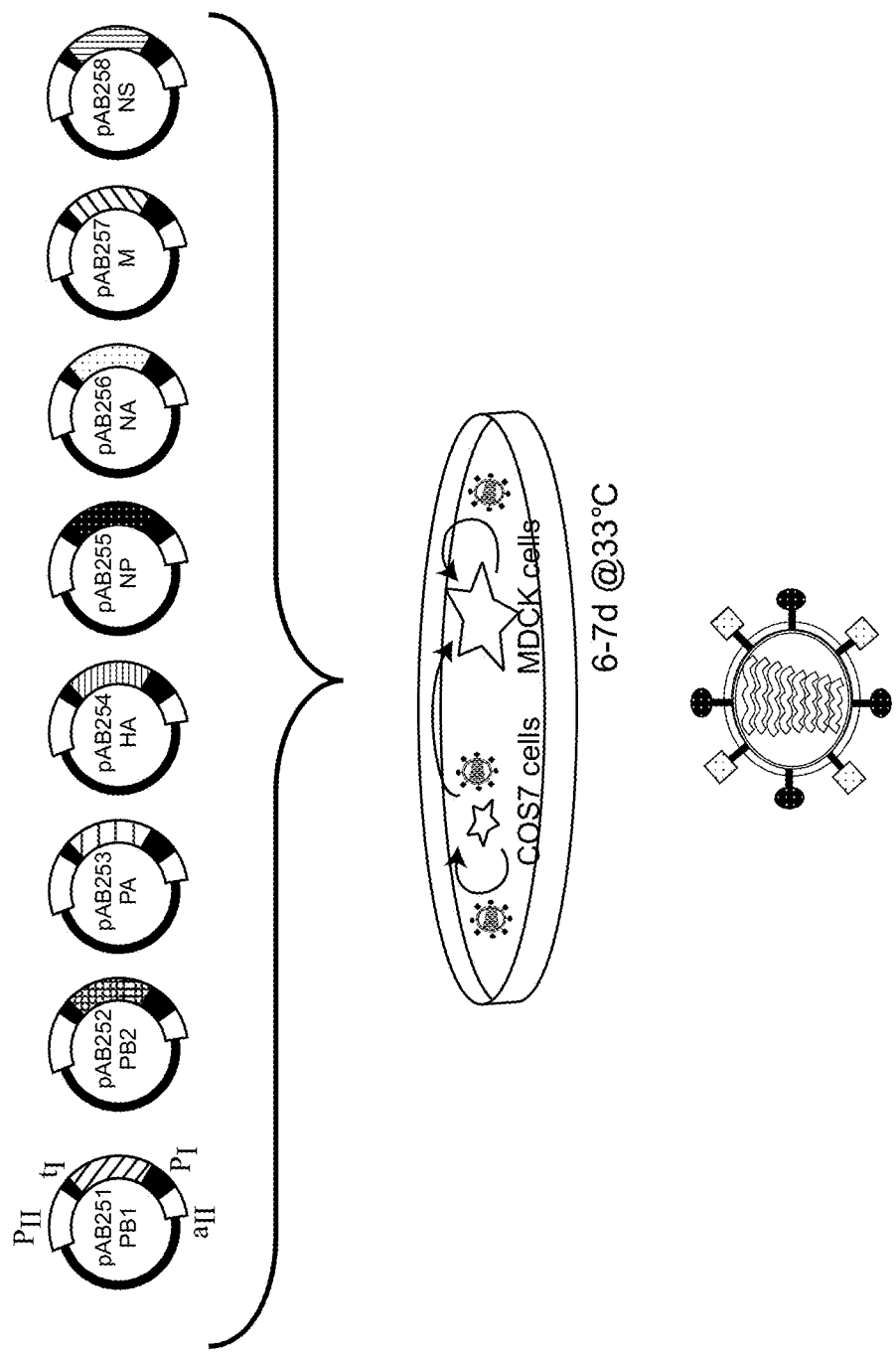
FIG. 2: Illustration of eight plasmid system for the production of influenza B virus.

The ca-ts phenotype assay was performed by $TCID_{50}$ titration of the virus samples at 25, 33, and 37° C. This assay format measures the $TCID_{50}$ titer by examining the cytopathic effect (CPE) of influenza virus on primary chick kidney cell monolayers in 96-well cell culture plates at different temperatures (25° C., 33° C., 37° C.). This assay is not dependent on the plaque morphology, which varies with temperature and virus strains; instead it is dependent solely on the ability of influenza virus to replicate and cause CPE. Primary chicken kidney (PCK) cell suspension, prepared by trypsinization of the primary tissue, were suspended in MEM (Earl's) medium containing 5% FCS. PCK cells were seeded in 96 well cell culture plates for 48 hours in order to prepare monolayer with >90% confluency. After 48 hrs, the PCK cell monolayer were washed for one hour with serum free MEM medium containing 5 mM L-Glutamine, antibiotics, non-essential amino acid, referred as Phenotype Assay Medium (PAM). Serial ten-fold dilution of the virus samples were prepared in 96 well blocks containing PAM. The diluted virus samples were then plated onto the washed PCK monolayer in the 96 well plates. At each dilution of the virus sample, replicates of six wells were used for infection with the diluted virus. Un-infected cells as cell control were included as replicate of 6 wells for each sample. Each virus sample was titered in 2-4 replicates. Phenotype control virus with pre-determined titers at 25° C., 33° C., and 37° C. is included in each assay. In order to determine the ts phenotype of the virus samples, the plates were incubated for 6 days at 33° C. and 37° C. in 5% $CO_2$ cell culture incubators. For ca-phenotype characterization the plates were incubated at 2° C. for 10 days. The virus titer was calculated by the Karber Method and reported as $Log_{10}$ Mean (n=4) $TCID_{50}$ Titer/ml±Standard Deviation. The standard deviations of the virus titers presented in FIG. 1-3 ranged from 0.1 to 0.3. The difference in virus titer at 33° C. and 37° C. were used to determine the ts phenotype and difference in titer at 25° C. and 33° C. of the virus were used to determine the ca phenotype.

The plasmid derived recombinant MDV-B (recMDV-B) virus expressed the two characteristic phenotypes in cell culture, ca and ts, as expected. The ca phenotype, efficient replication at 25° C., is functionally measured as a differential in titer between 25° C. and 33° C. of less than or equal to 2 log 10 when assayed on PCK cells. Both the parental MDV-B and recMDV-B expressed ca; the difference between 25° C. and 33° C. was 0.3 and 0.4 log 10, respectively (Table 4). The ts phenotype is also measured by observing the titers at two different temperatures on PCK cells; for this phenotype, however, the titer at 37° C. should be less than the titer at 33° C. by 2 log 10 or more. The difference between 33° C. and 37° C. for the parental MDV-B and recMDV-B was 3.4 and 3.7 log 10, respectively (Table 4). Thus, the recombinant plasmid-derived MDV-B virus expressed both the ca and ts phenotypes.

The recombinant virus had a titer of 7.0 $log_{10}$ $TCID_{50}$/ml at 33° C. and 3.3 $TCID_{50}$/ml at 37° C. and 8.8 $log_{10}$ $TCID_{50}$/ml at 25° C. (Table 4). Thus, the recombinant virus derived from transfection with the eight influenza MDV-B genome segment plasmids has both the ca and ts phenotype.

TABLE 4

Phenotype assay for MDV-B and rMDV-B generated from plasmids

| | Temperature (0 C.) | | | |
|---|---|---|---|---|
| | 25 | 33 | 37 | |
| Virus | Log10 TCID50/ml (Mean + SD) | | | Phenotype |
| ca B/Ann Arbor/01/66 (MDV-B) | 8.8 + 0.3 | 8.5 + 0.05 | 5.1 + 0.1 | ca, ts |
| RecMDV-B | 7.4 + 0.3 | 7.0 + 0.13 | 3.3 + 0.12 | ca, ts |
| Rec53-MDV-B | 5.9 + 0.1 | 5.7 + 0.0 | 5.3 + 0.1 | ca, non-ts |

Primary chicken kidney cells were infected with the parent virus MDV-B and the plasmid-derived recombinant virus (recMDV-B). The virus titer was determined at three different temperatures.

Example 7

Production of Reassortant B/Yamanashi/166/98 Virus

Figure 6:
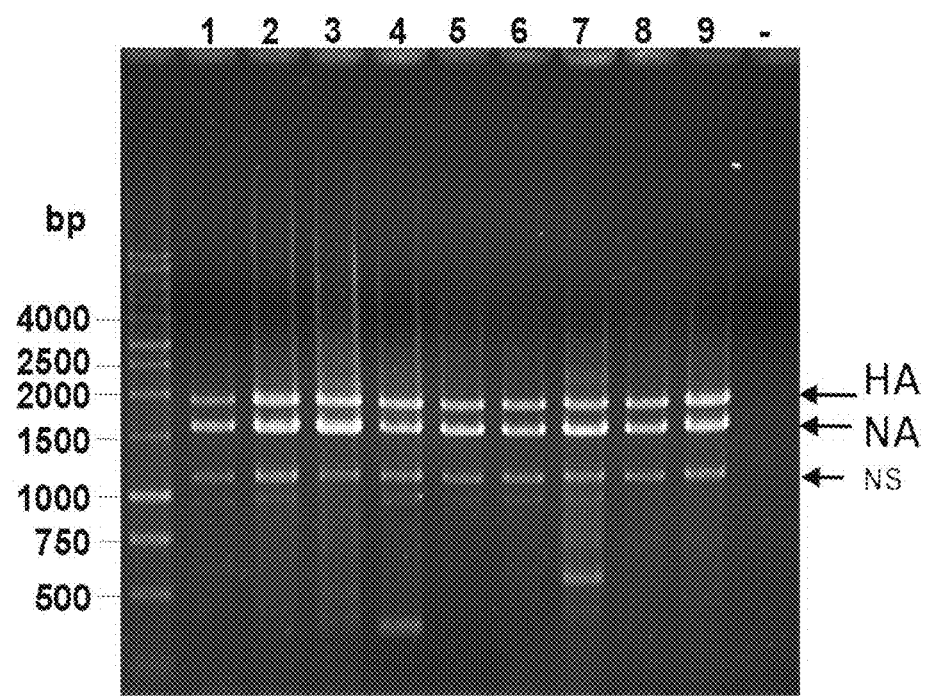
FIG. 6: RT-PCR products derived from simultaneous amplification of HA and NA segments of influenza B strains.

The HA and NA segments of several different strains representing the major lineages of influenza B were amplified and cloned into pAD3000, essentially as described above. The primers were optimized for simultaneous RT-PCR amplification of the HA and NA segments. Comparison of the terminal regions of the vRNA representing the non coding region of segment 4 (HA) and segment 6 (NB/NA) revealed that the 20 terminal nucleotides at the 5' end and 15 nucleotides at the 3' end were identical between the HA and NA genes of influenza B viruses. A primer pair for RT-PCR (italicized sequences are influenza B virus specific) Bm-NAb-1: TAT TCG TCT CAG GGA GCA GAA GCA GAG CA (SEQ ID NO:38); Bm-NAb-1557R: ATA TCG TCT CGT ATT AGT AGT AAC AAG AGC ATT TT (SEQ ID NO:39) was synthesized and used to simultaneously amplify the HA and NA genes from various influenza B strains (FIG. 6). The HA and NA PCR-fragments of B/Victoria/504/2000, B/Hawaii/10/2001, and B/Hong Kong/330/2001 were isolated, digested with BsmBI and inserted into pAD3000. These results demonstrated the applicability of these primers for the efficient generation of plasmids containing the influenza B HA and NA genes from several different wild type viruses representing the major lineages of influenza B. The RT-PCR products can be used for sequencing and/or cloning into the expression plasmids.

In order to demonstrate the utility of B/Yamanashi/166/98 (a B/Yamagata/16/88-like virus) to efficiently express antigens from various influenza B lineages, reassortants containing PB1, PB2, PA, NP, M, NS from B/Yamanashi/166/98 and the HA and NA from strains representing both the Victoria and Yamagata lineages (6+2 reassortants) were generated. Transiently cocultured COS7-MDCK cells were cotransfected with six plasmids representing B/Yamanashi/166/98 and two plasmids containing the cDNA of the HA and NA segments of two strains from the B/Victoria/2/87 lineage, B/Hong Kong/330/2001 and B/Hawaii/10/2001, and one strain from the B/Yamagata/16/88 lineage, B/Victoria/504/2000, according to the methods described above. Six to seven days after transfection the supernatants were titrated on fresh MDCK cells. All three 6+2 reassortant viruses had titers between 4-9×10$^6$ pfu/ml (Table 5). These data demonstrated that the six internal genes of B/Yamanashi/166/98 could efficiently form infectious virus with HA and NA gene segments from both influenza B lineages.

Supernatants of cocultured COST-MDCK cells were titrated six or seven days after transfection and the viral titer determined by plaque assays on MDCK cells.

TABLE 5

Plasmid set used for the generation of B/Yamanashi/166/98 and 6 + 2 reassortants.

| segment | | | | | |
|---|---|---|---|---|---|
| 1 | — | pAB251-PB1 | pAB251-PB1 | pAB251-PB1 | pAB251-PB1 |
| 2 | pAB252-PB2 | pAB252-PB2 | pAB252-PB2 | pAB252-PB2 | pAB252-PB2 |
| 3 | pAB253-PA | pAB253-PA | pAB253-PA | pAB253-PA | pAB253-PA |
| 4 | pAB254-HA | pAB254-HA | pAB281-HA | pAB285-HA | pAB287-HA |
| 5 | pAB255-NP | pAB255-NP | pAB255-NP | pAB255-NP | pAB255-NP |
| 6 | pAB256-NA | pAB256-NA | pAB291-NA | pAB295-NA | pAB297-NA |
| 7 | pAB257-M | pAB257-M | pAB257-M | pAB257-M | pAB257-M |
| 8 | pAB258-NA | pAB258-NA | pAB258-NA | pAB258-NA | pAB258-NA |

| | Recombinant virus | | | |
|---|---|---|---|---|
| | 8 B/Yamanashi/ 166/98 | 6 + 2 B/Victoria/ 504/2000 | 6 + 2 B/Hawaii/ 10/2001 | 6 + 2 B/Hong Kong/ 330/2001 |
| pfu/ml$^a$ | 0 | 4 × 10$^6$ | 9 × 10$^6$ | 6 × 10$^6$ | 7 × 10$^6$ |

Figure 7:
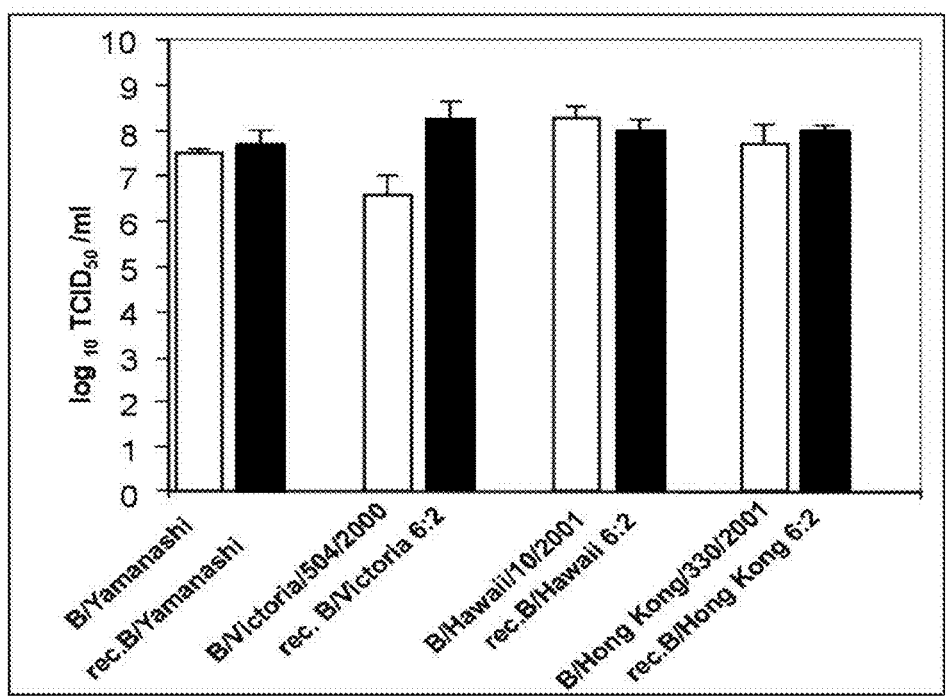
FIG. 7: Bar graph illustrating relative titers of recombinant and reassortant virus.

Relatively high titers are obtained by replication of wild type B/Yamanashi/166/98 in eggs. Experiments were performed to determine whether this property was an inherent phenotype of the six "internal" genes of this virus. To evaluate this property, the yield of wild type B/Victoria/504/2000, which replicated only moderately in eggs, was compared to the yield of the 6+2 reassortant expressing the B/Victoria/504/2000 HA and NA. These viruses in addition to wild type and recombinant B/Yamanashi/166/98 were each inoculated into 3 or 4 embryonated chicken eggs, at either 100 or 1000 pfu. Three days following infection, the allantoic fluids were harvested from the eggs and the TCID$_{50}$ titers determined on MDCK cells. The 6+2 reassortants produced similar quantities of virus in the allantoic fluid to the wt and recombinant B/Yamanashi/166/98 strain (FIG. 7). The difference in titer between B/Victoria/504/2000 and the 6+2 recombinant was approximately 1.6 log$_{10}$ TCID$_{50}$ (0.7-2.5 log$_{10}$ TCID$_{50}$/mL, 95% CI). The difference between B/Victoria/504/2000 and the 6+2 recombinant were confirmed on three separate experiments (P<0.001). These results demonstrated that the egg growth properties of B/Yamanashi/166/98 could be conferred to HA and NA antigens that are normally expressed from strains that replicated poorly in eggs.

Example 8

Molecular Basis for Attenuation of Ca B/Ann Arbor/1/66

The MDV-B virus (ca B/Ann Arbor/1/66) is attenuated in humans, shows an attenuated phenotype in ferrets and shows a cold adapted and temperature sensitive phenotype in cell culture. The deduced amino acid sequences of the internal genes of MDV-B were compared with sequences in the Los Alamos influenza database (on the world wide web at: flu.lanl.gov) using the BLAST search algorithm. Eight amino acids unique to MDV-B, and not present in any other strain were identified (Table 6). Genome segments encoding PB1, BM2, NS1, and NS2 show no unique substituted residues. The PA and M1 proteins each have two, and the NP protein has four unique substituted amino acids (Table 6). One substituted amino acid is found in PB2 at position 630 (an additional strain B/Harbin/7/94 (AF170572) also has an arginine residue at position 630).

These results suggested that the gene segments PB2, PA, NP and M1 may be involved in the attenuated phenotype of MDV-B. In a manner analogous to that described above for MDV-A, the eight plasmid system can be utilized to generate recombinant and reassortant (single and/or double, i.e., 7:1; 6:2 reassortants) in a helper independent manner simply by co-transfection of the relevant plasmids into cultured cells as described above with respect to MDV-A. For example, the 6 internal genes from B/Lee/40 can be used in conjunction with HA and NA segments derived from MDV-B to generate 6+2 reassortants.

TABLE 6

Unique substituted amino acids of B/Ann Arbor/1/66

| | | | ca B/Ann Arbor/ 1/66 | | Aligned sequences (wild type viruses) | | Number of aligned sequences |
|---|---|---|---|---|---|---|---|
| | Nr. | pos. | amino acid | codon | amino acid | codon | |
| PB1 | 0 | | — | | — | | 23 |
| PB2 | 1 | 630 | Arg630 | AGA | Ser630 | AGC | 23 |
| PA | 2 | 431 | Met431 | ATG | Val431 | GTG | 23 |
| | | 497 | His497 | CAT | Tyr497 | TAT | |
| NP | 4 | 55 | Ala55 | GCC | Thr55 | ACC | 26 |
| | | 114 | Ala114 | GCG | Val114 | GTG | |
| | | 410 | His410 | CAT | Pro410 | CCT, CCC | |
| | | 509 | Thr509 | GAC | Ala509 | GGC | |

TABLE 6-continued

Unique substituted amino acids of B/Ann Arbor/1/66

|  | Nr. | pos. | ca B/Ann Arbor/1/66 amino acid | codon | Aligned sequences (wild type viruses) amino acid | codon | Number of aligned sequences |
|---|---|---|---|---|---|---|---|
| M1 | 2 | 159 | Gln159 | CAA | His159 | CAT | 24 |
|  |  | 183 | Val183 | GTG | M183 | ATG |  |
| BM2 | 0 |  | — |  | — |  | 24 |
| NS1 | 0 |  | — |  | — |  | 80 |
| NS2 | 0 |  | — |  | — |  | 80 |

The deduced amino acid sequence of eight proteins of ca B/Ann Arbor was used in a BLAST search Amino acid position which were different between MDV-B and the aligned sequences are shown. The nucleotides in the codons that are underlined represent the substituted positions.

In order to determine whether the 8 unique amino acid differences had any impact on the characteristic MDV-B phenotypes, a recombinant virus was constructed in which all eight nucleotide positions encoded the amino acid reflecting the wt influenza genetic complement. A set of plasmids was constructed in which the eight residues of the PA, NP, and M1 genes were changed by site directed mutagenesis to reflect the wild type amino acids (as indicated in Table 6). A recombinant with all eight changes, designated rec53-MDV-B, was generated by cotransfection of the constructed plasmids onto cocultured COST-MDCK cells. The coculturing of MDCK cells and growth at 33° C. ensured that the supernatant contained high virus titers six to seven days after transfection. The supernatants of the transfected cells were titrated and the titer determined on MDCK cells by plaque assay and PCK cells at 33° C. and 37° C.

As shown in FIG. 8, in two different independent experiments, recMDV-B expressed the ts-phenotype in both MDCK cells and PCK cells. The triple reassortant virus rec53-MDV-B designed harboring all eight amino acid changes expressed the non-ts-phenotype, the difference in titer between 33° C. and 37° C. was only 0.7 $\log_{10}$ in PCK cells. This titer was less than the required 2 $\log_{10}$ difference characteristic of the ts definition and significantly lower than the ~3 $\log_{10}$ difference observed with recMDV-B. These results show that the alteration of the eight amino acids within PA, NP, and M1 proteins was sufficient to generate a non-ts, wild type-like virus with both homologous and heterologous glycoproteins.

The contribution of each gene segment to the ts phenotype was then determined Plasmid derived recombinants harboring either the PA, NP, or M gene segment with the wild-type amino acid complement were generated by the DNA cotransfection technique. All single gene recombinants exhibited growth restriction at 37° C. in MDCK cells and in PCK cells (FIG. 9), indicating that changes in no one gene segment were capable of reverting the ts phenotype. In addition, recombinant viruses that carried both the NP and M or PA and M gene segments together also retained the ts-phenotype. In contrast, recombinant viruses that harbored both the PA and NP gene segments had a difference in titer between 37° C. and 33° C. of 2.0 $\log_{10}$ or less, similar to the rec53-MDV-B. These results show that the NP and PA genes have a major contribution to the ts-phenotype.

Figure 11:
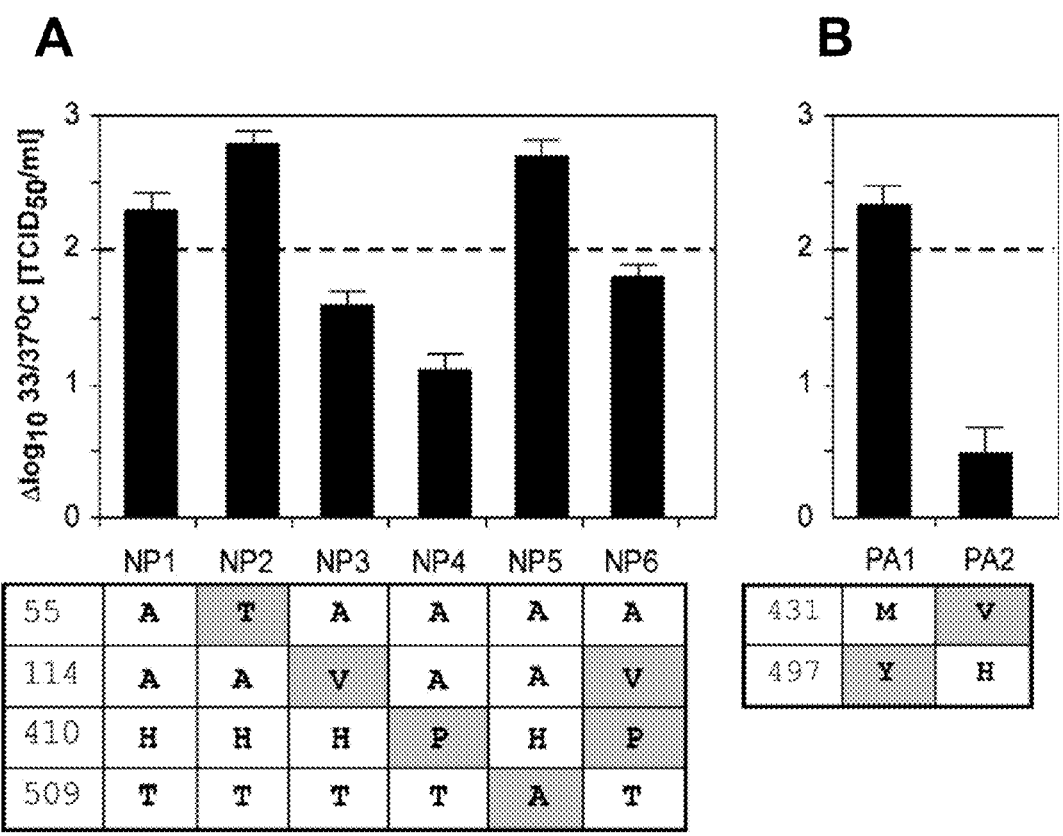
FIG. 11: Bar graphs illustrating differential replication of reassortant viruses. Gray boxes represent wild type amino acid residues. The dotted line represents the shut-off temperature (ts) of 2.0 $\log_{10}$.

To determine whether all of the four amino acids in the NP protein and two in the PA protein contribute to non-ts, triple gene and double-gene recombinants with altered NP and PA genes were generated (FIG. 10). The substitution of two amino acids in the NP protein, A114→V114 and H410→P410 resulted in non-ts phenotype. Viruses with single substitution H410→P410 in the nucleoprotein showed non-ts phenotype in MDCK and PCK. On the other hand, the single substitution A55→T55 showed a ts-phenotype, as did the single substitution at position 509. These results indicate that amino acid residues V114 and P410 in NP are involved in efficient growth at 37° C. (FIG. 11A). A similar strategy was employed to dissect the contribution of the two amino acids in the PA gene. A set of recombinants was constructed, each harboring an NP gene segment with four wild-type consensus amino acids and a PA gene with only one of the two consensus wild type amino acids. Substitution of H497→Y497 remained ts (FIG. 11B), demonstrating that this locus had little impact on expression of the phenotype. In contrast, substitution of M431 with V431 resulted in reversion of the ts phenotype. These results show that amino acids A114 and H410 in NP and M431 in PA are the major determinants for temperature sensitivity of MDV-B.

Based on prior evidence, a ts-phenotype and an attenuated phenotype are highly correlated. It is well established that ca B/Ann Arbor/1/66 virus is not detectable in lung tissue of infected ferrets, whereas non attenuated influenza B viruses are detectable in lungs after intranasal infection. To determine whether identical mutation underlie the ts and att phenotypes, the following studies were performed.

Recombinant viruses obtained after transfection were passaged in embryonated chicken eggs to produce a virus stock. Nine week old ferrets were inoculated intranasally with 0.5 ml per nostril of viruses with titers of 5.5, 6.0 or 7.0 $\log_{in}$ pfu/ml. Three days after infection ferrets were sacrificed and their lungs and turbinates were examined as described previously.

Ferrets (four animals in each group) were infected intranasally with recMDV-B or rec53-MDV-B. Three days after infection virus nasal turbinates and lung tissue were harvested and the existence of virus was tested. No virus was detected in lung tissues of ferrets infected with 7.0 $\log_{10}$ pfu recMDV-B. From the four animals infected with rec53-MDV-B virus with 7.0 $\log_{10}$ pfu in three animals virus was detected in lung tissue (one animal in this group for unknown reasons). In two out of four lung tissues of ferrets infected with rec53-MDV-B at a lower dose (5.5 log pfu/ml) virus could be isolated from lung tissue. Thus, the change of the eight unique amino acids in PA, NP, and M1 protein into wild type residues were sufficient to convert a att phenotype into a non-att phenotype.

Since the data in cell culture showed that PA and NP are main contributors to the ts-phenotype, in a second experiment, ferrets were infected with rec53-MDV-B (PA,NP,M), rec62-MDV-B (PA), NP rec71-MDV-B (NP) with 6 log pfu. Two out of four animals infected with rec53-MDV-B had virus in the lung. None of the lung tissues of ferrets infected with single and double reassortant viruses had detectable levels of virus. Thus, in addition to the amino acids in the PA and NP proteins, the M1 protein is important for the att phenotype. Virus with wt PA and NP did not replicate in ferret lung, indicating that a subset of the mutations involved in attenuation are involved in the ts phenotype.

Thus, the ts and att phenotypes of B/Ann Arbor/1/66 are determined by at most three genes. The conversion of eight amino acids in the PA, NP, and M1 protein into wild type residues resulted in a recombinant virus that replicated efficiently at 37° C.

Similarly, a 6+2 recombinant virus representing the six internal genes of MDV-B with the HA and NA segments from B/HongKong/330/01 showed a ts-phenotype and the triple recombinant was non-ts.

Our results using the MDV-B backbone indicated that six amino acids were sufficient to convert a ts/att phenotype into a non-ts/non-att phenotype. Therefore, we were interested in determining whether the introduction of those six 'attenuation' residues would transfer these biological properties to a heterologous wildtype, non attenuated influenza B virus, such as B/Yamanashi/166/98.

Recombinant wildtype B/Yamanashi/166/98 (recYam) (7) and a recombinant virus (recti-Yam): with six amino acid changes PA (V431→M431, H497→Y497), NP (V114→A114, P410→H410), and M1 (H159→Q159, M183→V183) were produced. RecYam showed a 0.17 log 10 titer reduction in titer at 37° C. compared to 33° C., whereas rec6Yam was clearly ts, the difference in viral titer between 37° C. and 33° C. was 4.6 log 10. Virus was efficiently recovered from ferrets infected with recYam, as expected for a typical wildtype influenza B virus. When rec6Yam was inoculated into ferrets, no virus was detected in the lung tissues (Table 7). Thus, the transfer of the ts/att loci from MDV-B are sufficient to transfer the ts- and att-phenotypes to a divergent virus.

the ca phenotype. Recombinant MDV-B replicated efficiently at 25° C. and 33° C. in the chicken embryonic kidney (CEK) cells. In contrast, recombinant wild type B/Ann Arbor/1/66, containing the nine wild type amino acids, replicated inefficiently at 25° C. It was determined that a total of five wild type amino acids, one in PB2 (R630S), one in PA(M431V) and three in NP(A114V, H410P, T509A), were required for to completely revert the MDV-B ca phenotype. In addition, replacing two amino acids in the M1 protein (Q159H, V183M) of MDV-B or 6:2 vaccine strains with the wild-type amino acids significantly increased virus replication at 33° C. but not at 25° C. in CEK cells; the V183M change had a larger impact on the change.

Example 10

Rescue of Influenza from Eight Plasmids by Electroporation of Vero Cells

Recombinant influenza viruses may also be rescued from Vero cells using electroporation. These methods are suitable

TABLE 7

Attenuation studies in ferrets

| Recombinant virus | wt components[a] | Ts- phenotype | ferrets | Dose [log10 pfu] | Nasal turbinates[b] [log10 pfu/g] | Lung tissue [log10 EID50/g][c] |
|---|---|---|---|---|---|---|
| rMDV-B | none | ts | 4 | 6.0 | 4.01 | <1.5 |
| rec53-B | NP, PA, M | Non-ts | 4 | 6.0 | 4.65 | 3.81 |
| rec62-B | NP, PA | Non-ts | 4 | 6.0 | 4.69 | <1.5 |
| rec71NP-B | NP | ts | 4 | 6.0 | 4.13 | <1.5 |
| rec71M-B | M | ts | 4 | 6.0 | 4.17 | <1.5 |
| RecYam | | Non-ts | 4 | 6.0 | 4.92 | 3.31 |
| rec6Yam | | ts | 4 | 6.0 | 4.02 | <1.5 |

[a]Recombinant viruses with MDV-B backbone that differed in wildtype amino acids were used to infected ferrets intranassally. RecYam is recombinant B/Yamanashi/166/98 and Rec6Yam represents a virus that has six 'MDV-B-attenuation' amino acid changes in NP, PA, and M1 with a B/Yamanashi backbone.
[b]Three days after infection the virus titer of the nasal turbinates and lung tissue was determined, the average titer of four infected ferrets is shown.
[c]<1.5 indicates that no virus was detected.

Accordingly, artificially engineered variants of influenza B strain virus having one or more of these amino acid substitutions exhibit the ts and att phenotypes and are suitable for use, e.g., as master donor strain viruses, in the production of attenuated live influenza virus vaccines.

Example 9

Determination of the Loci Controlling the Cold-Adapted Phenotype of B/Ann Arbor/1/66 Influenza Virus The cold adapted (ca) B/Ann Arbor/1/66 is the master donor virus (MDV-B) for the live attenuated influenza B Flumist® vaccines. The 6:2 influenza B vaccines carrying the six internal genes derived from ca B/Ann Arbor/1/66 and the HA and NA surface glycoproteins from the circulating wild-type strains are characterized by the cold-adapted (c a), temperature-sensitive (ts) and attenuated (au) phenotypes. Sequence analysis revealed that MDV-B contains nine amino acids in the PB2, PA, NP and M1 proteins that are not found in wild-type influenza B strains. We have determined that three amino acids in the PA(M431V) and NP(A114V, H410P) determined the ts phenotype and, in addition to these three is loci, two amino acids in the M1 (Q159H, V183M) conferred the att phenotype.

To understand the molecular basis of the ca phenotype, the plasmid-based reverse genetics system was used to evaluate the contribution of these nine MDV-B specific amino acids to for the production of both influenza A and influenza B strain viruses, and permit the recovery of, e.g., cold adapted, temperature sensitive, attenuated virus from Vero cells grown under serum free conditions facilitating the preparation of live attenuated vaccine suitable for administration in, e.g., intranasal vaccine formulations. In addition to its broad applicability across virus strains, electroporation requires no additional reagents other than growth medium for the cell substrate and thus has less potential for undesired contaminants. In particular, this method is effective for generating recombinant and reassortant virus using Vero cells adapted to growth under serum free condition, such as Vero cell isolates qualified as pathogen free and suitable for vaccine production. This characteristic supports the choice of electroporation as an appropriate method for commercial introduction of DNA into cell substrates.

Electroporation was compared to a variety of methods for introduction of DNA into Vero cells, including transfection using numerous lipid based reagents, calcium phosphate precipitation and cell microinjection. Although some success was obtained using lipid based reagents for the rescue of influenza A, only electroporation was demonstrated to rescue influenza B as well as influenza A from Vero cells.

One day prior to electroporation, 90-100% confluent Vero cells were split, and seeded at a density of $9 \times 10^6$ cells per T225 flask in MEM supplemented with pen/strep, L-glutamine, nonessential amino acids and 10% FBS (MEM, 10% FBS). The following day, the cells were trypsinized and resuspended in 50 ml phosphate buffered saline (PBS) per T225 flask. The cells are then pelleted and resuspended in 0.5 ml OptiMEM I per T225 flask. Optionally, customized OptiMEM medium containing no human or animal-derived components can be employed. Following determination of cell density, e.g., by counting a 1:40 dilution in a hemocytometer, $5 \times 10^6$ cells were added to a 0.4 cm electroporation cuvette in a final volume of 400 μl OptiMEM I. Twenty μg DNA consisting of an equimolar mixture of eight plasmids incorporating either the MDV-A or MDV-B genome in a volume of no more than 25 μl was then added to the cells in the cuvette. The cells were mixed gently by tapping and electroporated at 300 volts, 950 microFarads in a BioRad Gene Pulser II with Capacitance Extender Plus connected (BioRad, Hercules, Calif.). The time constant should be in the range of 28-33 msec.

The contents of the cuvette were mixed gently by tapping and 1-2 min after electroporation, 0.7 ml MEM, 10% FBS was added with a 1 ml pipet. The cells were again mixed gently by pipetting up and down a few times and then split between two wells of a 6 well dish containing 2 ml per well MEM, 10% FBS. The cuvette was then washed with 1 ml MEM, 10% FBS and split between the two wells for a final volume of about 3.5 ml per well.

In alternative experiments, Vero cells adapted to serum free growth conditions, e.g., in OptiPro (SFM) (Invitrogen, Carlsbad, Calif.) were electroporated as described above except that following electroporation in OptiMEM I, the cells were diluted in OptiPro (SFM) in which they were subsequently cultured for rescue of virus.

The electroporated cells were then grown under conditions appropriate for replication and recovery of the introduced virus, i.e., at 33° C. for the cold adapted Master Donor Strains. The following day (e.g., approximately 19 hours after electroporation), the medium was removed, and the cells were washed with 3 ml per well OptiMEM I or OptiPro (SFM). One ml per well OptiMEM I or OptiPro (SFM) containing pen/strep was added to each well, and the supernatants were collected daily by replacing the media. Supernatants were stored at −80° C. in SPG. Peak virus production was typically observed between 2 and 3 days following electroporation.

TABLE 8

Results of 8 Plasmid Rescue of MDV strains on Different Cell Types and by Different Transfection Methods

| Substrate | Method | No of Test | Result (Infectious Virus Recovered) |
|---|---|---|---|
| MDV-B | | | |
| COS-7/MDCK | Lipo | 3 | positive |
| COS-7/MDCK | CaPO4 | 2 | positive |
| MRC-5 | Lipo | 5 | negative |
| MRC-5 | CaPO4 | 3 | negative |
| MRC-5 | Electroporation | 2 | negative |
| WI-38 | Lipo | 2 | negative |
| WI-38 | Electroporation | 4 | negative |
| WI-38 | Microinjection | 1 | negative |
| LF1043 | Lipo | 1 | negative |
| LF1043 | CaPO4 | 2 | negative |
| Vero | Lipo | 7 | negative |
| Vero | CaPO4 | 2 | negative |
| Vero/MDCK | Lipo | 1 | negative |
| Vero (serum) | Electroporation | 5 | positive (5/5) |
| Vero (serum free) | Electroporation | 4 | positive (4/4) |

TABLE 8-continued

Results of 8 Plasmid Rescue of MDV strains on Different Cell Types and by Different Transfection Methods

| Substrate | Method | No of Test | Result (Infectious Virus Recovered) |
|---|---|---|---|
| MDV-A | | | |
| Vero (serum) | Electroporation | 3 | positive (3/3) |
| Vero (serum Free) | Electroporation | 3 | positive (3/3) |

Example 11

Influenza B Virus Growth in Eggs Results in Loss of HA 196/197 Glycosylation Site Most influenza B virus clinical isolates contain a potential HA N-linked glycosylation site. This HA N-linked glycosylation site is present around amino acid residues 196-199 for B/Yamagata strains and amino acid residues 197-199 for B/Victoria strains. Recently circulating B/Victoria strains, such as B/Malaysia/2506/04 and B/Ohio/1/05, and recently circulating B/Yamagata strains, such as B/Florida/7/04, contain this potential HA N-linked glycosylation site.

To determine whether the HA glycosylation site of these strains is retained following egg passage, each strain was grown on eggs and nucleotide sequencing was performed to determine the amino acid sequence of the encoded HA polypeptide. The described virus strains used in this study were obtained from the Centers for Disease Control and Prevention (CDC, Atlanta, Ga.). The virus was used to inoculate embryonated chicken eggs obtained from Charles River SPAFAS (Franklin, Conn., North) that had been fertilized 10-11 days prior to virus inoculation. The inoculated eggs were incubated at 33° C. HA viral RNAs from viruses in the inoculated eggs were amplified by RT-PCR, and then sequenced.

The amino acid sequence of the HA polypeptide of influenza B strains B/Ohio/1/05, B/Malaysia/2506/04, and B/Florida/7/04 all changed at the N-linked glycosylation site following egg passage. The sequence at the glycosylation site of B/Ohio/1/05 changed from NET to SET. The sequence at the glycosylation site of B/Malaysia/2506/04 changed from NET to NEA or SET. The sequence at the glycosylation site of B/Florida/7/04 changed from NKT to NKP, DKT, or IKT. See Table 9, below.

TABLE 9

Influenza B HA 196/197 glycosylation site sequences before and after passage in eggs

| | Amino acid 196-198 (197-199) | | |
|---|---|---|---|
| Virus | Clinical isolate* | Egg isolate | cDNA clones |
| B/Ohio/1/05 | NET | SET | SET |
| B/Malaysia/2506/04 | NET | X$^a$EX | NEA |
| | | | SET |
| B/Florida/7/04 | NKT | XKX | NKP |
| | | | DKT |
| | | | IKT |

*HA sequences of clinical isolated provided by Dr. M. Shaw of the CDC.
$^a$X indicates mixed sequences The amino acid sequence at the HA glycosylation site of various other strains of influenza B viruses was examined See FIG. 12, which provides a portion of the HA amino acid sequence for six B/Victoria and eight B/Yamagata following passage on eggs. The potential N-linked glycosylation site (N—X-T/S) is underlined in the figure. It was noted that none of the fourteen influenza B virus strains examined retained their potential N—X-T/S N-linked glycosylation site following egg passage.

Example 12

Loss of the HA 196/197 Glycosylation Site Reduces Influenza B Virus Antigenicity The effect of the HA 196-197 glycosylation site on antigenicity of the influenza B strains B/Ohio/1/05, B/Malaysia/2506/04, and B/Florida/7/04 was next examined To compare antigenicity of the glycosylated versus nonglycosylated viruses, a pair of viruses corresponding to each of the influenza B strains B/Ohio/1/05, B/Malaysia/2506/04, and B/Florida/7/04 was produced using reverse genetics (see Example 3). The two members of each pair were identical except the first member contained an HA polypeptide with a wild-type amino acid sequence, i.e., an HA amino acid sequence containing the N-linked glycosylation site present in the strain obtained from the CDC, and the second member contained an HA polypeptide lacking the N-linked glycosylation site, i.e., an HA amino acid sequence obtained from the virus following egg passage.

Six of the plasmids used in the reverse genetics technique provided nucleotide sequences corresponding to the internal genome segments of ca B/Ann Arbor/1/66 (MDV-B). A seventh plasmid provided a nucleotide sequence corresponding to the genome segment encoding the wild-type NA polypeptide from each wild-type virus, e.g., each member of the pair of B/Ohio/1/05 viruses was produced using the wild-type NA polynucleotide sequence of the B/Ohio/1/05 strain. An eighth plasmid provided a nucleotide sequence corresponding to a genome segment encoding an HA polypeptide. The HA polypeptide was either the wild-type or egg-passaged HA, depending on whether the influenza virus was the first or second member of the pair of viruses.

The NA and HA polynucleotide sequences of the wild-type viruses were obtained by RT-PCR amplification of the NA or HA vRNA of the wild-type viruses, and cloning of the amplified cDNAs between the two BsmBI sites of pAD3000. Plasmids containing nucleotide sequences corresponding to the genome segments encoding the egg passaged HA polypeptides were prepared by subjecting the plasmids containing the wild-type HA segments to site-directed mutagenesis using a QuikChange® site-directed mutagenesis kit (Stratagene, La Jolla, Calif.).

The plasmids were transfected into co-cultured MDCK and 293 cells. All rescued viruses replicated efficiently in MDCK cells with titers of 6-7 $\log_{10}$ PFU/mL. Seven days after transfection, supernatants from the transfected cells were collected and titrated by plaque assay. Sequence analysis of the recovered viruses confirmed that the wild-type or egg-passaged HA amino acid sequence was retained, in accordance with the HA plasmid used to produce the virus during the transfection.

Antigenicity of each pair of viruses was examined by HAI assay using post-infection ferret sera. Sera were collected from ferrets 21 days following intranasal inoculated with 6-7 $\log_{10}$ PFU virus. Antibody levels in ferret serum against the various viruses were assessed by the hemagglutination-inhibition (HAI) assay. The HAI assay was performed by adding 25 μL serial diluted serum samples with 4 HA units of influenza virus (in a 25 μL volume) in V-bottom 96-well microplates. Following 30 min incubation, 50 μl of 0.5% turkey erythrocytes was added to measure hemagglutination. HAI titer was expressed as the highest serum dilution which inhibits virus hemagglutination. Table 10 provides the antigenicity of the paired wt (HA glycosylation$^+$)/egg-passaged (HA glycosylation$^-$) viruses.

TABLE 10

Antigenicity of HA 196/197 glycosylation site variants in ferrets

| Virus | Amino Acid 196-198 (197-199) | Geometric mean HAI titer of post infection ferret serum against | |
|---|---|---|---|
| | | Glycosylated (G−) | Non-glycosylated (G+) |
| B/Ohio/1/05 | SET (G−) | 101.6 | 16.0 |
| | NET (G+) | 64.0 | 64.0 |
| B/Malaysia/2506/04 | NEA (G−) | 64.0 | 32.0 |
| | NET (G+) | 25.4 | 50.8 |
| B/Florida/7/04 | DKT (G−) | 161.3 | 28.5 |
| | NKT (G+) | 35.9 | 80.6 |

Sera generated against HA glycosylated viruses had higher HAI titers against HA glycosylated viruses than paired HA nonglycosylated viruses, and sera generated against HA nonglycosylated viruses had higher HAI titers against paired HA nonglycosylated viruses. The antigenic differences between each paired HA glycosylated/HA non-glycosylated virus in the HAI assay varied from 1.5-4.5-fold. This variance indicated that the 196/197 glycosylation site affected virus antigenicity.

Example 13

Influenza B Viruses Having the HA 196/197 GLYCOSYLATION SITE WERE UNABLE TO REPLICATE IN EGGS To determine whether each member of the paired influenza strains of Example 12 could replicate in eggs, embryonated eggs were inoculated with $10^2$ PFU/egg or $10^4$-$10^5$ PFU/egg virus and incubated at 33° C. for three days. Virus peak titers were then determined by plaque assay in MDCK cells. Replication of the paired viruses on eggs (virus titer) and sequence at HA amino acid residues 196-199 for each of the viruses is shown in Table 11.

TABLE 11

Replication of paired HA 196/197 glycosylation variants in eggs

| Virus | Amino Acid 196-198 (197-199) | Virus titer ($\log_{10}$ PFU/ml) | Amino Acid 196-199 (197-200) after growth in eggs |
|---|---|---|---|
| B/Ohio/1/05 | SET (G−) | 8.7$^a$ | SETQ (SEQ ID NO: 52) |
| | NET (G+) | 2.1$^a$ | ND$^d$ |
| | | 8.8$^b$ | SETQ (SEQ ID NO: 52) |
| B/Malaysia/2506/04 | NEA (G−) | 8.7$^a$ | NEAQ (SEQ ID NO: 53) |
| | NET (G+) | 1.7$^a$ | ND |
| | | 7.3$^b$ | SETQ (SEQ ID NO: 52) |
| | | | NENQ (SEQ ID NO: 54) |

TABLE 11-continued

Replication of paired HA 196/197 glycosylation variants in eggs

| Virus | Amino Acid 196-198 (197-199) | Virus titer (log$_{10}$ PFU/ml) | Amino Acid 196-199 (197-200) after growth in eggs |
|---|---|---|---|
| B/Florida/ 7/04 | DKT (G−) | 8.2$^a$ | DKTQ (SEQ ID NO: 49) |
|  | NKT (G+) | 3.0$^a$ | NKTQ (SEQ ID NO: 48) |
|  |  | 6.7$^b$ | NKIQ (SEQ ID NO: 55) |
|  |  |  | NKTP (SEQ ID NO: 50) |

$^{a,b}$Eggs were inoculated with 10$^2$ PFU/egg ($^a$) or 10$^4$-10$^5$ PFU/egg ($^b$) of the indicated 6:2 reassortant viruses.
$^c$The HA sequence of the virus recovered from eggs were determined and amino acid sequence changes are indicated as underlined.
$^d$ND: Not determined.

For each virus pair, the member virus lacking the glycosylation site grew well in eggs, to titers greater than 8.0 log$_{10}$ PFU/mL. However, the member virus containing the glycosylation site (NXT) did not replicate well in eggs inoculated with 10$^2$ PFU virus. See Table 11, which indicates that HA glycosylated viruses B/Ohio/1/05, B/Malaysia/2506/04, and B/Florida/7/04, grew to virus titers of only 2.1 log$_{10}$ PFU/mL, 1.7 log$_{10}$ PFU/mL, and 3.0 log$_{10}$ PFU/mL, respectively. Replication of the HA glycosylated member viruses became detectable when the eggs were inoculated with higher amounts of virus, 10$^4$-10$^5$ PFU/egg. Sequence analysis of these replicating viruses revealed that an amino acid substitution had been introduced at the 196/197 glycosylation site. See Table 11, which indicates that wt glycosylation sequence of B/Ohio/1/05 changed from NET to SET, the wt glycosylation sequence of B/Malaysia/2506/04 changed from NET to SET or NEN, and that the wt glycosylation sequence of B/Florida/7/04 changed from NKT to NKI or a proline was substituted for glutamine immediately C-terminal to the NXT glycosylation sequence. Prior studies (Bause, *Biochem J.* 209 (1983):331-336; Gavel and Von Heijne, *Protein Eng.* 3 (1990):433-442) have shown that proline C-terminally adjacent to the HA NXT glycosylation site prevents N-linked glycosylation. Thus, it appeared that lack of glycosylation at HA 196/197 was needed for the influenza B viruses to replicate well on eggs.

Example 14

Identification of an HA Glycosylation$^+$ Influenza B Strain Able to Replicate on Eggs To determine whether any influenza B strains containing the 196/197 glycosylation site were able to replicate in eggs, eggs were inoculated with various wildtype influenza B virus strains. The HA sequence of the replicating viruses was then determined Most of the influenza B viruses that were able to replicate on eggs did not contain the NXT glycosylation site at residues 197-199 (or 196-198). If the egg-passaged viruses did contain the NXT glycosylation site they were in the process of losing it; the NXT sequence was one of a population of sequences at residues 197-199/196-198 of the HA protein.

Two virus strains, B/Jilin/20/03 (B/JL) and B/Jiangsu/10/03 (B/JS), were identified as having the NXT glycosylation sequence, NKT, following egg passage. B/JL had a proline at position 199, immediately C-terminal to the 196-198 glycosylation site. As discussed above, proline immediately C-terminal to the glycosylation site residues likely interferes with and prevents 196/197 glycosylation. To more closely examine replication of B/JL and B/JS on eggs, paired influenza B virus strains, lacking and containing the NXT glycosylation site sequence were prepared for each of B/JL, B/JS, and related influenza B strain B/Shanghai/361/02 (B/SH) by reverse genetics as described in Example 12. Replication of these paired viruses on MDCK cells and eggs was then determined See Table 12.

TABLE 12

B/Jiangsu/10/03 maintained the 196-197 glycosylation site in eggs

| Virus$^a$ | Amino Acid 196-199 | Virus Titer (log$_{10}$PFU/ml) | | Amino Acid 196-199 after growth in eggs$^c$ |
|---|---|---|---|---|
|  |  | NDCK | Egg |  |
| B/JS/10/03 | DKTQ (G−) (SEQ ID NO: 49) | 6.5 | 7.3$^a$ | DKTQ (SEQ ID NO: 49) |
|  | NKTQ (G+) (SEQ ID NO: 48) | 7.4 | 8.4$^a$ | NKTQ (SEQ ID NO: 48) |
| B/SH/361/02 | DKTQ (G−) (SEQ ID NO: 49) | 7.3 | 8.7$^a$ | DKTQ (SEQ ID NO: 49) |
|  | NKTQ (G+) (SEQ ID NO: 48) | 6.9 | 3.9$^a$ | NKTQ (SEQ ID NO: 48) |
|  |  |  | 6.2$^b$ | SKTQ (SEQ ID NO: 56) |
|  |  |  |  | DKTQ (SEQ ID NO: 49) |

TABLE 12-continued

B/Jiangsu/10/03 maintained the 196-197 glycosylation site in eggs

| Virus[a] | Amino Acid 196-199 | Virus Titer (log$_{10}$PFU/ml) | | Amino Acid 196-199 after growth in eggs[c] |
|---|---|---|---|---|
| | | NDCK | Egg | |
| B/JL/20/03 | NKTP (G−) (SEQ ID NO: 50) | 6.4 | 7.6[a] | NKTP (SEQ ID NO: 50) |
| | NKTQ (G+) (SEQ ID NO: 48) | 7.5 | 3.0[a] | NKTQ (SEQ ID NO: 48) |
| | | | 6.8[b] | NK<u>S</u>Q (SEQ ID NO: 57) |

[a,b] MDCK cells were infected with the indicated virus at moi of 0.004 and eggs were inoculated with 10² PFU/egg ([a]) or 10⁴-10⁵ PFU/egg ([b]) of the indicated 6:2 reassortant viruses amplified in MDCK cells that either had (G+) or did not have (G−) the 196/197 HA glycosylation site and incubated at 33° C. for three days. Virus peak titers were determined by plaque assay in MDCK cells.
[c] The HA sequence of the virus recovered from eggs were determined and amino acid sequence changes are indicated as underlined.

All three paired virus sets replicated well in MDCK cells, with titers ranging from 6.4 to 7.5 log$_{10}$ PFU/mL. However, not all viruses replicated well in eggs. Eggs inoculated with 10² log$_{10}$ PFU of either of the HA 196/197 glycosylated (glycosylation sequence NKTQ (SEQ ID NO: 48)) B/SH or B/JL viruses did not replicate well. Raising the inoculating dose of the B/SH or B/JL HA glycosylated viruses to 10⁴-10⁵ log$_{10}$ PFU resulted in detectable virus replication. Sequencing these replicating viruses revealed loss of the glycosylation site (from NKT to SKT or DKT in B/SH and from NKT to NKS in B/JL). Unlike the B/SH and B/JL viruses, the B/JS virus was able to replicate well in eggs in the presence or absence of the glycosylation site, titers of 7.3 and 8.4 log$_{10}$ PFU, respectively.

Western blotting with an HA specific antibody confirmed the glycosylation status of each of the viruses grown in MDCK cells and in eggs. Western blotting was performed by mixing virus from MDCK cell culture supernatants or allantoic fluid with 2× protein lysis buffer (Invitrogen) and electrophoresing on a 10% SDS-PAGE gel. The electrophoresed proteins on the gel were transferred to a nitrocellulose membrane and subjected to Western blot using chicken anti-influenza B antiserum. The protein-antibody complex was detected by a chemiluminescent detection kit (GE Healthcare Bio-Sciences) following incubation with HRP conjugated anti-chicken antibodies.

Western blot analysis showed that when replicated on MDCK cells, HA glycosylation viruses retained their glycosylation site and therefore migrated more slowly on the gel than did their paired counterpart HA glycosylation⁻ viruses. See, for example, lanes 1 and 2 of FIG. 13a, which show a band the cross-reacts with the HA antiserum of the glycosylation⁺ HA (lane 1) virus migrating more slowly than the band in the lane with the virus having the glycosylation⁺ HA (lane 2). Similar results were obtained for both the B/SH (FIG. 13a, lanes 3 and 4) and B/JL (FIG. 13a, lines 5 and 6) viruses.

Figure 13:
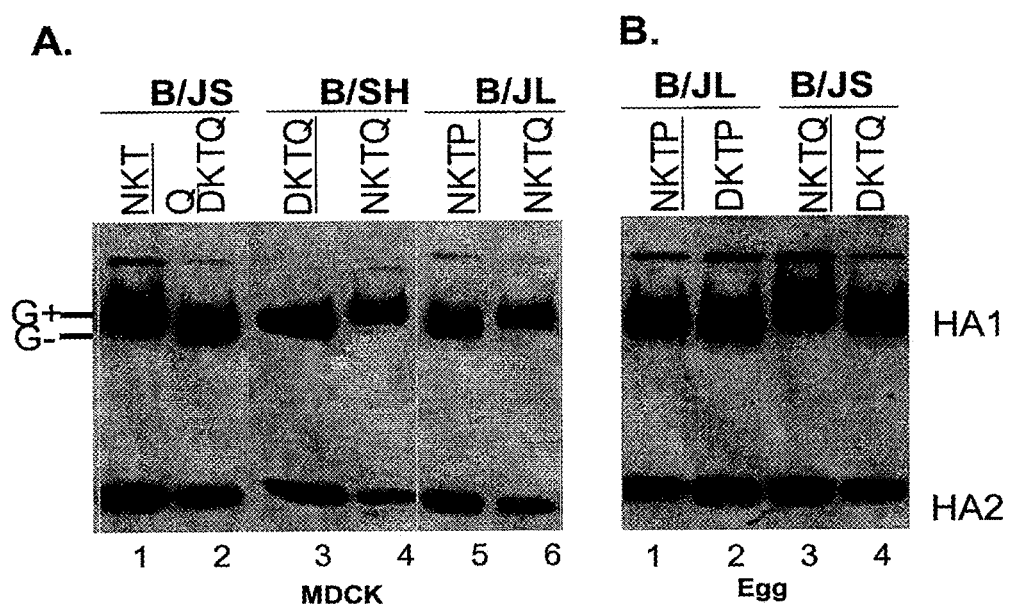
FIG. 13: Confirmation of HA glycosylation by Western Blot. 6:2 B/Shanghai/361/02 (B/SH), 6:2 B/Jilin/20/03 (B/JL) and 6:2 B/Jiangsu/10/03 (B/JS) with the indicated 196-199 sequence (SEQ ID NOS: 48, 49, 49, 48, 50, 48, 50, 51, 48 and 49, respectively, in order of appearance) were electrophoresed on 10% SDS-PAGE. The HA1 and HA2 proteins were detected by Western Blotting using polyclonal anti HA antibody. Underlining indicates the original sequence present in the virus egg isolate.

When replicated on eggs, only one virus, the B/JS virus, retained the migration pattern in which the band for the glycosylation⁺ HA virus (FIG. 13b, lane 3) migrated more slowly than the band for the glycosylation⁻ HA virus (FIG. 13b, lane 4). This pattern suggested that the B/JS virus was the only virus tested which could replicate on eggs and retain the HA glycosylation site.

Example 15

Arginine at HA Amino Acid Residue Position 141 Stabilizes the 196-197 Glycosylation Site Review of Table 12 revealed that although both B/JS and B/JL influenza strains had the amino acid sequence NKTQ (SEQ ID NO: 48) at HA amino acid residues 196-199, only B/JS was able to replicate well on eggs and retain the NKTQ (SEQ ID NO: 48) glycosylation site. Comparison of the HA amino acid sequence of the B/JS and B/JL viruses identified three differing amino acid residues. Among these three residues, 141R and 237E were unique to B/JS (relative to other influenza B viruses). At amino acid residue positions 141 and 237, most influenza B strains contain glycine. To test whether one or both of the 141R and/or 237E amino acid residues contributed to stabilization of the B/JS HA 196 glycosylation site, B/JS HA was mutagenized to change 141R and/or 237E to glycine. Replication of the various B/JS viruses on eggs was then determined.

As shown in Table 13, when B/JS HA residue 141 was changed from R to G, the virus was unable to replicate on eggs inoculated at a dose of 10² PFU. Increasing the inoculating dose to 10⁴-10⁵ PFU permitted the virus to replicate on eggs. The replicating B/JS virus having the HA 141G residue was sequenced to determine whether the 196/197 glycosylation site was retained. Sequencing revealed that the NKT glycosylation site had been lost and replaced with either DKT or NKTP (SEQ ID NO: 50). This finding indicated that the HA 141 arginine residue of B/JS may be stabilizing the 196/197 HA glycosylation site. Substituting a glycine for glutamate at B/JS HA amino acid residue 237 did not affect growth on eggs. Data not shown.

TABLE 13

HA 141R stabilizes the 196/197 glycosylation site during egg passage

| Virus | Amino acid at the indicated position 141 | Virus Titers ($\log_{10}$ PFU/ml) | | Amino acid 196-199 (197-200) after growth in eggs[c] |
|---|---|---|---|---|
| | 196-198 (197-199) | NDCK | Egg | |
| B/JS/ 10/03 | R | 7.4 | 8.4[a] | NKTQ (SEQ ID NO: 48) |
| | G | 7.0 | 2.4[a] | NKTQ (SEQ ID NO: 48) |
| | | | 8.5[b] | DKTQ (SEQ ID NO: 49) |
| | | | | NKTP (SEQ ID NO: 50) |
| B/SH/ 361/02 | R | 7.6 | 8.0[a] | NKTQ (SEQ ID NO: 48) |
| B/Ohio/ 1/05 | R | 7.6 | 7.9[a] | NETQ (SEQ ID NO: 58) |

[a,b] MDCK cells were infected with the indicated virus at moi of 0.004 and eggs were inoculated with $10^2$ PFU/egg ([a]) or $10^4$-$10^5$ PFU/egg ([b]) of the indicated 6:2 reassortant viruses amplified in MDCK cells that either had (G+) or did not have (G-) the 196/197 HA glycosylation site and incubated at 33° C. for three days. Virus peak titers were determined by plaque assay in MDCK cells.
[c] The HA sequence of the virus recovered from eggs were determined and amino acid sequence changes are indicated as underlined.

Figure 14:
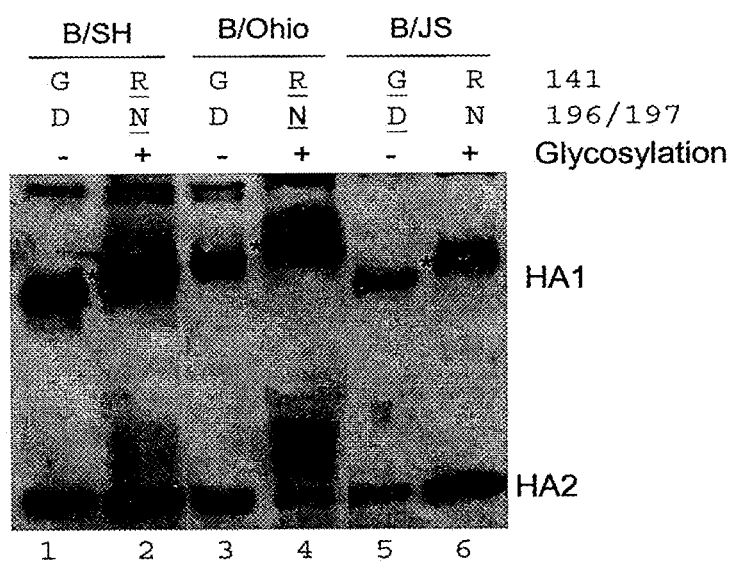
FIG. 14: Egg-grown viruses with arginine at HA residue 141 retain glycosylation at residue 196-197. 6:2 B/Shanghai/361/02 (B/SH), 6:2 B/Ohio/1/05 (B/Ohio) and 6:2 B/Jiangsu/10/03 (B/JS) with indicated residues at 141 and 196/197 were grown in eggs and viruses were electrophoresed on 10% SDS-PAGE. The HA1 and HA2 proteins were detected by Western Blotting using polyclonal anti HA antibody. The slower migrating HA1 indicates the 196/197 site was glycosylated as indicated by *. Underlining indicates the original sequence present in the virus egg isolate.

To further confirm that HA residue 141R was sufficient to stabilize the influenza B HA 196/197 glycosylation site during egg replication, an amino acid substitution of arginine for glycine at HA 141 of B/SH and B/Ohio/1/05 was introduced. As shown in Table 13, both B/SH and B/Ohio/1/05 viruses having the glycine to arginine substitution at HA position 141 were able to replicate efficiently in eggs, titers of approximately 8.0 $\log_{10}$ PFU/mL. The B/SH and B/Ohio/1/05 viruses with the HA 141R substitution also retained HA glycosylation during egg replication. See FIG. 14, which provides a Western blot confirming HA glycosylation of egg passaged B/SH (lane 2), B/Ohio (lane 4), and B/JS (lane 6) viruses having the HA 141R residue. These data indicated that HA residue 141 plays a role in influencing the use of the HA 196/197 glycosylation site of influenza B viruses grown on eggs.

Example 16

Arginine at HA Residue 141OF Influenza B does not Effect Virus Antigenicity

The effect of substituting an arginine residue at HA amino acid position 141 on antigenicity of the influenza B strains was tested. To determine whether the 141R residue affects virus antigenicity, ferret sera was generated against different glycosylated and nonglycosylated viruses. The ferret sera was tested for reactivity against viruses that contained different modifications in the 141 and 196/197 residues.

Ferret sera was prepared by intranasally inoculating ferrets with 7.0 $\log_{10}$ PFU egg-derived viruses with genetic signatures of GD (nonglycosylated) or RN (glycosylated) at the 141 and 196/197 sites, respectively. Post-infection serum was collected from the ferrets twenty-one days later for antigenicity testing in the HAI assay.

B/SH/361/02, B/Ohio/1/05, and B/JS/10/03 viruses having each of the genetic signatures of GD, RN or GN at HA amino acid positions 141 and 196/197, respectively, were prepared to test for antigenicity against the ferret sera. These viruses were prepared from infected MDCK cells; influenza viruses with the G141 and 196/197N residues were unable to grow in eggs.

In the HAI assay, ferret serum generated against nonglycosylated (GD) B/SH/361/02 reacted well with the nonglycosylated B/SH/361/02 virus, but not the glycosylated B/SH/361/02 virus; the HAI titer of the post infection ferret serum was four-fold greater for the nonglycosylated relative to the glycosylated virus. Similarly, ferret serum generated against glycosylated (RN) B/SH/361/02 virus reacted well with glycosylated B/SH/361/02 virus, but not nonglycosylated B/SH/361/02 virus. Again, the difference in HAI titer of the post infection ferret serum was four-fold. These four-fold differences are indicative of an antigenic difference between non-glycosylated and glycosylated viruses, also discussed in Example 12, Table 10.

Ferret serum generated against glycosylated (RN) B/SH/361/02, reacted similarly against the RN and GN glycosylated viruses in the HAI assay; 2-fold greater against the RN glycosylated virus relative to the GN glycosylated virus. This slight difference in reactivity indicated that the amino acid residue change at position 141 from glycine to arginine did not have a significant impact on B/SH/361/02 antigenicity. Similar results were obtained when the same set of HAI assays were performed using influenza B virus strains B/Ohio/1/05 and B/JS/10/03. See Table 14.

TABLE 14

Lack of Effect of Amino Acid 141 on Antigenicity of Influenza B Strains

| | Amino acid at | | Geometric mean HAI titer of post infection ferret serum | |
|---|---|---|---|---|
| Virus | 141 | 196/197 | GD | RN |
| B/SH/361/02 | G | D (G−) | 203.2 | 40.3 |
| | R | N (G+) | 40.3 | 161.3 |
| | G | N (G+) | 40.3 | 80.6 |
| B/Ohio/1/05 | G | S (G−) | 101.6 | 32.0 |
| | R | N (G+) | 32.0 | 161.3 |
| | G | N (G+) | 25.4 | 80.6 |
| B/JS/10/03 | G | D (G−) | 256.0 | 16.0 |
| | R | N (G+) | 32.0 | 90.5 |
| | G | N (G+) | 128.0 | 128.0 |

The ferret serum was tested for HAI titers against MDCK-derived viruses using chicken red blood cells.
Geometric mean HAI titers were calculated from three ferret post infection sera.
Homologous HAI titers underlined.

Example 17

Glycosylation at HA 196/197 Affects Binding to α-2,3 Linked Sialic Acids

Because influenza B viruses in which the HA 196/197 site is glycosylated grow well in MDCK cells but not in eggs, glycosylation at HA 196/197 may affect virus receptor binding specificity. Sia (α-2,3) Gal and Sia (α-2,6) Gal are the two major receptor moieties differentially distributed in different host cells. MDCK cells express both Sia (α-2,3) Gal and Sia (α-2,6) Gal moieties. Chicken embryo chorio-allantoic membrane cells express only Sia (α-2,3) Gal moieties. Virus receptor binding specificity can be examined by the hemaagglutination assay using erythrocytes (RBC) from different animal species that differentially express Sia (α-2,3) and Sia (α-2,6) Gal moieties. Horse RBC mainly express Sia (α-2,3) Gal receptors while guinea pig RBC mainly express Sia (α-2, 6) Gal receptors. Turkey and chicken RBC are enriched in expression of both Sia (α-2,3) and Sia (α-2,6) Gal moieties (Ito et al., *Virol.* 156 (1997):493-499).

Egg derived B/Ohio/1/05 and B/Jiangsu/10/03 viruses that were glycosylation+ (RN) or glycosylation− (GS, RS, GD, or RD) were tested for their HA titers using horse RBCs (hRBCs), guinea pig RBCs (gpRBCs) and turkey RBCs (tRBCs). Regardless of glycosylation status of influenza B viruses, they all bound similarly well to gpRBCs and tRBCs, both of which express Sia (α-2,6) Gal moieties. In contrast, glycosylation+ (RN) viruses bound poorly or at undetectable levels to hRBC, which only express Sia (α-2,3) moieties, suggesting that glycosylation at HA 196/197 inhibited virus binding to Sia (α-2,3) Gal receptors. See Table 15.

TABLE 15

HA 196/197 glycosylation inhibits HA binding to receptors having α-2,3 linked sialic acid

| Virus | Amino acid at 141 | Amino acid at 196/197 | Virus Titer ($\log_{10}$ PFU/ml) | Hemagglutination (HA) titer with the indicated red blood cells | | |
|---|---|---|---|---|---|---|
| | | | | hRBC | gpRBC | tRBC |
| B/Ohio/1/05 | G | S (G−) | 8.9 | 128 | 128 | 128 |
| | R | S (G−) | 9.3 | 512 | 64 | 128 |
| | R | N (G+) | 8.1 | <2 | 64 | 64 |
| B/JS/10/03 | G | D (G−) | 8.9 | 1024 | 128 | 256 |
| | R | D (G−) | 7.6 | 64 | 32 | 32 |
| | R | N (G+) | 8.6 | 4 | 128 | 256 |

The inability of the glycosylated viruses to bind to cells expressing Sia (α-2,3) moieties, such as allantoic cells of embryonated chicken eggs, makes it difficult to grow influenza B vaccine strains in eggs. Loss of the glycosylation site, which permits growth of influenza B strains in eggs, alters the antigenicity of the strains. The ability to retain the HA 196/197 glycosylation site of influenza B viruses, while maintaining growth on eggs and virus antigenicity would aid vaccine manufacture. The introduction of an arginine at HA amino acid position 141 of influenza B strains is a means of accomplishing this.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

In particular, the following patent application is incorporated by reference in its entirety: U.S. Provisional Application Nos. 60/944,600, filed Jun. 18, 2007.

We claim:

1. A method of preparing influenza B virus comprising:
   (a) introducing a mutation in a hemagglutinin (HA) genome segment resulting in an amino acid substitution at position 141 to arginine, thereby generating a modified HA polypeptide; and
   (b) replicating an influenza B virus comprising the modified HA polypeptide under conditions whereby influenza B virus is produced, wherein the influenza B virus comprising the modified HA polypeptide replicates to a higher titer than an influenza B virus comprising an HA polypeptide that is unmodified at position 141.

2. The method of claim 1, wherein the introducing a mutation in (a) is performed by site-directed mutagenesis.

3. The method of claim 1, further comprising:
   (c) determining viral antigenicity for the influenza B virus produced in (b).

4. The method of claim 3, wherein the viral antigenicity of the influenza B virus produced in (b) is not significantly altered by the amino acid substitution in (a).

5. The method of claim 3, wherein the viral antigenicity of the influenza B virus produced in (b) and the viral antigenicity of an influenza B virus comprising an HA polypeptide that is unmodified at position 141 differ by less than 20%.

6. The method of claim 3, wherein the viral antigenicity of the influenza B virus produced in (b) and the viral antigenicity of an influenza B virus comprising an HA polypeptide that is unmodified at position 141 differ by less than 10%.

7. The method of claim 3, wherein the viral antigenicity of the influenza B virus produced in (b) and the viral antigenicity of an influenza B virus comprising an HA polypeptide that is unmodified at position 141 differ by less than 5%.

8. The method of claim 1, wherein the influenza B virus produced in (b) is a reassortant influenza B virus.

9. The method of claim 8, wherein the reassortant influenza B virus comprises at least six internal genome segments from a donor influenza B virus.

10. The method of claim 9, wherein the donor influenza B virus has one or more phenotypes chosen from temperature-sensitive, cold-adapted, and attenuated.

11. The method of claim 10, wherein the donor influenza B virus is B/Ann Arbor/1/66.

* * * * *

SEQUENCE LISTING

```
<160> NUMBER OF SEQ ID NOS: 58

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aacaattgag atctcggtca cctcagacat gataagatac attgatgagt            50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tataactgca gactagtgat atccttgttt attgcagctt ataatggtta            50

<210> SEQ ID NO 3
<211> LENGTH: 2836
<212> TYPE: DNA
<213> ORGANISM: Artificial Sequence
<220> FEATURE:
<223> OTHER INFORMATION: Description of Artificial Sequence: Synthetic
      cloning vector polynucleotide

<400> SEQUENCE: 3
ctagcagtta accggagtac tggtcgacct ccgaagttgg gggggaggag acggtaccgt     60
ctccaataac ccggcggccc aaaatgccga ctcggagcga aagatatacc tcccccgggg    120
ccgggaggtc gcgtcaccga ccacgccgcc ggcccaggcg acgcgcgaca cggacacctg    180
```

```
tccccaaaaa cgccaccatc gcagccacac acggagcgcc cggggccctc tggtcaaccc    240
caggacacac gcgggagcag cgccgggccg gggacgccct cccggcggtc acctcagaca    300
tgataagata cattgatgag tttggacaaa ccacaactag aatgcagtga aaaaaatgct    360
ttatttgtga aatttgtgat gctattgctt tatttgtaac cattataagc tgcaataaac    420
aaggatctgc attaatgaat cggccaacgc gcggggagag gcggtttgcg tattgggcgc    480
tcttccgctt cctcgctcac tgactcgctg cgctcggtcg ttcggctgcg gcgagcggta    540
tcagctcact caaaggcggt aatacggtta tccacagaat caggggataa cgcaggaaag    600
aacatgtgag caaaaggcca gcaaaaggcc aggaaccgta aaaaggccgc gttgctggcg    660
ttttTccata ggctccgccc ccctgacgag catcacaaaa atcgacgctc aagtcagagg    720
tggcgaaacc cgacaggact ataaagatac caggcgtttc ccctggaag ctccctcgtg    780 cgctctcctg ttccgaccct gccgcttacc ggatacctgt ccgcctttct cccttcggga    840
agcgtggcgc tttctcaatg ctcacgctgt aggtatctca gttcggtgta ggtcgttcgc    900
tccaagctgg gctgtgtgca cgaaccccCC gttcagcccg accgctgcgc cttatccggt    960
aactatcgtc ttgagtccaa cccggtaaga cacgacttat cgccactggc agcagccact   1020
ggtaacagga ttagcagagc gaggtatgta ggcggtgcta cagagttctt gaagtggtgg   1080
cctaactacg gctacactag aaggacagta tttggtatct gcgctctgct gaagccagtt   1140
accttcggaa aaagagttgg tagctcttga tccggcaaac aaaccaccgc tggtagcggt   1200
ggttttTttg tttgcaagca gcagattacg cgcagaaaaa aaggatctca agaagatcct   1260
ttgatctttt ctacggggtc tgacgctcag tggaacgaaa actcacgtta agggattttg   1320
gtcatgagat tatcaaaaag gatcttcacc tagatccttt taaattaaaa atgaagtttt   1380
aaatcaatct aaagtatata tgagtaaact tggtctgaca gttaccaatg cttaatcagt   1440
gaggcaccta tctcagcgat ctgtctattt cgttcatcca tagttgcctg actccccgtc   1500
gtgtagataa ctacgatacg ggagggctta ccatctggcc ccagtgctgc aatgataccg   1560
cgagacccac gctcaccggc tccagattta tcagcaataa accagccagc cggaagggcc   1620
gagcgcagaa gtggtcctgc aactttatcc gcctccatcc agtctattaa ttgttgccgg   1680
gaagctagag taagtagttc gccagttaat agtttgcgca acgttgttgc cattgctaca   1740
ggcatcgtgg tgtcacgctc gtcgtttggt atggcttcat tcagctccgg ttcccaacga   1800
tcaaggcgag ttacatgatc ccccatgttg tgcaaaaaag cggttagctc cttcggtcct   1860
ccgatcgttg tcagaagtaa gttggccgca gtgttatcac tcatggttat ggcagcactg   1920
cataattctc ttactgtcat gccatccgta agatgctttt ctgtgactgg tgagtactca   1980
accaagtcat tctgagaata gtgtatgcgg cgaccgagtt gctcttgccc ggcgtcaata   2040
cgggataata ccgcgccaca tagcagaact ttaaaagtgc tcatcattgg aaaacgttct   2100
tcggggcgaa aactctcaag gatcttaccg ctgttgagat ccagttcgat gtaacccact   2160
cgtgcaccca actgatcttc agcatctttt actttcacca cgtttctggg tgagcaaaa    2220 acaggaaggc aaaatgccgc aaaaaaggga ataagggcga cacggaaatg ttgaatactc   2280
atactcttcc tttttcaata ttattgaagc atttatcagg gttattgtct catgagcgga   2340
tacatatttg aatgtatttta gaaaaataaa caaataggggttccgcgcac atttccccga   2400 aaagtgccac ctgacgtcga tatgccaagt acgcccccta ttgacgtcaa tgacggtaaa   2460
tggcccgcct ggcattatgc ccagtacatg accttatggg actttcctac ttggcagtac   2520
atctacgtat tagtcatcgc tattaccatg gtgatgcggt tttggcagta catcaatggg   2580
```

```
cgtggatagc ggtttgactc acggggattt ccaagtctcc accccattga cgtcaatggg    2640
agtttgtttt ggcaccaaaa tcaacgggac tttccaaaat gtcgtaacaa ctccgcccca    2700
ttgacgcaaa tgggcggtag gcgtgtacgg tgggaggtct atataagcag agctctctgg    2760
ctaactagag aacccactgc ttactggctt atcgaaatta atacgactca ctatagggag    2820
acccaagctg ttaacg                                                   2836

<210> SEQ ID NO 4
<211> LENGTH: 2369
<212> TYPE: DNA
<213> ORGANISM: Influenza B virus

<400> SEQUENCE: 4
agcagaagcg gagcctttaa gatgaatata atccttatt ttctcttcat agatgtaccc      60
atacaggcag caatttcaac aacattccca tacaccggtg ttcccccctta ttcccatgga    120 acggaacag gctacacaat agacaccgtg attagaacac atgagtactc aaacaaggga    180
aaacaataca tttctgatgt tacaggatgt gcaatggtag atccaacaaa tgggccatta    240
cccgaagata tgagccgag tgcctatgca caattggatt gcgttctgga ggctttggat    300
agaatggatg aagaacatcc aggtctgttt caagcagcct cacagaatgc catggaggca    360
ctaatggtca caactgtaga caaattaacc caggggagac agactttga ttggacagtg    420 tgcagaaacc aacctgctgc aacggcactg aacacaacaa taacctcttt taggttgaat    480
gatttgaatg gagccgacaa gggtggatta gtacccttt gccaagatat cattgattca    540
ttggacaaac ctgaaatgac tttcttctcg gtaaagaata taagaaaaaa attgcctgct    600
aaaaacagaa agggtttcct cataaagaga ataccaatga aggtaaaaga cagaataacc    660
agagtggaat acatcaaaag agcattatca ttaaacacaa tgacaaaaga tgctgaaaga    720
ggcaaactaa aaagaagagc aattgccacc gctgggatac aaatcagagg gtttgtatta    780
gtagttgaaa acttggctaa aaatatctgt gaaaatctag aacaagtgg tttgccagta    840 ggtgggaacg agaagaaggc caaactgtca aatgcagtgg ccaaaatgct cagtaactgc    900
ccaccaggag ggatcagcat gacagtgaca ggagacaata ctaaatggaa tgaatgctta    960
aatccaagaa tctttttggc tatgactgaa agaataacca gagacagccc aatttggttc   1020
cgggattttt gtagtatagc accggtcttg ttctccaata aaatagccag attgggaaaa   1080
gggttcatga taacaagcaa aacaaaaaga ctgaaggctc aaataccttg tcccgatctg   1140
tttaatatac cattagaaag atataatgaa gaaacaaggg caaaattaaa aaagctgaaa   1200
ccattcttca atgaagaagg aacggcatct ttgtcgcctg gatgatgat gggaatgttt   1260 aatatgctat ctaccgtgtt gggagtagcc gcactaggga tcaaaaacat tggaaacaaa   1320
gaatacttat gggatggact gcaatcttct gatgattttg ctctgttgt taatgcaaaa   1380 gatgaagaga catgtatgga aggaataaac gattttttacc gaacatgtaa gctattggga   1440
ataaacatga gcaaaagaa aagttactgt aatgaaactg gaatgtttga atttacaagc   1500
atgttctaca gagatggatt tgtatctaat tttgcaatgg aacttccttc atttggagtt   1560
gctggagtaa atgaatcagc agatatggca ataggaatga caataataaa gaacaatatg   1620
atcaacaatg ggatgggtcc agcaacagca caaacagcca tacaattatt catagctgat   1680
tatagataca cctacaaatg ccacagggga gattccaaag tggaaggaaa gagaatgaaa   1740
attataaagg agctatggga aaacactaaa ggaagagatg tctgttagt agcagatggt   1800 gggcctaaca tttacaattt gagaaacttg catatcccag aaatagtatt aaagtacaac   1860
```

-continued

| | |
|---|---|
| ctaatggacc ctgaatacaa agggcggtta ctgcatcctc aaaatcccct tgtaggacat | 1920 |
| ttgtctattg agggcatcaa agaggcagat ataaccccag cacatggtcc agtaaagaaa | 1980 |
| atggactatg atgcggtatc tggaactcat agttggagaa ccaaaaggaa cagatctata | 2040 |
| ctaaacactg atcagaggaa catgattctt gaggaacaat gctacgctaa gtgttgcaac | 2100 |
| cttttttgagg cctgttttaa cagtgcatca tacaggaaac cagtaggtca gcacagcatg | 2160 |
| cttgaggcta tggcccacag attaagaatg atgcacgac tagattatga atcaggaaga | 2220 |
| atgtcaaagg atgattttga gaaagcaatg gctcaccttg gtgagattgg gtacatataa | 2280 |
| gcttcgaaga tgtctatggg gttattggtc atcattgaat acatgcggta cacaaatgat | 2340 |
| taaaatgaaa aaaggctcgt gtttctact | 2369 |

<210> SEQ ID NO 5
<211> LENGTH: 2396
<212> TYPE: DNA
<213> ORGANISM: Influenza B virus

<400> SEQUENCE: 5

| | |
|---|---|
| agcagaagcg gagcgttttc aagatgacat tggccaaaat tgaattgtta aaacaactgt | 60 |
| taagggacaa tgaagccaaa acggtattga acaaacaac ggtagaccaa tataacataa | 120 |
| taagaaaatt caatacatca agaattgaaa agaaccccttc attaaggatg aagtgggcca | 180 |
| tgtgttctaa ttttcccttg gctctgacca agggtgatat ggcaaataga atccccttgg | 240 |
| aatacaaggg aatacaactt aaaacaaatg ctgaagacat aggaaccaaa ggccaaatgt | 300 |
| gctcaatagc agcagttacc tggtggaata catatgacc aataggagat actgaaggtt | 360 |
| tcgaaaaggt ctacgaaagc ttttttctca gaaagatgag acttgacaat gccacttggg | 420 |
| gccgaataac ttttggccca gttgaaagag tgagaaaaag ggtactgcta aaccctctca | 480 |
| ccaaggaaat gcctccagat gaagcgagca atgtgataat ggaaatattg ttccctaaag | 540 |
| aagcaggaat accaagagaa tctacttgga tacataggga actgataaaa gaaaaaagag | 600 |
| aaaaattgaa aggaacgatg ataactccca ttgtactggc atacatgctt gagagagaac | 660 |
| tggttgcccg aagaaggttc ctgccagtgg caggagcaac atcagccgag ttcatagaaa | 720 |
| tgctacactg cttacaaggt gaaaattgga gacaaatata tcacccagga gggaataaac | 780 |
| taactgaatc taggtctcaa tcaatgattg tagcttgtag aaaaataatc agaagatcaa | 840 |
| tagtcgcatc aaacccacta gagctagctg tagaaattgc aaacaagact gtgatagata | 900 |
| ctgaaccttt aaaatcatgt ctggcagcca tagacgagg tgatgtagcc tgtgacataa | 960 |
| taagagctgc attaggacta aagatcagac aaagacaaag atttggacgg cttgaactaa | 1020 |
| agagaatatc aggaagagga ttcaaaaatg atgaagaaat attaatcggg aacggaacaa | 1080 |
| tacagaaaat tggaatatgg acggagaag aggagttcca tgtaagatgt ggtgaatgca | 1140 |
| ggggaatatt aaaaaagagc aaaatgaaa tggaaaaact actaataaat tcagccaaaa | 1200 |
| aggaggacat gaaagattta ataatcttgt gcatggtatt ttctcaagac actaggatgt | 1260 |
| tccaaggagt gagaggagaa ataaattttc ttaatcgagc aggccaactt ttatctccaa | 1320 |
| tgtaccaact ccagcgatat tttttgaata ggagcaacga cctttttgat caatgggggt | 1380 |
| atgaggaatc acccaaagca agtgaactac atgggataaa tgaattaatg aatgcatctg | 1440 |
| actatacgtt gaaggggtt gtagtaacaa aaaatgtgat tgatgacttt agttctactg | 1500 |
| aaacagaaaa agtatctata acaaaaaatc ttagtttaat aaaaaggact ggggaagtca | 1560 |
| taatgggggc taatgacgta agtgaattag aatcacaagc acagctaatg ataacatatg | 1620 |

```
atacacctaa gatgtgggag atgggaacaa ccaaagaact ggtgcaaaac acctaccaat   1680
gggtgctaaa aaatttggta acactgaagg ctcagtttct tctgggaaaa gaagacatgt   1740
tccaatggga tgcatttgaa gcatttgaaa gcataatccc ccagaagatg gctggccagt   1800
acagtggatt tgcaagagca gtgctcaaac aaatgagaga ccaagaggtt atgaaaactg   1860
accagttcat aaagttgttg cctttctgtt tctcaccacc aaaattaagg agaaatgggg   1920
agccttatca attcttgagg cttatgttga agggaggagg ggaaaatttc atcgaagtaa   1980
ggaaagggtc ccctctattc tcctacaatc cacaaacaga agtcctaact atatgcggca   2040
gaatgatgtc attaaaagga aaaattgaag atgaagaaag gaatagatca atggggaatg   2100
cagtattggc aggctttctc gttagtggca agtatgaccc agatcttgga gatttcaaaa   2160
ctattgaaga acttgaaaag ctaaaaccgg gggaaaaagc aaacatctta ctttatcaag   2220
gaaagcccgt taaagtagtt aaaaggaaaa gatatagtgc tttatccaat gacatttcac   2280
aaggaattaa gagacaaaga atgacagttg agtccatggg gtgggccttg agctaatata   2340
aatttatcca ttaattcaat agacacaatt gagtgaaaaa tgctcgtgtt tctact       2396

<210> SEQ ID NO 6
<211> LENGTH: 2308
<212> TYPE: DNA
<213> ORGANISM: Influenza B virus

<400> SEQUENCE: 6
agcagaagcg gtgcgtttga tttgccataa tggatacttt tattacaaga aacttccaga     60
ctacaataat acaaaaggcc aaaaacacaa tggcagaatt tagtgaagat cctgaattac    120
aaccagcaat gctattcaac atctgcgtcc atctggaggt ctgctatgta ataagtgata    180
tgaattttct tgatgaagaa ggaaaaacat atacagcatt agaaggacaa ggaaaagaac    240
aaaacttgag accacaatat gaagtgattg agggaatgcc aagaaacata gcatggatgg    300
ttcaaagatc cttagcccaa gagcatggaa tagagactcc aaggtatctg gctgatttgt    360
tcgattataa aaccaagagg tttatagaag ttggaataac aaagggattg gctgacgatt    420
acttttggaa aaagaaagaa aagctgggga atagcatgga actgatgata ttcagctaca    480
atcaagacta ttcgttaagt aatgaatcct cattggatga ggaaggaaaa gggagagtgc    540
taagcagact cacagaactt caggctgagt taagtctgaa aaatctatgg caagttctca    600
taggagaaga agatattgaa aaaggaattg acttcaaact tggacaaaca atatctaaac    660
taagggatat atctgttcca gctggtttct ccaattttga aggaatgagg agctacatag    720
acaatataga tcctaaagga gcaatagaga gaaatctagc aaggatgtct cccttagtat    780
cagttacacc taaaaagttg aaatgggagg acctaagacc aatagggcct cacatttaca    840
accatgagct accagaagtt ccatataatg cctttcttct aatgtctgat gagttggggc    900
tggctaatat gactgaaggg aagtccaaga aaccgaagac cttagccaaa gaatgtctag    960
aaaagtactc aacactacgg gatcaaactg acccaatatt aataatgaaa agcgaaaaag   1020
ctaacgaaaa cttcttatgg aagctgtgga gggactgtgt aaatacaata agtaatgagg   1080
aaacaagtaa cgaattacag aaaaccaatt atgccaagtg ggccacagga gatggattaa   1140
cataccagaa aataatgaaa gaagtagcaa tagatgacga aacaatgtac caagaagagc   1200
ccaaaatacc taacaaatgt agagtggctg cttgggttca aacagagatg aatctattga   1260
gcactctgac aagtaaaagg gccctggatc taccagaaat agggccagac gtagcaccca   1320
tggagcatgt agggagtgaa agaaggaaat actttgttaa tgaaatcaac tactgtaagg   1380
```

```
cctctaccgt tatgatgaag tatgtacttt ttcacacttc attattaaat gaaagcaatg      1440
ccagcatggg aaaatataaa gtaataccaa taaccaacag agtagtaaat gaaaaaggag      1500
aaagttttga catgcttcat ggtctggcgg ttaaagggca atctcatctg aggggagata      1560
ctgatgttgt aacagttgtg actttcgaat ttagtagtac agatcccaga gtggactcag      1620
gaaagtggcc aaaatatact gtatttagaa ttggctcctt atttgtgagt ggaagggaaa      1680
aatctgtgta cctatattgc cgagtgaatg gtacaaataa gatccaaatg aaatggggaa      1740
tggaagctag aagatgtctg cttcaatcaa tgcaacaaat ggaagcaatt gttgaacaag      1800
aatcatcgat acaaggatat gacatgacca aagcttgttt caagggagac agagtgaata      1860
gtcccaaaac tttcagtatt gggactcaag aaggaaaact agtaaaagga tcctttggga      1920
aagcactaag agtaatattc accaaatgtt gatgcacta tgtatttgga aatgcccaat      1980 tggagggggtt tagtgccgaa tctaggagac ttctactgtt aattcaggca ttaaaggaca      2040
gaaagggccc ttgggtattc gacttagagg gaatgtattc tggaatagaa gaatgtatta      2100
gtaacaaccc ttgggtaata cagagtgcat actggtttaa tgaatggttg ggctttgaaa      2160
aagaggggag taaagtatta gaatcaatag atgaaataat ggatgaatga agaagggca      2220 tagcgctcaa tttggtacta ttttgttcat tatgtatcta aacatccaat aaaaagaatt      2280
gagaattaaa aatgcacgtg tttctact                                        2308

<210> SEQ ID NO 7
<211> LENGTH: 1884
<212> TYPE: DNA
<213> ORGANISM: Influenza B virus

<400> SEQUENCE: 7
agcagaagca gagcattttc taatatccac aaaatgaagg caataattgt actactcatg        60
gtagtaacat ccaatgcaga tcgaatctgc actgggataa catcgtcaaa ctcaccccat       120
gtggtcaaaa ctgctactca aggggaagtc aacgtgactg tgtgatacc actgacaaca       180 acacctacca aatctcattt tgcaaatctc aaaggaacac agaccagagg gaaactatgc       240
ccaaactgtc tcaactgcac agatctggac gtggccttgg gcagaccaaa gtgtatgggg       300 accataccctt cggcaaaagc ttcaatactc cacgaagtca aacctgttac atctgggtgc       360
tttcctataa tgcacgacag aacaaaaatc agacagctac ccaatcttct cagaggatat       420
gaaaatatca ggttatcagc ccgtaacgtt atcaacgcag aaacggcacc aggaggaccc       480
tacatagttg aacctcagg atcttgccct aacgttacca atgggaaagg attcttcgca       540
acaatggctt gggctgtccc aaaaaacaac aaaaccaaaa cagcaacgaa cccattaaca       600
gtagaagtac catacatttg tacaaaagga gaagaccaaa ttactgtttg ggggttccat       660
tctgatgacg aaacccaaat ggtaacactc tatggagact cgaagcctca aaagttcacc       720
tcatctgcca acgagtaac cacacattat gtttctcaga ttggtggctt cccaaatcaa       780
acagaagacg aagggctacc acaaagcggc agaattgttg ttgattacat ggtgcaaaaa       840
cctggaaaaa caggaacaat tgtctatcaa agaggtgttt tattgcctca aaaagtgtgg       900
tgcgcaagtg gcaggagcaa ggtaataaaa ggggccttgc cttaattgg tgaagcagat       960 tgcctccacg aaaaatacgg tggattaaac aaaagcaagc cttactacac aggagaacat      1020
gcaaaagcca taggaaattg cccaatatgg gtgaaaacac ccttgaagct ggccaatgga      1080
accaaatata gacctcctgc aaaactatta aaggaaggg gttcttcgg agctattgct      1140 ggtttcttgg aaggaggatg ggaaggaatg attgcaggtt ggcacggata cacatctcat      1200
```

-continued

```
ggagcacatg gagtggcagt ggcagcagac cttaagagta cgcaagaagc tataaacaag   1260
ataacaaaaa atctcaattc tttaagtgag ctagaagtaa agaatcttca aagactaagc   1320
ggtgcaatgg atgaactcca caacgaaata ctcgagctgg atgagaaagt ggatgatctc   1380
agagctgata caataagctc gcaaatagag cttgcagtct tgctttccaa cgaaggaata   1440
ataaacagtg aagatgagca tctcttggca cttgaaagaa aactgaagaa aatgctgggc   1500
ccctctgctg tagacatagg gaatggatgc ttcgaaacca aacacaaatg caaccagact   1560
tgcctagaca ggatagctgc tggcaccttt aatgcaggag aattttctct tcccactttt   1620
gattcactaa atattactgc tgcatcttta aatgatgatg gattggataa tcatactata   1680
ctgctctact actcaactgc tgcttctagt ttggctgtaa cattgatgat agctatcttt   1740
attgtttata tggtctccag agacaatgtt tcttgctcca tctgtctata aggaaaatta   1800
agccctgtat tttcctttat tgtagtgctt gtttgcttgt caccattaca aaaaacgtta   1860
ttgaaaaatg ctcttgttac tact                                          1884
```

<210> SEQ ID NO 8
<211> LENGTH: 1842
<212> TYPE: DNA
<213> ORGANISM: Influenza B virus

<400> SEQUENCE: 8

```
agcagaagca cagcattttc ttgtgaactt caagtaccaa caaaaactga aaatcaaaat     60
gtccaacatg gatattgacg gcatcaacac tggaacaatt gacaaaaacac cagaagaaat   120 aacttccgga accagtgggg caaccagacc aatcatcaaa ccagcaaccc ttgccccacc    180
aagcaacaaa cgaacccgaa acccatcccc ggaaagggca gccacaagca gtgaagctga    240
tgtcggaagg agaacccaaa agaaacaaac cccgacagag ataaagaaga gcgtctacaa    300
tatggtagtg aaactgggtg aattctacaa ccagatgatg gtcaaagctg gactcaacga    360
tgacatggag agaaacctaa tccaaaatgc acatgctgcg gaaagaattc tattggctgc    420
tactgatgac aagaaaactg aattccaaaa gaaaaagaat gccagagatg tcaaagaagg    480
gaaagaagaa atagaccaca acaaaacagg aggcaccttt tacaagatgg taagagatga    540
taaaaccatc tacttcagcc ctataagaat taccttttta aaagaagagg tgaaaacaat    600
gtacaaaacc accatgggga gtgatggttt cagtggacta aatcacatca tgattgggca    660
ttcacagatg aacgatgtct gtttccaaag atcaaaggca ctaaaaagag ttggacttga    720
cccttcatta atcagtactt ttgcaggaag cacactcccc agaagatcag gtgcaactgg    780
tgttgcgatc aaaggaggtg gaactttagt ggcagaagcc attcgattta taggaagagc    840
aatggcagac agagggctat tgagagacat cagagccaag acggcctatg aaaagattct    900
tctgaatctg aaaaacaagt gctctgcgcc ccaacaaaag gctctagttg atcaagtgat    960
cggaagtaga aatccaggga ttgcagacat agaagaccta accctgcttg cccgaagcat   1020
ggtcgttgtc aggccctctg tagcgagcaa agtggtgctt cccataagca tttatgccaa   1080
aatacctcaa ctagggttca atgttgaaga atactctatg gttgggtatg aagccatggc   1140
tctttataat atggcaacac ctgtttccat attaagaatg ggagacgatg caaaagataa   1200
atcacaatta ttcttcatgt cttgcttcgg agctgcctat gaagacctaa gagttttgtc   1260
tgcactaaca ggcacagaat tcaagcatag gtcagcatta aagtgcaagg gtttccacgt   1320
tccagcaaag gagcaagtgg aaggaatggg ggcagctctg atgtccatca agctccagtt   1380
ttgggctcca atgaccagat ctggggggaa tgaagtaggt ggagacggag ggtctggtca   1440
```

-continued

| | |
|---|---|
| aataagttgc agccccgtgt ttgcagtaga aagacctatt gctctaagca agcaagctgt | 1500 |
| aagaagaatg ctgtcaatga atattgaggg acgtgatgca gatgtcaaag gaaatctact | 1560 |
| caagatgatg aatgattcaa tgactaagaa accaatgga aatgctttca ttgggaagaa | 1620 |
| aatgtttcaa atatcagaca aaaacaaaac caatcccatt gagattccaa ttaagcagac | 1680 |
| catccccaat ttcttctttg ggagggacac agcagaggat tatgatgacc tcgattatta | 1740 |
| aagcaacaaa atagacacta tggctgtgac tgtttcagta cgtttggaat gtgggtgttt | 1800 |
| acttttattg aaataaatgt aaaaaatgct gttgtttcta ct | 1842 |

<210> SEQ ID NO 9
<211> LENGTH: 1557
<212> TYPE: DNA
<213> ORGANISM: Influenza B virus

<400> SEQUENCE: 9

| | |
|---|---|
| agcagaagca gagcatcttc tcaaaactga agcaaatagg ccaaaaatga acaatgctac | 60 |
| cttcaactat acaaacgtta accctatttc tcacatcagg gggagtgtta ttatcactat | 120 |
| atgtgtcagc ttcactgtca tacttattgt attcggatat attgctaaaa ttttcaccaa | 180 |
| caaaaataac tgcaccaaca atgtcattgg attgcgcgaa cgtatcaaat gttcaggctg | 240 |
| tgaaccgttc tgcaacaaaa gagatgacat ttcttctccc agagccggag tggacatacc | 300 |
| ctcgtttatc ttgccagggc tcaaccttt agaaagcact cctaattagc cctcataggt | 360 |
| tcggagaaac cagaggaaac tcagctccct tgataataag ggaacccttt gttgcttgtg | 420 |
| gaccaaagga atgcagacac tttgctctaa cccattatgc agctcaacca ggggatact | 480 |
| acaatggaac aagaaggac agaaacaagc tgaggcatct gatttcagtc aaattaggca | 540 |
| aaatcccaac tgtagaaaac tccatttttcc acatggcagc ttggagtggg tccgcatgcc | 600 |
| atgatggtag agaatggaca tatatcggag ttgatggccc tgacagtaat gcactgatca | 660 |
| aaataaaata tggagaagca tatactgaca ataccattc ctatgcaaac aacatcctaa | 720 |
| gaacacaaga aagtgcctgc aattgcatcg ggggagattg ttatcttatg ataactgatg | 780 |
| gctcagcttc aggaattagt aaatgcagat tccttaaaat tcgagagggt cgaataataa | 840 |
| aagaaatatt tccaacagga agagtagagc atactgaaga atgcacatgc gggttcgcca | 900 |
| gcaataaaac catagaatgt gcctgtagag ataacagtta cacagcaaaa agacccttg | 960 |
| tcaaattaaa tgtggagact gatacagctg aaataagatt gatgtgcaca gagacttatt | 1020 |
| tggacacccc cagaccagat gatggaagca taacagggcc ttgcgaatct aatggggaca | 1080 |
| aagggcttgg aggcatcaaa ggaggatttg tccatcaaag aatggcatct aagattggaa | 1140 |
| gatggtactc ccgaacgatg tctaaaactg aaagaatggg gatggaactg tatgtcaagt | 1200 |
| atgatggaga cccatggact gacagtgacg cccttgctcc tagtggagta atggtttcaa | 1260 |
| tgaaagaacc tggttggtat tcttttggct tcgaaataaa agataagaaa tgtgatgtcc | 1320 |
| cctgtattgg gatagagatg gtacacgatg gtggaaaaga acttggcac tcagcagcaa | 1380 |
| cagccattta ctgtttgatg ggctcaggac aattgctatg gacactgtc acaggtgttg | 1440 |
| atatggctct gtaatggagg aatggttgaa tctgttctaa accctttgtt cctattttgt | 1500 |
| ttgaacaatt gtccttactg gacttaattg tttctgaaaa atgctcttgt tactact | 1557 |

<210> SEQ ID NO 10
<211> LENGTH: 1190
<212> TYPE: DNA
<213> ORGANISM: Influenza B virus

```
<400> SEQUENCE: 10
agcagaagca cgcactttct taaaatgtcg ctgtttggag acacaattgc ctacctgctt      60
tcactaacag aagatggaga aggcaaagca gaactagcag aaaaattaca ctgttggttc     120
ggtgggaaag aatttgacct agactctgct ttggaatgga taaaaacaa aagatgccta     180
actgatatac aaaaagcact aattggtgcc tctatctgct ttttaaaacc caaagaccaa     240
gaaagaaaaa aagagattcat cacagagccc ctgtcaggaa tgggaacaac agcaacaaaa     300
aagaaaggcc tgattctagc tgagagaaaa atgagaagat gtgtgagttt catgaagca      360
tttgaaatag cagaaggcca tgaaagctca gcactactat attgtctcat ggtcatgtac     420
ctgaaccctg aaattattc aatgcaagta aaactaggaa cgctctgtgc tttatgcgag      480
aaacaagcat cacattcaca aagagctcat agcagagcag caagatcttc agtgcctgga     540
gtgaggcgag aaatgcagat ggtttcagct gtgaacacag caaaaacaat gaatggaatg     600
gggaagggag aagacgtcca aaaactggca gaagagctgc aaagcaacat tggagtattg     660
agatctctgg gggcaagtca aaagaatgga gaaggaattg caaggatgt aatggaagtg      720
ctaaagcaga gctctatggg aaattcagct cttgtgaaga atacctata atgctcgaac     780
catttcagat tctttcaatt tgttctttca tttatcagc tctccatttc atggcttgga      840
caatagggca tttgaatcaa ataaaaagag gagtaaacct gaaaatacga ataagaaatc     900
caaataaaga gacaataaac agagaggtat caattttgag acacagttac caaaagaaa      960
tccaagccaa agaacaatg aaggaagtac tctctgacaa catggagata ttgagtgacc    1020
acatagtaat tgagggggctt tctgctgaag agataataaa aatgggtgaa acagttttgg    1080
aggtagaaga attgcagtaa acccaatttt caccgtattt cttgctatgc atttaagcaa    1140
attgtaatca atgtcagcaa ataaactgga aaaagtgcgt tgtttctact                1190

<210> SEQ ID NO 11
<211> LENGTH: 1098
<212> TYPE: DNA
<213> ORGANISM: Influenza B virus

<400> SEQUENCE: 11
agcagaagca gaggatttgt ttagtcactg gcaaacggaa aaaatggcg acaacatga       60
ccacaacaca aattgaggta ggtccgggag caaccaatgc caccataaac tttgaagcag    120
gaattctgga gtgctatgaa aggctttcat ggcaaagagc ccttgactac cctggtcaag    180
accgcctaaa cagactaaag agaaaattag aatcaagaat aaagactcac aacaaaagtg    240
agcctgaaag taaaaggatg tctcttgaag agagaaaagc aattggggta aaaatgatga    300
aagtgctcct atttatgaat ccatctgctg gaattgaagg gtttgagcca tactgtatga    360
aaaattcctc aaatagcaac tgtccaaact gcaattggac cgattaccct ccaacaccag    420
gaaagtgcct tgatgacata gaagaagaac cggagaatgt tgatgaccca actgaaatag    480
tattgaggga catgaacaac aaagatgcaa ggcaaaagat aaaggaggaa gtaaacactc    540
agaaagaagg gaagttccgt ttgacaataa aaagggatat acgtaatgtg ttgtccttga    600
gagtgttggt aaacggaaca ttcctcaagc accctaatgg atacaagtcc ttatcaactc    660
tgcatagatt gaatgcatat gaccagagtg ggaggcttgt tgctaaactt gttgctactg    720
atgatcttac agtggaggat gaagaagatg ccatcggat cctcaactca ctcttcgagc    780
gttttaatga aggacattca aagccaattc gagcagctga aactgcggtg ggagtcttat    840
cccaatttgg tcaagagcac cgattatcac cagaggaggg agacaattag actggttacg    900
```

```
gaagaacttt atcttttaag taaaagaatt gatgataaca tattgttcca caaacagta    960 atagctaaca gctccataat agctgacatg attgtatcat tatcattatt ggaaacattg   1020
tatgaaatga aggatgtggt tgaagtgtac agcaggcagt gcttgtgaat ttaaaataaa   1080
aatcctcttg ttactact                                                 1098
```

```
<210> SEQ ID NO 12
<211> LENGTH: 71
<212> TYPE: PRT
<213> ORGANISM: Influenza B virus

<400> SEQUENCE: 12
```

Ser Gly Ser Cys Pro Asn Val Thr Asn Gly Asn Gly Phe Phe Ala Thr
1               5                   10                  15

Met Ala Trp Ala Val Pro Lys Asn Asp Asn Lys Thr Ala Thr Asn
            20                  25                  30

Pro Leu Thr Val Glu Val Pro Tyr Ile Cys Thr Glu Gly Glu Asp Gln
        35                  40                  45

Ile Thr Val Trp Gly Phe His Ser Asp Ser Glu Thr Gln Met Val Lys
    50                  55                  60

Leu Tyr Gly Asp Ser Lys Pro
65                  70

```
<210> SEQ ID NO 13
<211> LENGTH: 69
<212> TYPE: PRT
<213> ORGANISM: Influenza B virus

<400> SEQUENCE: 13
```

Ser Gly Ser Cys Pro Asn Val Thr Ser Arg Asn Gly Phe Phe Ala Thr
1               5                   10                  15

Met Ala Trp Ala Val Pro Arg Asp Asn Lys Thr Ala Thr Asn Pro Leu
            20                  25                  30

Thr Val Glu Val Pro Tyr Ile Cys Thr Lys Gly Glu Asp Gln Ile Thr
        35                  40                  45

Val Trp Gly Phe His Ser Asp Asp Lys Thr Gln Met Lys Lys Leu Tyr
    50                  55                  60

Gly Asp Ser Asn Pro
65

```
<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tattcgtctc agggagcaga agcggagcct ttaagatg                             38

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tattcgtctc gatgccgttc cttcttcatt gaagaatgg                            39
```

```
<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tattcgtctc ggcatctttg tcgcctggga tgatgatg                            38

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atatcgtctc gtattagtag aaacacgagc ctt                                 33

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tattcgtctc agggagcaga agcggagcgt tttcaagatg                          40

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tattcgtctc tctcattttg ctctttttta atattcccc                           39

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tattcgtctc atgagaatgg aaaaactact aataaattca gc                       42

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atatcgtctc gtattagtag aaacacgagc att                                 33
```

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
tattcgtctc agggagcaga agcggtgcgt ttga        34

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
tattcgtctc ccagggccct tttacttgtc agagtgc        37

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
tattcgtctc tcctggatct accagaaata gggccagac        39

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
atatcgtctc gtattagtag aaacacgtgc att        33

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tattcgtctc agggagcaga agcagagcat tttctaatat c        41

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
atatcgtctc gtattagtag taacaagagc atttttc        37

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tattggtctc agggagcaga agcacagcat tttcttgt          38

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
atatggtctc gtattagtag aaacaacagc attttt          36

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
tattcgtctc agggagcaga agcagagcat cttctcaaaa c          41

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
atatcgtctc gtattagtag taacaagagc attttttcag          39

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tattcgtctc agggagcaga agcacgcact ttcttaaaat g          41

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
atatcgtctc gtattagtag aaacaacgca ctttttccag          40

```
<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tattcgtctc agggagcaga agcagaggat ttgtttagtc                            40

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atatcgtctc gtattagtag taacaagagg atttttat                              38

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tattcgtctc agggagcaga agcacagcat tttcttgtg                             39

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atatcgtctc gtattagtag aaacaacagc attttttac                             39

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tattcgtctc agggagcaga agcagagca                                        29

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atatcgtctc gtattagtag taacaagagc atttt                                 35
```

```
<210> SEQ ID NO 40
<211> LENGTH: 12
<212> TYPE: DNA
<213> ORGANISM: Influenza B virus

<400> SEQUENCE: 40
catgacggtg ac                                                        12

<210> SEQ ID NO 41
<211> LENGTH: 15
<212> TYPE: DNA
<213> ORGANISM: Influenza B virus

<400> SEQUENCE: 41
gggaagtcaa cgtga                                                     15

<210> SEQ ID NO 42
<211> LENGTH: 15
<212> TYPE: DNA
<213> ORGANISM: Influenza B virus

<400> SEQUENCE: 42
ccctccaacg ccagg                                                     15

<210> SEQ ID NO 43
<211> LENGTH: 21
<212> TYPE: DNA
<213> ORGANISM: Influenza B virus

<400> SEQUENCE: 43
aaaagagctc tggacctacc a                                              21

<210> SEQ ID NO 44
<211> LENGTH: 21
<212> TYPE: DNA
<213> ORGANISM: Influenza B virus

<400> SEQUENCE: 44
aaaagggccc tggatctacc a                                              21

<210> SEQ ID NO 45
<211> LENGTH: 2369
<212> TYPE: DNA
<213> ORGANISM: Influenza B virus

<400> SEQUENCE: 45
agcagaagcg gagcctttaa gatgaatata aatccttatt ttctcttcat agatgtaccc     60
atacaggcag caatttcaac aacattccca tacaccggtg ttccccctta ttcccatgga    120
acgggaacag gctacacaat agacaccgtg attagaacac atgagtactc aaacaaggga    180
aaacaataca tttctgatgt tacaggatgt gcaatggtag atccaacaaa tgggccatta    240
cccgaagata tgagccgag tgcctatgca caattggatt gcgttctgga ggctttggat    300
agaatggatg aagaacatcc aggtctgttt caagcagcct cacagaatgc catggaggca    360
ctaatggtca caactgtaga caaattaacc caggggagac agactttga ttggacagtg    420 tgcagaaacc aacctgctgc aacggcactg aacacaacaa taacctcttt taggttgaat    480
gatttgaatg gagccgacaa gggtggatta gtacccttt gccaagatat cattgattca    540
ttggacaaac tgaaatgac tttcttctcg gtaaagaata taagaaaaa attgcctgct    600 aaaaacagaa agggtttcct cataaagaga ataccaatga aggtaaaaga cagaataacc    660
```

-continued

```
agagtggaat acatcaaaag agcattatca ttaaacacaa tgacaaaaga tgctgaaaga    720
ggcaaactaa aaagaagagc aattgccacc gctgggatac aaatcagagg gtttgtatta    780
gtagttgaaa acttggctaa aaatatctgt gaaaatctag aacaaagtgg tttgccagta    840
ggtgggaacg agaagaaggc caaactgtca aatgcagtgg ccaaaatgct cagtaactgc    900
ccaccaggag ggatcagcat gacggtgaca ggagacaata ctaaatggaa tgaatgctta    960
aatccaagaa tctttttggc tatgactgaa agaataacca gagacagccc aatttggttc   1020
cgggattttt gtagtatagc accggtcttg ttctccaata aaatagccag attgggaaaa   1080
gggttcatga taacaagcaa aacaaaaaga ctgaaggctc aaataccttg tcccgatctg   1140
tttaatatac cattagaaag atataatgaa gaaacaaggg caaaattaaa aaagctgaaa   1200
ccattcttca atgaagaagg aacggcatct ttgtcgcctg ggatgatgat gggaatgttt   1260
aatatgctat ctaccgtgtt gggagtagcc gcactaggga tcaaaaacat tggaaacaaa   1320
gaatacttat gggatggact gcaatcttct gatgattttg ctctgtttgt taatgcaaaa   1380
gatgaagaga catgtatgga aggaataaac gatttttacc gaacatgtaa gctattggga   1440
ataaacatga gcaaaaagaa aagttactgt aatgaaactg gaatgtttga atttacaagc   1500
atgttctaca gagatggatt tgtatctaat tttgcaatgg aacttccttc atttggagtt   1560
gctggagtaa atgaatcagc agatatggca ataggaatga caataataaa gaacaatatg   1620
atcaacaatg ggatgggtcc agcaacagca caaacagcca tacaattatt catagctgat   1680
tatagataca cctacaaatg tcacagggga gattccaaag tggaaggaaa gagaatgaaa   1740
attataaagg agctatggga aaacactaaa ggaagagatg gtctgttagt agcagatggt   1800
gggcctaaca tttacaattt gagaaacttg catatcccag aaatagtatt aaagtacaac   1860
ctaatggacc ctgaatacaa agggcggtta ctgcatcctc aaaatccctt tgtaggacat   1920
ttgtctattg agggcatcaa agaggcagat ataaccccag cacatggtcc agtaaagaaa   1980
atggactatg atgcggtatc tggaactcat agttggagaa ccaaaaggaa cagatctata   2040
ctaaacactg atcagaggaa catgattctt gaggaacaat gctacgctaa gtgttgcaac   2100
ctttttgagg cctgttttaa cagtgcatca tacaggaaac cagtaggtca gcacagcatg   2160
cttgaggcta tggcccacag attaagaatg gatgcacgac tagattatga atcaggaaga   2220
atgtcaaagg atgattttga gaaagcaatg gctcaccttg gtgagattgg gtacatataa   2280
gcttcgaaga tgtctatggg gttattggtc atcattgaat acatgcggta cacaaatgat   2340
taaaatgaaa aaaggctcgt gtttctact                                      2369
```

<210> SEQ ID NO 46
<211> LENGTH: 1884
<212> TYPE: DNA
<213> ORGANISM: Influenza B virus

<400> SEQUENCE: 46

```
agcagaagca gagcattttc taatatccac aaaatgaagg caataattgt actactcatg     60
gtagtaacat ccaatgcaga tcgaatctgc actgggataa catcgtcaaa ctcaccccat    120
gtggtcaaaa ctgctactca aggggaagtt aatgtgactg gtgtgatacc actgacaaca    180
acacctacca aatctcattt tgcaaatctc aaaggaacac agaccagagg gaaactatgc    240
ccaaactgtc tcaactgcac agatctggac gtggccttgg gcagaccaaa gtgtatgggg    300
accatacctt cggcaaaagc ttcaatactc cacgaagtca aacctgttac atctgggtgc    360
tttcctataa tgcacgacag aacaaaaatc agacagctac ccaatcttct cagaggatat    420
```

-continued

```
gaaaatatca ggttatcagc ccgtaacgtt atcaacgcag aaacggcacc aggaggaccc    480
tacatagttg gaacctcagg atcttgccct aacgttacca atgggaaagg attcttcgca    540
acaatggctt gggctgtccc aaaaaacaac aaaaccaaaa cagcaacgaa cccattaaca    600
gtagaagtac catacatttg tacaaaagga gaagaccaaa ttactgtttg gggttccat     660 tctgatgacg aaacccaaat ggtaacactc tatggagact cgaagcctca aaagttcacc    720
tcatctgcca acggagtaac cacacattat gtttctcaga ttggtggctt cccaaatcaa    780
acagaagacg aagggctacc acaaagcggc agaattgttg ttgattacat ggtgcaaaaa    840
cctggaaaaa caggaacaat tgtctatcaa agaggtgttt tattgcctca aaaagtgtgg    900
tgcgcaagtg gcaggagcaa ggtaataaaa ggggccttgc ctttaattgg tgaagcagat    960
tgcctccacg aaaaatacgg tggattaaac aaaagcaagc cttactacac aggagaacat   1020
gcaaaagcca taggaaattg cccaatatgg gtgaaaacac ccttgaagct ggccaatgga   1080
accaaatata gacctcctgc aaaactatta aaggaaaggg gtttcttcgg agctattgct   1140
ggtttcttgg aaggaggatg ggaaggaatg attgcaggtt ggcacggata cacatctcat   1200
ggagcacatg gagtggcagt ggcagcagac cttaagagta cgcaagaagc tataaacaag   1260
ataacaaaaa atctcaattc tttaagtgag ctagaagtaa agaatcttca aagactaagc   1320
ggtgcaatgg atgaactcca caacgaaata ctcgagctgg atgagaaagt ggatgatctc   1380
agagctgata caataagctc gcaaatagag cttgcagtct tgctttccaa cgaaggaata   1440
ataaacagtg aagatgagca tctcttggca cttgaaagaa aactgaagaa aatgctgggc   1500
ccctctgctg tagacatagg gaatggatgc ttcgaaacca aacacaaatg caaccagact   1560
tgcctagaca ggatagctgc tggcaccttt aatgcaggag aattttctct tcccactttt   1620
gattcactaa atattactgc tgcatcttta aatgatgatg gattggataa tcatactata   1680
ctgctctact actcaactgc tgcttctagt ttggctgtaa cattgatgat agctatcttt   1740
attgtttata tggtctccag agacaatgtt tcttgctcca tctgtctata aggaaaatta   1800
agccctgtat tttcctttat tgtagtgctt gtttgcttgt caccattaca aaaaacgtta   1860
ttgaaaaatg ctcttgttac tact                                          1884
```

<210> SEQ ID NO 47
<211> LENGTH: 1098
<212> TYPE: DNA
<213> ORGANISM: Influenza B virus

<400> SEQUENCE: 47

```
agcagaagca gaggatttgt ttagtcactg gcaaacggaa aaaaatggcg gacaacatga     60
ccacaacaca aattgaggta ggtccgggag caaccaatgc caccataaac tttgaagcag    120
gaattctgga gtgctatgaa aggctttcat ggcaaagagc ccttgactac cctggtcaag    180
accgcctaaa cagactaaag agaaaattag aatcaagaat aaagactcac aacaaaagtg    240
agcctgaaag taaaaggatg tctcttgaag agagaaaagc aattggggta aaaatgatga    300
aagtgctcct atttatgaat ccatctgctg gaattgaagg gtttgagcca tactgtatga    360
aaaattcctc aaatagcaac tgtccaaact gcaattggac cgattaccct ccaacgccag    420
gaaagtgcct tgatgacata gaagaagaac cggagaatgt tgatgaccca actgaaatag    480
tattgaggga catgaacaac aaagatgcaa ggcaaaagat aaaggaggaa gtaaacactc    540
agaaagaagg gaagttccgt ttgacaataa aaagggatat acgtaatgtg ttgtccttga    600
gagtgttggt aaacggaaca ttcctcaagc accctaatgg atacaagtcc ttatcaactc    660
```

```
tgcatagatt gaatgcatat gaccagagtg ggaggcttgt tgctaaactt gttgctactg    720
atgatcttac agtggaggat gaagaagatg gccatcggat cctcaactca ctcttcgagc    780
gttttaatga aggacattca aagccaattc gagcagctga aactgcggtg ggagtcttat    840
cccaatttgg tcaagagcac cgattatcac cagaggaggg agacaattag actggttacg    900
gaagaacttt atcttttaag taaagaatt gatgataaca tattgttcca caaacagta     960 atagctaaca gctccataat agctgacatg attgtatcat tatcattatt ggaaacattg   1020
tatgaaatga aggatgtggt tgaagtgtac agcaggcagt gcttgtgaat ttaaaataaa   1080
aatcctcttg ttactact                                                 1098
```

<210> SEQ ID NO 48
<211> LENGTH: 4
<212> TYPE: PRT
<213> ORGANISM: Influenza B virus

<400> SEQUENCE: 48

Asn Lys Thr Gln
1

<210> SEQ ID NO 49
<211> LENGTH: 4
<212> TYPE: PRT
<213> ORGANISM: Influenza B virus

<400> SEQUENCE: 49

Asp Lys Thr Gln
1

<210> SEQ ID NO 50
<211> LENGTH: 4
<212> TYPE: PRT
<213> ORGANISM: Influenza B virus

<400> SEQUENCE: 50

Asn Lys Thr Pro
1

<210> SEQ ID NO 51
<211> LENGTH: 4
<212> TYPE: PRT
<213> ORGANISM: Influenza B virus

<400> SEQUENCE: 51

Asp Lys Thr Pro
1

<210> SEQ ID NO 52
<211> LENGTH: 4
<212> TYPE: PRT
<213> ORGANISM: Influenza B virus

<400> SEQUENCE: 52

Ser Glu Thr Gln
1

<210> SEQ ID NO 53
<211> LENGTH: 4
<212> TYPE: PRT
<213> ORGANISM: Influenza B virus

```
<400> SEQUENCE: 53

Asn Glu Ala Gln
1

<210> SEQ ID NO 54
<211> LENGTH: 4
<212> TYPE: PRT
<213> ORGANISM: Influenza B virus

<400> SEQUENCE: 54

Asn Glu Asn Gln
1

<210> SEQ ID NO 55
<211> LENGTH: 4
<212> TYPE: PRT
<213> ORGANISM: Influenza B virus

<400> SEQUENCE: 55

Asn Lys Ile Gln
1

<210> SEQ ID NO 56
<211> LENGTH: 4
<212> TYPE: PRT
<213> ORGANISM: Influenza B virus

<400> SEQUENCE: 56

Ser Lys Thr Gln
1

<210> SEQ ID NO 57
<211> LENGTH: 4
<212> TYPE: PRT
<213> ORGANISM: Influenza B virus

<400> SEQUENCE: 57

Asn Lys Ser Gln
1

<210> SEQ ID NO 58
<211> LENGTH: 4
<212> TYPE: PRT
<213> ORGANISM: Influenza B virus

<400> SEQUENCE: 58

Asn Glu Thr Gln
1
```